US009192185B2

(12) United States Patent
Tominaga et al.

(10) Patent No.: US 9,192,185 B2
(45) Date of Patent: Nov. 24, 2015

(54) EQUOL-CONTAINING EXTRACT, METHOD FOR PRODUCTION THEREOF, METHOD FOR EXTRACTION OF EQUOL, AND EQUOL-CONTAINING FOOD

(71) Applicant: OTSUKA PHARMACEUTICAL CO., LTD., Chiyoda-ku, Tokyo (JP)

(72) Inventors: Michiaki Tominaga, Osaka (JP); Takao Taki, Osaka (JP); Toshiaki Matsumoto, Osaka (JP); Izumi Hanya, Osaka (JP); Takuma Imada, Osaka (JP); Kunihiko Matsuoka, Osaka (JP); Takuya Kishimoto, Osaka (JP); Yuko Uchiyama, Osaka (JP); Hiromasa Tsuneishi, Otsu (JP); Machiko Tsuji, Otsu (JP); Tania Valdes-Gonzalez, Osaka (JP); Kentaro Tadano, Osaka (JP); Kyoko Kameda, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/673,484

(22) Filed: Nov. 9, 2012

(65) Prior Publication Data
US 2013/0066085 A1   Mar. 14, 2013

Related U.S. Application Data

(62) Division of application No. 12/664,298, filed as application No. PCT/JP2008/060913 on Jun. 13, 2008, now Pat. No. 8,900,645.

(30) Foreign Application Priority Data

Jun. 13, 2007 (JP) ................................ 2007-156822
Jun. 13, 2007 (JP) ................................ 2007-156825
Jun. 13, 2007 (JP) ................................ 2007-156833

(51) Int. Cl.
*B01D 11/00* (2006.01)
*A23L 1/30* (2006.01)
(Continued)

(52) U.S. Cl.
CPC ............... *A23L 1/3002* (2013.01); *A21D 2/368* (2013.01); *A23C 9/1307* (2013.01);
(Continued)

(58) Field of Classification Search
IPC ....... A23L 1/3002; A21D 2/368; A23C 9/1307; B01D 11/00
See application file for complete search history.

(56) References Cited

U.S. PATENT DOCUMENTS 2,590,647 A    4/1928  Pettibone
(Continued)

FOREIGN PATENT DOCUMENTS

CA           2294062 A1    12/1998
(Continued)

OTHER PUBLICATIONS

The Lab Depot Inc., Ethyl Acetate http://www.labdepotinc.com/Product_Details~id~897~pid~61643.aspx?gclid=CJOHiav0jsMCFYtr7AodlXMAyw 1 page, accessed from the WWW on Jan. 12, 2015.*
(Continued)

*Primary Examiner* — Patricia A Leith
(74) *Attorney, Agent, or Firm* — Sughrue Mion, PLLC

(57) ABSTRACT

The present invention relates to an extract obtained by extracting useful components containing equol from an equol-containing fermented soybean hypocotyl, and to a method for producing the same.
The present invention makes it possible to efficiently obtain useful components containing equol from the fermented soybean hypocotyl by subjecting an equol-containing fermented soybean hypocotyl to extraction using an ethanol aqueous solution as an extractant. The present invention reduces the content of saponin, which causes an unpleasant taste, by sequentially subjecting the equol-containing fermented soybean hypocotyl to extraction using an ethanol aqueous solution and ethanol, while efficiently extracting equol and glycitein.

5 Claims, 8 Drawing Sheets
(8 of 8 Drawing Sheet(s) Filed in Color)

(51) Int. Cl.

| | | |
|---|---|---|
| A21D 2/36 | (2006.01) | |
| A23C 9/13 | (2006.01) | |
| A23C 9/154 | (2006.01) | |
| A23C 11/02 | (2006.01) | |
| A23C 11/10 | (2006.01) | |
| A23C 20/02 | (2006.01) | |
| A23F 3/16 | (2006.01) | |
| A23F 5/24 | (2006.01) | |
| A23L 1/015 | (2006.01) | |
| A23L 1/068 | (2006.01) | |
| A23L 1/182 | (2006.01) | |
| A23L 1/187 | (2006.01) | |
| A23L 1/20 | (2006.01) | |
| A23L 1/238 | (2006.01) | |
| A23L 1/24 | (2006.01) | |
| A23L 1/314 | (2006.01) | |
| A23L 1/317 | (2006.01) | |
| A23L 1/325 | (2006.01) | |
| A23L 1/39 | (2006.01) | |
| A23L 2/52 | (2006.01) | |
| A61K 31/353 | (2006.01) | |
| A61K 36/48 | (2006.01) | |

(52) U.S. Cl.
CPC ............ *A23C 9/1315* (2013.01); *A23C 9/1544* (2013.01); *A23C 11/02* (2013.01); *A23C 11/103* (2013.01); *A23C 20/025* (2013.01); *A23F 3/163* (2013.01); *A23F 5/243* (2013.01); *A23L 1/0152* (2013.01); *A23L 1/068* (2013.01); *A23L 1/182* (2013.01); *A23L 1/1875* (2013.01); *A23L 1/2008* (2013.01); *A23L 1/238* (2013.01); *A23L 1/24* (2013.01); *A23L 1/3175* (2013.01); *A23L 1/31436* (2013.01); *A23L 1/3255* (2013.01); *A23L 1/39* (2013.01); *A23L 2/52* (2013.01); *A61K 31/353* (2013.01); *A61K 36/48* (2013.01)

(56) References Cited

U.S. PATENT DOCUMENTS

| | | | |
|---|---|---|---|
| 4,816,407 A | 3/1989 | Matson | |
| 6,716,424 B1 | 4/2004 | Uchiyama et al. | |
| 6,929,004 B1 | 8/2005 | Bonney et al. | |
| 7,029,883 B2 | 4/2006 | Chan | |
| 7,303,778 B2 | 12/2007 | McMindes et al. | |
| 7,345,089 B2 | 3/2008 | Uchiyama et al. | |
| 7,763,276 B1 | 7/2010 | Shodai et al. | |
| 7,939,060 B2 | 5/2011 | Uchiyama et al. | |
| 7,960,573 B2 * | 6/2011 | Setchell et al. | 549/399 |
| 2001/0018197 A1 | 8/2001 | Wong et al. | |
| 2002/0001565 A1 | 1/2002 | Shapiro | |
| 2003/0078214 A1 | 4/2003 | Kelly | |
| 2003/0113390 A1 | 6/2003 | Hoie | |
| 2004/0147594 A1 * | 7/2004 | Setchell et al. | 514/456 |
| 2004/0235758 A1 | 11/2004 | Setchell et al. | |
| 2005/0260303 A1 | 11/2005 | Tritch | |
| 2006/0122262 A1 | 6/2006 | Lephart et al. | |
| 2006/0148045 A1 * | 7/2006 | Uchiyama et al. | 435/125 |
| 2006/0165812 A1 | 7/2006 | Charron | |
| 2007/0027329 A1 * | 2/2007 | Setchell et al. | 549/402 |
| 2007/0043108 A1 | 2/2007 | Lephart et al. | |
| 2007/0149788 A1 * | 6/2007 | Hyatt | 549/404 |
| 2007/0231367 A1 | 10/2007 | Fukui | |
| 2008/0089941 A1 | 4/2008 | Mower | |
| 2010/0029994 A1 | 2/2010 | Manzer et al. | |

FOREIGN PATENT DOCUMENTS

| | | |
|---|---|---|
| CN | 1327983 A | 12/2001 |
| CN | 1183904 C | 1/2005 |
| CN | 1561214 A | 1/2005 |
| CN | 1764440 A | 4/2006 |
| CN | 1764441 A1 | 4/2006 |
| CN | 1849140 A | 10/2006 |
| CN | 1933739 A | 3/2007 |
| CN | 1942183 A | 4/2007 |
| DE | 10118999 A1 | 11/2001 |
| EP | 1 025 850 A1 | 8/2000 |
| EP | 1133308 B1 | 9/2001 |
| JP | 60-049751 A | 3/1985 |
| JP | 5176711 A | 7/1993 |
| JP | 10174555 A | 6/1998 |
| JP | 2000095710 A | 4/2000 |
| JP | 2006-504409 A | 2/2006 |
| JP | 2006-508942 A | 3/2006 |
| JP | 2006204296 A | 8/2006 |
| JP | 2006-296434 A | 11/2006 |
| WO | 0030663 A1 | 6/2000 |
| WO | 03/026655 A1 | 4/2003 |
| WO | 2004/084865 A1 | 10/2004 |
| WO | 2004084864 A1 | 10/2004 |
| WO | 2005089567 A1 | 9/2005 |

OTHER PUBLICATIONS

Extended European Search Report issued May 17, 2010 in EP 08777224.0 (Otsuka Pharmaceutical Co., Ltd.).

Hawley's Condensed Dictionary, "ethyl alcohol", $14^{th}$ Edition, 2002, 1 page.

Tammy E. Hedlund et al., "Long-Term Dietary Habits Affect Soy Isoflavone Metabolism and Accumulation in Prostatic Fluid in Caucasian Men", J. Nutr., 2005, 135: 1400-1406.

LC Laboratories MSDS Sheet, Isoflavone Standards, Jan. 2007, pp. 1-10.

Julie Maubach et al., "Quantitation of soy-derived phytoestrogens in human breast tissue and biological fluids by high-performance liquid chromatography", Journal of Chromatography B, 2003, 784: 137-144.

Keiko Morito et al., "Interaction of Phytoestrogens with Estrogen Receptors α and β", Biol. Pharm. Bull. 2001, 24: 351-356.

M.S. Morton et al., "Lignans and Isoflavonoids in Plasma and Prostatic Fluid in Men: Samples From Portugal, Hong Kong, and the United Kingdom", The Prostate, 1997, 32: 122-128.

Jianping Yuan et al., "An important metabolite of soybean isoflavone-equol", Chinese Pharmaceutical Journal, 2006, 41(7):484-490.

Kenneth D. R. Setchell et al., "The Clinical Importance of the Metabolite Equol—A Clue to the Effectiveness of Soy and Its Isoflavones", The Journal of Nutrition, 2002, 132(12): 3577-3584.

Zhang et al., "Isolation and characterization of gastrointestinal bacteria function on soybean isoflavone metabolization," Research of nutrition and feedstuff for animals, 2006, p. 195.

Jianquan Wu et al., "Research Progress in Equol, a Metabolite of Daidzein", Progress in Physiological Sciences, 2006, 4:359-361.

Chinese Office Action dated Jul. 18, 2013 issued in Chinese Patent Application No. 201210415503.6.

Chinese Office Action dated Jun. 27, 2013 issued in Chinese Patent Application No. 201210415465.4.

Chinese Office Action dated Jul. 1, 2013 issued in Chinese Patent Application No. 201210415488.5.

Fuhrman, "Chocolate and cocoa products: Making the best better", Candy Industry, 2003, 168: 47-48.

Kenneth Setchell et al., "Equol: History, Chemistry, and Formation", The Journal of Nutrition, Supplement: Equol, Soy, and menopause, 2010, 140: 1355S-1362S.

Non-Final Office Action issued in U.S. Appl. No. 12/664,298, dated Oct. 1, 2013.

Kim et al., "Effect of Bifidobacterium-fermented Soy Hypocotyls Intake on the Composition of Human Large Intestinal Bacteria in the Elderly", Food Science and Biotechnology, 2003, 12(2): 178-179.

(56) References Cited

OTHER PUBLICATIONS

Uehara et al., "Transformation of Daidzein to Equol and Its Bioactivity", American Chemical Society, 2008, Chapter 8, pp. 81-89.
Examination Report issued in counterpart Mexican Patent Application No. MX/a/2009/013580, dated Feb. 4, 2014.
Rachel E. Kopec., "Separation and Isolation of (S)-Equol: The Biologically Relevant Metabolite of the Isoflavone Daidzein", Undergraduate Thesis, The Ohio State University, 2006, pp. 1-20.
First Examination Report, dated May 21, 2015, issued by the Intellectual Property Office of India in counterpart Indian Application No. 7727/DELNP/2009.

* cited by examiner

EQUOL-CONTAINING EXTRACT, METHOD FOR PRODUCTION THEREOF, METHOD FOR EXTRACTION OF EQUOL, AND EQUOL-CONTAINING FOOD

CROSS-REFERENCE TO RELATED APPLICATIONS

This is a Divisional of U.S. patent application Ser. No. 12/664,298 filed Dec. 11, 2009, which is a 371 National Stage Entry of PCT/JP2008/060913 filed Jun. 13, 2008, which claims priority of Japanese Patent Application Nos. 2007-156822, 2007-156825, and 2007-156833 all filed Jun. 13, 2007. The entire contents of the aforementioned applications are incorporated herein by reference.

TECHNICAL FIELD

The present invention relates to an equol-containing extract obtained by extracting effective components from an equol-containing fermented soybean hypocotyl and a production method thereof. The present invention also relates to a method for efficiently purifying an equol-containing substance to obtain a highly pure equol. The present invention further relates to an equol-containing food material and an equol-containing food.

BACKGROUND ART

The isoflavones (soybean isoflavones: daidzein, genistein, glycitein) contained in soybeans have structures similar to estradiol, and have anti-estrogen actions associated with binding to estrogen receptors (hereinafter referred to as ER) and estrogen-like actions. The ever conducted epidemiological studies and intervention studies of soybean isoflavones suggest that they have preventive effects due to their anti-estrogen actions on breast cancer, prostate cancer and other hormone-dependent cancers and improving effects due to their estrogen-like actions on menopausal disorders, postmenopausal osteoporosis and hyperlipidemia.

Recently, it has been pointed out that the active component of the physiological effects of these soybean isoflavones may be a metabolite of daidzein, i.e., equol. More specifically, it has been reported that equol has an ability to bind to ER (especially to ERβ) greater than soybean isoflavones and that it has a remarkably high transition capability to target organs such as breast and prostate tissues (Non-Patent Documents 1 to 4). Moreover, a case-control study reports that there are significantly less patients who produce equol in the patients of breast cancer and prostate cancer. The effects of soybean isoflavones that improve bone density and lipid metabolism were examined regarding postmenopausal women categorized into two groups: those who produce equol and those who do not. A significant improvement in those who produce equol was observed.

Equol is produced by metabolism of daidzein by enteric bacteria. The abilities to produce equol vary between individuals, and the percentage of Japanese who produce equol is reportedly about 50%. That is, about 50% of Japanese are not able to produce equol (non-equol-producing individuals). Such an individual cannot enjoy any useful physiological benefits based on the action of equol even if they ingest soybeans and processed soybean foods. Therefore, in order to attain useful physiological benefits based on the action of equol in a non-equol-producing individual, ingesting equol itself is thought to be effective.

Non-patent Document 1: Morito K, Hirose T, Kinjo J, Hirakawa T, Okawa M, Nohara T, Ogawa S, Inoue S, Muramatsu M, Masamune Y. Interaction of phytoestrogens with estrogen receptors α and β. Biol Pharm Bull 24(4): 351-356, 2001

Non-patent Document 2: Maubach J, Bracke M E, Heyerick A, Depypere H T, Serreyn R F, Mareel M M, Keukeleire D D. Quantitation of soy-derived phytoestrogens in human breast tissue and biological fluids by high-performance liquid chromatography. J Chromatography B 784: 137-144, 2003

Non-patent Document 3: Morton M S, Chan P S F, Cheng C, Blacklock N, Matos-Ferreira A, Abranches-Monteiro L, Correia R, Lloyd S, Griffiths K. Lignans and isoflavonoids in plasma and prostatic fluid in men: Samples from Portugal, Hong Kong, and the United Kingdom. Prostate 32: 122-128, 1997

Non-patent Document 4: Tammy E H, Paul D M, Paul G F, Robert D, Stephen B, Kenneth J, Ray M, Lorraine G O, Kristiina W, Holly M S, Karen J G. Long-term dietary habits affect soy isoflavone metabolism and accumulation in prostatic fluid in caucasian men. J Nutr 135: 1400-1406, 2005.

DISCLOSURE OF THE INVENTION

Problems to be Solved by the Invention

The present inventors have found that fermented soybean hypocotyl obtained by fermenting soybean hypocotyl with an equol-producing microorganism is usable as an equol-containing food material. The fermented soybean hypocotyl contains not only equol but also isoflavone, saponin and like useful soybean-derived components. The fermented soybean hypocotyl achieves such effective physiological effects attributable to these useful components, and therefore is usable as a functional material. The present inventors also found that the fermented soybean hypocotyl is useful as an allergen-reduced material, because the allergens attributable to soybean hypocotyl therein are reduced. The fermented soybean hypocotyl found by the present inventors exhibits physiological effects attributable to the useful components, and is hypoallergenic, and therefore it is usable as a functional food material.

In contrast, the content of the equol in the fermented soybean hypocotyl varies depending on the types of the soybean hypocotyl used for the production of the fermented soybean hypocotyl, types of the equol-producing microorganism, etc., but it is generally about 1 wt. %. If a material with an increased equol content can be provided, various types of equol-containing foods become easily available in response to the diversification of foods. However, the fermented soybean hypocotyl itself is not a known product, and the effective method for efficiently extracting useful component containing equol from fermented soybean hypocotyl has not been found yet.

The fermented soybean hypocotyl, which is an equol-containing substance obtained by the fermentation method describe above, is safer than that obtained by a chemical synthesis method, and suitable for industrial production. However, equol-containing substances obtained by said fermentation method contain metabolites other than equol and various components derived from raw materials remaining therein. Depending on the type of raw material used for fermentation, the equol-containing substance obtained by a fermentation method may contain material that could become an allergen. Therefore, in order to use an equol as an additive for foods or drugs, a technique not only for producing an equol but also purifying the equol-containing substance so as to obtain a highly pure equol is required. However, not many techniques for refining equol have been reported yet, there is a demand for establishing a technique, which is industrially applicable and by which an equol can be purified easily and efficiently.

The fermented soybean hypocotyl has bitterness attributable to soybean hypocotyl or equal. Therefore, sufficient attention must be paid to the flavor of the resulting food when the fermented soybean hypocotyl is used as a food material. The fermented soybean hypocotyl is a novel food material that has not been reported before, and it is unknown which method is effective for improving the flavors thereof. In particular, when the fermented soybean hypocotyl is used as a material for baked confectionaries, it tends to suffer from a deterioration of flavor after being subjected to a baking step. Therefore, exhibiting good flavor is a very difficult technical object.

An object of the present invention is to provide an extract, which contains useful equol-containing components and which is derived from an equol-containing fermented soybean hypocotyl, and a method for producing such an extract. The present invention provides a method for purifying an equol-containing substance to effectively obtain a highly pure equol. Another object of the present invention is to provide a food material obtained by fermenting an equol-containing fermented soybean hypocotyl with an equol-producing microorganism or its extract, in which the flavor is improved. Still another object of the present invention is to provide a food product that contains an equol-containing fermented soybean hypocotyl and exhibits excellent flavor (in particular, baked confectionaries). Still another object of the present invention is to provide various forms of foods that contain an equol-containing fermented soybean hypocotyl or its extract.

Means for Solving the Problem

The present inventors conducted intensive research to achieve the above objects and found that by subjecting an equol-containing fermented soybean hypocotyl to extraction using an ethanol aqueous solution as an extractant, a useful equol-containing component can be efficiently extracted from the fermented soybean hypocotyl. The present inventors further found that by sequentially subjecting the equol-containing fermented soybean hypocotyl to extraction using an ethanol aqueous solution and ethanol, the saponin content that causes an astringent taste, bitterness, an acrid taste and like unpleasant tastes can be reduced, while effectively extracting equol and glycitein.

The present inventors also found that a highly pure equol can be obtained by suspending an equol-containing fermented soybean hypocotyl in an aqueous solution having a pH of 2 to 6, collecting insoluble matter, and then subjecting the resulting insoluble residue to extraction using an ethanol aqueous solution.

The present inventors further found that a highly pure equol can be efficiently and readily obtained by conducting the following Steps (1) to (5):

Step (1): subjecting an equol-containing substance to extraction using an ethanol aqueous solution;
Step (2): subjecting the resulting extract to further extraction using ethanol;
Step (3): subjecting the resulting extract to extraction using hexane;
Step (4): subjecting the resulting insoluble residue to extraction using a mixture of hexane and ether; and Step (5): subjecting the resulting liquid extract to silica gel column chromatography, and obtaining an equol-containing fraction.

The present inventors further found that a highly pure equol can be efficiently and readily obtained by conducting the following Steps (i) to (iii):

(i) subjecting the equol-containing substance to extraction using a specific organic solvent or an aqueous organic solvent, and concentrating the resulting liquid extract;
(ii) subjecting the resulting equol concentrate to silica gel column chromatography, and obtaining an equol-containing fraction; and
(iii) removing the solvent from the resulting equol-containing fraction, and recrystallizing the resulting residue.

The present inventors also found that in a food material obtained by dispersing an equol-containing fermented soybean hypocotyl or its extract in cacao mass, the bitterness attributable to the equol-containing fermented soybean hypocotyl can be reduced and excellent flavor can be exhibited. The present inventors also found that the food material is usable in various foods, including baked confectionaries, without adversely affecting the flavor.

The present inventors successfully developed various food products into which an equol-containing fermented soybean hypocotyl or its extract is added.

The present invention has been accomplished based on these findings and some improvement added thereto.

The present invention provides a method for obtaining an equol-containing extract.

Item 1-1. A method for producing an equol-containing extract comprising Step I-1:
subjecting an equol-containing fermented soybean hypocotyl to extraction using an ethanol aqueous solution as an extractant; and collecting the resulting liquid extract.

Item 1-2. The method according to Item 1-1, which further comprises Step I-2:
removing the extractant from the liquid extract obtained in Step I-1;
conducting extraction using ethanol as an extractant; and collecting the liquid extract.

Item 1-3. The method according to Item 1-1, wherein the ethanol aqueous solution used in Step I-1 has an ethanol concentration of 20 to 98 wt. %.

Item 1-4. The method according to any one of Items 1-1 to 1-3, wherein the equol-containing fermented soybean hypocotyl is obtained by fermenting a soybean hypocotyl with an equol-producing microorganism.

Item 1-5. A method for producing an equol-containing extract from equol-containing fermented soybean hypocotyl, comprising Steps II-1 and II-2;
Step II-1 of suspending the equol-containing fermented soybean hypocotyl in water, adding an acid so as to adjust the pH to 2 to 6, and collecting insoluble residue; and
Step II-2 of subjecting the insoluble residue obtained in Step II-1 to extraction using an ethanol aqueous solution as an extractant, and then collecting the resulting liquid extract.

Item 1-6. The method of Item 1-5, wherein the acid used in Step II-1 is acetic acid.

The present invention provides the following equol-containing extracts.

Item 2-1. An equol-containing extract obtained by subjecting an equol-containing fermented soybean hypocotyl to extraction using an ethanol aqueous solution as an extractant.

Item 2-2. An equol-containing extract obtained by sequentially subjecting an equol-containing fermented soybean hypocotyl to extraction using an ethanol aqueous solution and ethanol.

Item 2-3. An equol-containing extract obtained by a method according to any one of Items 1-1 to 1-6.

The present invention provides the following methods for refining an equol.

Item 3-1. A method for purifying an equol-containing substance to obtain equol comprising Steps 1-1 to 1-5 below:

Step 1-1 of subjecting an equol-containing substance to extraction using an ethanol aqueous solution as an extractant, and collecting the resulting liquid extract;

Step 1-2 of removing the solvent from the liquid extract obtained in Step 1-1, subjecting the resulting residue to extraction using ethanol as an extractant, and then collecting the liquid extract;

Step 1-3 of removing the solvent from the liquid extract obtained in Step 1-2, suspending the resulting residue in hexane, and then collecting an insoluble residue;

Step 1-4 of subjecting the insoluble residue obtained in Step 1-3 to extraction using a mixture of hexane and ether as an extractant, and then collecting the liquid extract; and Step 1-5 of subjecting the liquid extract obtained in Step 1-4 to silica gel column chromatography, and obtaining an equol-containing fraction.

Item 3-2. The method according to Item 3-1, wherein the equol-containing substance is a fermented material that contains an equol.

Item 3-3. The method according to Item 3-2, wherein the fermented material that contains an equol is an equol-containing fermented soybean hypocotyl material obtained by fermenting a soybean hypocotyl with an equol-producing microorganism.

Item 3-4. The method according to any one of Items 3-1 to 3-3, wherein the extractant used in Step 1-4 is a mixture of hexane and diethyl ether.

Item 3-5. The method according to any one of Items 3-1 to 3-4, wherein the extractant used in Step 1-4 is a mixture of hexane and ether having a volume ratio of 10:90 to 20:80.

Item 3-6. The method according to any one of Items 3-1 to 3-5, wherein the ethanol concentration of the ethanol aqueous solution used in Step 1-1 is 20 to 98 vol. %.

Item 3-7. A method for purifying an equol-containing substance comprising Steps 2-1 to 2-3 of:

Step 2-1 of subjecting the equol-containing substance to extraction using, as an extractant, an organic solvent or an aqueous organic solvent of at least one member selected from the group consisting of ethyl acetate, alcohol, acetone, dioxane, acetonitrile, diethyl ether, and toluene, and collecting the resulting liquid extract;

Step 2-2 of subjecting the liquid extract obtained in Step 2-1 to silica gel column chromatography, and obtaining an equol-containing fraction; and Step 2-3 of removing the solvent from the equol-containing fraction obtained in Step 2-2, recrystallizing the resulting residue, and collecting the deposited crystals.

Item 3-8. The method according to Item 3-7, wherein Step 2-3 comprises a recrystallization using an aqueous alcohol solution after the recrystallization using a mixture of ethyl acetate and hexane.

The present invention provides the following food materials, and foods using such food materials.

Item 4-1. A food material obtained by dispersing an equol-containing fermented soybean hypocotyl or its extract in cacao mass.

Item 4-2. The food material according to Item 4-1, wherein the food material contains 10 to 2000 parts by weight of cacao mass per 100 parts by weight of equol-containing fermented soybean hypocotyl or its extract.

Item 4-3. The food material according to Item 4-1 or 4-2, wherein the equol-containing fermented soybean hypocotyl is obtained by fermenting soybean hypocotyl with an equol-producing microorganism.

Item 4-4. The food material according to Item 4-3, wherein the equol-producing microorganism is a microorganism that can metabolize at least one daidzein compound selected from the group consisting of daidzein glycoside, daidzein, and dihydrodaidzein to produce equol.

Item 4-5. The food material according to any one of Items 4-1 to 4-4, which takes a granular form, a chip form, or a plate-like form.

Item 4-6. An equol-containing food comprising a food material of any one of Items 4-1 to 4-5.

Item 4-7. The equol-containing food according to Item 4-6, which is a baked confectionary.

The present invention provides the following foods:

Item 5-1. A food comprising an equol-containing fermented soybean hypocotyl or its extract.

Item 5-2. A beverage comprising an equol-containing fermented soybean hypocotyl or its extract.

Item 5-3. A dietary supplement comprising an equol-containing fermented soybean hypocotyl or its extract.

Item 5-4. A creamy food comprising an equol-containing fermented soybean hypocotyl or its extract.

Item 5-5. A dessert comprising an equol-containing fermented soybean hypocotyl or its extract.

Item 5-6. A snack comprising an equol-containing fermented soybean hypocotyl or its extract.

Item 5-7. A seasoning comprising an equol-containing fermented soybean hypocotyl or its extract.

Item 5-8. A retort-packed food comprising an equol-containing fermented soybean hypocotyl or its extract.

Item 5-9. A processed meat product comprising an equol-containing fermented soybean hypocotyl or its extract.

Item 5-10. A fish paste comprising an equol-containing fermented soybean hypocotyl or its extract.

Item 5-11. A processed egg product comprising an equol-containing fermented soybean hypocotyl or its extract.

Item 5-12. A canned food comprising an equol-containing fermented soybean hypocotyl or its extract.

Item 5-13. A bread product comprising an equol-containing fermented soybean hypocotyl or its extract.

Item 5-14. A frozen dessert comprising an equol-containing fermented soybean hypocotyl or its extract.

Item 5-15. A processed soybean food comprising an equol-containing fermented soybean hypocotyl or its extract.

Item 5-16. A cooked rice product comprising an equol-containing fermented soybean hypocotyl or its extract.

Item 5-17. A soup comprising an equol-containing fermented soybean hypocotyl or its extract.

Item 5-18. A food according to any one of Items 5-1 to 5-18, wherein the equol-containing fermented soybean hypocotyl is obtained by fermenting a soybean hypocotyl with an equol-producing microorganism.

Item 5-19. The food according to Item 5-18, wherein the microorganism has an ability to metabolize at least one daidzein compound selected from the group consisting of daidzein glycoside, daidzein, and dihydrodaidzein to produce equol.

Effects of the Invention

The method for producing an equol-containing extract of the present invention can produce an equol-containing extract that is useful as a functional food material by effectively extracting useful components containing equol from the equol-containing fermented soybean hypocotyl. By sequentially subjecting an equol-containing fermented soybean hypocotyl to extraction using an ethanol aqueous solution and ethanol, an equol-containing extract that contains a high concentration of equol and glycitein, with a reduced amount of saponin that causes an unpleasant taste is obtainable. Accordingly, the equol-containing extract can be added to foods without adversely affecting the taste.

The purification method of the present invention makes it possible to readily and efficiently obtain a highly pure equol from the equol-containing substance. In particular, the purification method of the present invention makes it possible to highly pure equol even when the equol-containing substance contains isoflavones whose structure is similar to that of the equol by removing these isoflavones. Accordingly, the purification method of the present invention can be suitably employed in obtaining equol from an equol-containing fermented material that contains a large proportion of isoflavones.

Furthermore, the food material obtained by dispersing an equol-containing fermented soybean hypocotyl or its extract into cacao mass has reduced bitterness and exhibits excellent flavor, although it contains an equol-containing fermented soybean hypocotyl or its extract. The food material of the present invention can be used in various foods without adversely affecting the flavor. When conventional food material is added to a baked confectionary in a granular form or a chip form, the components in the food material tend to diffuse into the entire baked confectionary in the baking step, and a desirable flavor may not be obtained. In the food material of the present invention, the equol-containing fermented soybean hypocotyl is covered with cacao mass. Therefore, even when the food material of the present invention is added to a baked confectionary in a granular form or a chip form, diffusion of the effective components within the food material can be suppressed and a desirable flavor can be obtained.

The useful physiological benefits of the food of the present invention can be enjoyed based on the useful physiological activity of the equol-containing fermented soybean hypocotyl or its extract.

The equol-containing fermented soybean hypocotyl or its extract has reduced soybean hypocotyl-derived allergens, and therefore the food material and various foods of the present invention can be safely taken by or administered to people suffering from soybean allergy.

BEST MODE FOR CARRYING OUT THE INVENTION

The following details the present invention.
1. Production Method for Equol-Containing Extract
The present invention provides a method for producing an equol-containing extract using an equol-containing fermented soybean hypocotyl as a material. The production method for the equol-containing extract of the present invention is divided into the following Production Methods I and II. The following details an equol-containing fermented soybean hypocotyl used as a material of the method of the present invention, and describes in detail Production Methods I and II.
Equol-Containing Fermented Soybean Hypocotyl
In the production method for the equol-containing extract according to the present invention, an equol-containing fermented soybean hypocotyl is used as a raw material. The following describes an equol-containing fermented soybean hypocotyl.

An equol-containing fermented soybean hypocotyl is a kind of a fermented soybean hypocotyl produced by fermenting a soybean hypocotyl using an equol-producing microorganism.

The equol-producing microorganism used for the production of the equol-containing fermented soybean hypocotyl is selected from microorganisms having the ability (metabolic activity) to produce equol by metabolizing at least one daidzein compound selected from the group consisting of daidzein glycosides, daidzein, and dihydrodaidzein. Examples of the daidzein glycosides here include daidzin, malonyldaidzin, and acetyldaidzin.

The equol-producing microorganism is not limited and may be any microorganism having the foregoing ability. For example, any publicly known microorganisms, or any microorganisms obtained by a general screening method, may be used. It is known that such equol-producing microorganisms exist in the microorganisms belonging to *Lactococcus*, such as *Lactococcus garvieae*; microorganisms belonging to *Streptococcus*, such as *Streptococcus intermedius* or *Streptococcus constellatus*; or microorganisms belonging to *Bacteroides* such as *Bacteroides ovatus*. Among various kinds of equol-producing microorganism, the present invention prefers lactic acid bacteria belonging to *Lactococcus* or *Streptococcus*, further prefers lactic acid bacteria belonging to *Lactococcus*, and in particular, lactic acid bacteria belonging to *Lactococcus garvieae*. The equol-producing microorganisms may be isolated from, for example, human feces, based on the index of the existence of an equol-producing property. The inventors of the present invention deposited some identified bacterium that had been isolated from human feces; namely, *Lactococcus* 20-92 (FERN BP-10036), *Streptococcus* E-23-17 (FERN BP-6436), *Streptococcus* A6G225 (FERN BP-6437), and *Bacteroides* E-23-15 (FERN BP-6435), that are available to be used as the equol-producing microorganisms. Among these, the present invention particularly prefers *Lactococcus* 20-92.

The equol-containing fermented soybean hypocotyl is produced using soybean hypocotyl as a fermenting material. The soybean hypocotyl designates a part corresponding to the plumule or the radicle on the germination of soybean, and is known to contain a large amount of daidzein compounds such as daidzein glycosides or daidzein. The soybean hypocotyl used in the present invention is not limited by the producing district of soybean or whether processed or unprocessed, unless the daidzein compounds inside are not significantly lost. For example, the equol-containing fermented soybean hypocotyl may be a raw hypocotyl, or may be one isolated from heated, dried or steam-boiled soybean, or one obtained by heating, drying or steam-boiling hypocotyl that is isolated from unprocessed soybean. Further, the soybean hypocotyl may be processed by degreasing or deproteinization. The form of the soybean hypocotyl is not particularly limited, and may be in the form of powder, chunks, or pulverized or fragmentized grains. Powdery soybean hypocotyl is particularly preferable because of its efficient equol production. The fermentation of soybean hypocotyl is carried out by first adjusting the water content of the soybean hypocotyl by adding an appropriate amount of water, and then inoculating the equol-producing microorganism to the hypocotyl.

The amount of water added to the soybean hypocotyl is adjusted depending on the type of equol-producing microorganism or the type of fermenter. The ratio of water to the soybean hypocotyl in the beginning of fermentation is 400 to 4,000 parts by weight, preferably 500 to 2,000 parts by weight, further preferably 600 to 1,000 parts by weight, based on 100 parts by weight (dry weight) of the soybean hypocotyl.

Further, if necessary, some additives may be added to the soybean hypocotyl as the raw material in the fermentation to improve the fermentation efficiency or flavor of the product. Examples of the additives include nitrogen sources such as a yeast extract, polypeptone, or a meat extract; carbon sources such as glucose or sucrose; inorganic salts such as phosphate, carbonate or hydrosulfate; vitamins; and nutritional components such as amino acid. Particularly, when using an equol-producing microorganism for converting arginine into ornithine (hereinafter referred to as an "ornithine/equol-producing microorganism"), arginine is added to the soybean hypocotyl before fermentation so that the fermented substance contains ornithine. In this case, the amount of arginine is, for example, about 0.5 to 3 parts by weight, based on 100 parts by weight (dry weight) of the soybean hypocotyl. The ornithine/equol-producing microorganism may be obtained by a publicly-known screening method using an index of the equol-producing ability and the conversion ability from arginine into ornithine. The ornithine/equol-producing microorganism may be selected from the group of *Lactococcus garvieae*, typified by *Lactococcus* 20-92 (FERN BP-10036).

Further, the pH of the fermenting material (a soybean hypocotyl containing substance) is not particularly limited within a range for the equol-producing microorganism to grow; however, to secure excellent proliferation of the equol-producing microorganism, the pH of the fermenting material preferably falls to within about 6 to 7, more preferably about 6.3 to 6.8.

Further, isoflavone containing the above-mentioned daidzein compounds may be added to the fermenting material (a soybean hypocotyl containing substance). Such inclusion of isoflavone in the fermenting material increases the equol content of the fermented soybean hypocotyl, thereby improving the usability of the fermented soybean hypocotyl.

The fermentation of the soybean hypocotyl is carried out under appropriate conditions according to the growing characteristic of the equol-producing microorganisms. For example, when the equol-producing microorganisms listed above are used, the fermentation of the soybean hypocotyl is carried out under anaerobic conditions.

The fermentation temperature is not limited within an appropriate range for the equol-producing microorganism to grow. The temperature is generally 20 to 40° C., preferably 35 to 40° C., and more preferably 36 to 38° C.

The fermentation time is determined depending on the desired production amount of equol, the residual amount of daidzein compounds, the type of the equol-producing microorganism or the like. The fermentation time is generally 1 to 10 days, preferably 2 to 7 days, and further preferably 3 to 5 days.

In the fermented soybean hypocotyl obtained through the fermentation under the foregoing conditions, the produced equol is accumulated, and thereby the useful physiologic activity of equol can be expressed. The equol content in the fermented soybean hypocotyl varies depending on the type of the equol-producing microorganism or fermentation conditions. The equol content in the fermented soybean hypocotyl is generally 1 to 20 mg, preferably 2 to 12 mg, and more preferably 5 to 8 mg, per gram (dry weight) of the fermented soybean hypocotyl.

Apart from equol, the equol-containing fermented soybean hypocotyl also contains various isoflavones such as daidzein compounds including daidzin, malonyldaidzin, acetyldaidzin, daidzein, or dihydrodaidzein (these components are referred to as "daidzein compounds", hereinafter); genistein compounds including malonylgenistin, acetylgenistin, genistein, dihydrogenistein (these components are referred to as "genistein compounds", hereinafter); or glycitein compounds including glycitin, malonylglycitin, acetylglycitin, glycitein, dihydroglycitein (these components are referred to as "glycitein compounds" hereafter). The isoflavones also express the useful physiologic activities. The content of each isoflavone (incl. equol) in the fermented soybean hypocotyl is generally 5 to 20 mg, preferably 5 to 15 mg, and more preferably 8 to 15 mg, per gram (dry weight) of the equol-containing fermented soybean hypocotyl.

Further, the equol-containing fermented soybean hypocotyl also differs from general soybean hypocotyls in terms of the composition of isoflavones other than equol. Particularly, the total content of genistein compounds in the equol-containing fermented soybean hypocotyl is preferably not more than 15 wt. %, and more preferably not more than 12 wt. %. With such a low genistein compound content, the equol-containing fermented soybean hypocotyl is more advantageous than the unfermented soybean hypocotyl in terms of the composition of isoflavones. Note that genistein compounds are kinds of isoflavone and are chemicals suspected of endocrine disruption, and there is a demand for the reduction in genistein compounds concentrations in food (Young H J, Jodi F, Kimberly F A, Daniel R D, William G H. Effects of dietary daidzein and its metabolite, equol, at physiological concentrations on the growth of estrogen-dependent human breast cancer (MCF-7) tumors implanted in ovariectomized athymic mice. See Carcinogenesis 127(4):856-863, 2006).

The following is an isoflavone composition example of the equol-containing fermented soybean hypocotyl (the unit "mg" represents the total amount of each isoflavone per gram (dry weight) of the fermented soybean hypocotyl).

Equol: 1 to 20 mg, preferably 2 to 12 mg
Daidzein compounds: 0.1 to 30 mg, preferably 0.1 to 1.5 m
Genistein compounds: 0.05 to 2.5 mg, preferably 0.05 to 2 mg
Glycitein compounds: 0.1 to 4 mg, preferably 2 to 3.5 mg.

The following is a composition ratio example of the isoflavones in the equol-containing fermented soybean hypocotyl (the unit "wt. %" represents a ratio relative to the total amount of isoflavones in the equol-containing fermented soybean hypocotyl).

Equol: 30 to 75 wt. %, preferably 40 to 70 wt. %, more preferably 45 to 70 wt. %
Daidzein compounds: 1 to 20 wt. %, preferably 2 to 15 wt. %, more preferably 4 to 12 wt. %
Genistein compounds: 0.1 to 20 wt. %, preferably 1 to 15 wt. %, more preferably 1 to 10 wt. %
Glycitein compounds: 10 to 50 wt. %, preferably 15 to 35 wt. %, more preferably 25 to 35 wt. %.

Since this equol-containing fermented soybean hypocotyl has a particular isoflavone composition that is not found in any prior art, it can be defined as an isoflavone-containing substance specified by the foregoing isoflavone composition.

*Lactococcus* 20-92 (FERM BP-10036) is particularly preferred as an equol-producing microorganism in the production of the equol-containing fermented soybean hypocotyl having the foregoing isoflavone composition.

The equol-containing fermented soybean hypocotyl also contains saponin derived from the soybean hypocotyl. The equol-containing fermented soybean hypocotyl generally contains saponin in an amount of 10 to 80 mg, preferably 20 to 50 mg, and more preferably 30 to 40 mg, per gram (in dry weight) of the equol-containing fermented soybean hypocotyl.

Further, as described above, ornithine is contained in the fermented soybean hypocotyl produced from fermentation with an ornithine/equol-producing microorganism after adding arginine to soybean hypocotyl. The ornithine content of the equol-containing fermented soybean hypocotyl is 5 to 20 mg, preferably 8 to 15 mg, and more preferably 9 to 12 mg, per gram (dry weight) of the equol-containing fermented soybean hypocotyl.

The equol-containing fermented soybean hypocotyl obtained through fermentation under the foregoing conditions may be used directly after fermentation as a material of the production method of the present invention, or may be dried after fermentation to be a dry solid before being used as the material of the production method of the present invention.

Further, the equol-containing fermented soybean hypocotyl obtained through fermentation under the foregoing conditions may be subjected to preprocessing, such as defatting, before the following Step I-1. The defatting can be performed by a method using hexane as an extractant.

1-1. Production Method I

In Production Method I, the production of the equol-containing extract is accomplished by carrying out Step I-1, which is described below.

Step I-1

Production Method I for producing the equol-containing extract comprises a Step I-1 of extracting an equol-containing fermented soybean hypocotyl using an aqueous ethanol solution as an extractant, and collecting liquid extract.

The ethanol concentration of the aqueous ethanol solution (a mixed solution of ethanol and water) used in Step I-1 is generally 20 to 98 vol. %, preferably 45 to 95 vol. %, and more preferably 65 to 85 vol. %. By meeting this concentration range, it becomes possible to extract useful components including equol from the equol-containing fermented soybean hypocotyl.

The extraction in Step I-1 uses an aqueous ethanol solution in an amount of, for example, 1 to 1000 parts by weight, preferably 2 to 500 parts by weight, more preferably 5 to 20 parts by weight, per part by weight (dry weight) of the equol-containing fermented soybean hypocotyl.

The Step I-1 extraction conditions are not particularly limited, and a warm or cold dipping extraction method, percolation method or the like may be used. More specifically, an aqueous ethanol solution is added to the equol-containing fermented soybean hypocotyl, and the mixture is allowed to stand or stirred for at least one minute at room temperature, preferably for 5 minutes to 48 hours at room temperature.

After such extraction, the liquid extract is isolated to obtain an equol-containing extract. The collection of the liquid extract is performed by a publicly-known method, such as filtration or centrifugation.

The liquid extract thus isolated in Step I-1 contains useful components including equol and glyciteins, and the amount of oil is less than that in the equol-containing fermented soybean hypocotyl. The liquid extract thus obtained in Step I-1 may be directly incorporated into a food or medicine as a liquid equol-containing extract, or may be solidified by removing the extractant before incorporated into a food or medicine. Further, the liquid extract thus obtained in Step I-1, either in the form of a liquid or a solid equol-containing extract, may be subjected to equol refining.

The liquid extract isolated in Step I-1 contains equol, glyciteins, and saponin, which can cause unpleasant astringency, bitterness, or acridness. It is thus preferable to subject the liquid extract isolated in Step I-1 to the following Step I-2 so as to remove saponin and increase the concentration of the useful components, including equol.

Step I-2

Step I-2 comprises removing the extractant from the liquid extract obtained in Step I-1, carrying out another extraction using ethanol as an extractant, and collecting an extract.

In Step I-2, the removal of the extractant from the extract obtained in Step I-1 can be performed by a publicly-known method such as drying.

The solid obtained by the removal of the extractant from the extract obtained in Step I-1 (this solid may be hereinafter referred to as "Solid Material") is subjected to extraction using ethanol as an extractant. The ethanol used as an extractant in Step I-2 may be water-free ethanol that however may inevitably contain vapor.

The extraction in Step I-2 uses, for example, 1-1000 parts by weight, preferably 5-500 parts by weight, and more preferably 5-20 parts by weight of ethanol, per part by weight (dry weight) of the solid material.

The condition in Step I-2 extraction is not particularly limited, and may be performed by a warm or cold dipping extraction method, percolation method or the like. More specifically, ethanol is added to the solid material and the mixture is allowed to stand or stirred for at least one minute at room temperature, preferably for 5 minutes to 48 hours at room temperature. The Step I-2 extraction may be combined with supersonic treatment to increase the equol collection rate.

After such extraction, the extract is isolated to obtain an equol-containing extract. The collection of the extract is performed by a publicly-known method, such as filtration or centrifugation.

The extract thus isolated in Step I-2 contains a greater amount of useful components including equol and glyciteins, and a reduced amount of saponin. The usefulness of this extract is therefore greater than the extract obtained in Step I-1. The extract thus obtained in Step I-2 may be directly incorporated into a food or medicine as a liquid equol-containing extract, or may be solidified by removing the extractant before being incorporated into a food or medicine. The extract thus obtained in Step I-2, either in the form of a liquid or a solid equol-containing extract, may be subjected to equol refining. Note that, in order to improve the conservation stability of the equol-containing extract, it is more preferable to solidify the liquid extract by removing the extractant.

Composition and Use of Equol-Containing Extract Obtained by Production Method I

The equol content of the liquid extract obtained in Step I-1 or Step I-2 is 0.2 to 40 wt. %, preferably 0.4 to 24 wt. %, and more preferably 1 to 16 wt. %, based on the total amount of a dry solid product (100 wt. %). The glycitein content of the liquid extract obtained in Step I-1 or Step I-2 is 0.01 to 8 wt. %, preferably 0.08 to 5 wt. %, and more preferably 0.2 to 3 wt. %, based on the total amount of a dry solid product.

The equol-containing extract obtained in Step I-1 or Step I-2 contains equol at a high concentration, and expresses the useful activities based on equol. More specifically, the equol-containing extract obtained in Step I-1 or Step I-2 has an effect of preventing or treating various diseases or symptoms including menopausal disorders, osteoporosis, prostatic hypertrophy, and metabolic syndrome; or for blood cholesterol level reduction, skin-whitening, pimples, intestinal control, obesity, and diuresis. Since the useful activities are thus expressed, the equol-containing extract obtained in Step I-1 or Step I-2 may be incorporated into food or medicines.

When used for a foodstuff, the equol-containing extract obtained in Step I-1 or Step I-2 is often incorporated into beverages, granules, fine granules, capsules, tablets, powder, dairy products, gums, gummy candies, puddings, bars, and other various dry foods. The food containing the equol-containing extract may be used as a general food product, and also as a specified health food, nutritional supplement, functional food, invalid food or the like. Particularly, any food containing the fermented soybean hypocotyl of the present invention is useful as a nutritional supplement. Note that the details of foodstuffs containing the equol-containing extracts obtained in Step I-1 or Step I-2 are described later.

When the equol-containing extract obtained in Step I-1 or Step I-2 is incorporated into a foodstuff, the proportion of the equol-containing extract in the food varies depending on the type of food, the equol content, the age and sex of the consumer, the desired effect etc. Typically, the total amount (dry weight base) of the equol-containing extract is 0.1 to 90 g, per 100 g of food.

When used for a medicinal product, the equol-containing extract obtained in Step I-1 or Step I-2 is often incorporated into tablets, pills, powder, liquids, suspensions, emulsions, granules, capsules, or suppositories. Such a medicinal product containing the equol-containing extract has an effect of preventing or treating various diseases or symptoms including menopausal disorders (indefinite menopausal complaints, osteoporosis, hyperlipidemia), osteoporosis, prostatic hypertrophy, and metabolic syndrome; or for blood cholesterol level reduction, skin-whitening, pimples, intestinal control, obesity, and diuresis. Particularly, the medicinal product containing the equol-containing extract is suitable for the prevention or treatment of indefinite complaint or post-menopausal symptoms (e.g. osteoporosis, menopausal disorder) of middle-aged women.

The dose of the medicinal product containing the equol-containing extract obtained in Step I-1 or Step I-2 cannot be uniformly defined, as it varies depending on the equol content in the equol-containing extract, age, weight, symptom of the object or the dosage number. The adult dosage per day typically corresponds to the amount (dry weight) of the equol-containing extract from 1 to 2000 mg, preferably 5 to 1000 mg, and more preferably 40 to 50 mg. It is particularly preferable to determine the dose of the equol-containing extract so that 2 to 30 mg of equol is administered per day.

1-2. Production Method II

Production Method II produces an equol-containing liquid extract by carrying out the following Step II-1 and Step III-2. The following details Production Method II.

Step II-1

Production Method II first suspends an equol-containing fermented soybean hypocotyl in water, adds an acid to the suspension to adjust the pH to a range of 2 to 6, and isolates an insoluble residue (Step II-1). In other words, in Step II-1, an equol-containing fermented soybean hypocotyl is suspended in an aqueous solution (pH 2 to 6) containing an acid, thereafter collecting an insoluble residue.

In Step II-1, an equol-containing fermented soybean hypocotyl is suspended in water, and an acid is added to the suspension to adjust the pH to a range of from 2 to 6.

The acid used in Step II-1 may be an organic acid or an inorganic acid. The organic acid is not limited as long as it is adjustable to the foregoing pH range. Examples of the organic acid include citric acids, L-tartaric acids, fumaric acids, L-ascorbic acids, gluconic acids, acetic acids, lactic acids, DL-malic acids, oxalic acids, formic acids, propionic acids, butanoic acids, and methanesulfone acids. Similarly, the inorganic acid is not limited as long as it is adjustable to the foregoing pH range. Examples of the inorganic acid include hydrochloric acids, sulfuric acids, nitric acids and phosphoric acids. Among them, acetic acids, hydrochloric acids and sulfuric acids are preferred.

In Step II-1, the amount of water in which the equol-containing fermented soybean hypocotyl is suspended is, for example, 3 to 30 parts by weight, more preferably 5 to 20 parts by weight, per part by weight (dry weight) of an equol-containing fermented soybean hypocotyl.

In Step II-1, an equol-containing fermented soybean hypocotyl is mixed in an aqueous solution 2 to 6 in pH, and the solution is stirred or allowed to stand at room temperature for at least 30 minutes, more preferably 2 to 24 hours.

Such treatment leaves equol as a part of the insoluble residue, and the equol can be obtained by collecting the insoluble residue using a publicly-known method such as filtration or centrifugation.

The insoluble residue thus obtained in Step II-1 is then subjected to the following Step II-2.

Step II-2

The insoluble residue thus obtained in Step II-1 is subjected to another extraction using an aqueous ethanol solution as an extractant. The resulting liquid extract is isolated (Step II-2).

The insoluble residue obtained in Step II-1 may be subjected to Step II-2, regardless of whether it is a dry product or a wet product. However, when the insoluble residue is a wet product, it is preferable to adjust the water content of the aqueous ethanol solution (described later) in consideration of the measured water content of the insoluble matter.

The ethanol concentration of the aqueous ethanol solution (a mixed solution of ethanol and water) used in Step II-2 is, for example, 50 to 95 vol. %, more preferably 70 to 90 vol. %. With this concentration range, the equol extraction obtained from the insoluble residue in Step II-2 can be efficiently performed.

The extraction in Step II-2 uses an aqueous ethanol solution in an amount of, for example, 2 to 30 parts by weight, more preferably 4 to 10 parts by weight, per part by weight (dry weight) of the insoluble residue obtained in Step II-1.

The condition in the extraction in Step II-2 is not particularly limited, and the warm or cold dipping extraction method, percolation method or the like may be used. More specifically, an aqueous ethanol solution is added to the insoluble residue obtained in Step II-1, and the mixture is allowed to stand or stirred for at least 30 minutes at room temperature, preferably 1 minute to 50 hours at room temperature.

After such extraction, the liquid extract is isolated to obtain an equol-containing fraction. The collection of the extract is performed by a publicly-known method such as filtration or centrifugation.

Because of the inclusion of concentrated equol, the liquid extract thus isolated in the Step II-2 contains equol at a high concentration and useful components such as glysitein compounds, the extract is more useful than the equol-containing fermented soybean hypocotyl. The liquid extract obtained in Step II-2 may be directly incorporated into a food or medicine as a liquid equol-containing extract, or may be processed into powder by removing the extractant before incorporated into a food or medicine. The liquid extract thus obtained in Step II-2, either in the form of a liquid or a solid equol-containing extract, may be subjected to equol refining. Note that, in order to improve the conservation stability of the equol-containing extract, it is more preferable to solidify the liquid extract by removing the extractant.

The removal of the extractant from the liquid extract obtained in Step II-2 may be performed under the same conditions as in Step I-2 of Production Method 1; however, the removal is preferably performed by spray-drying.

Composition and Use of Equol-Containing Extract Obtained by Production Method II By drying the liquid extract obtained in Method II (the liquid extract obtained in the foregoing Step II-2), it is possible to isolate equol with a collection rate of 90% or greater. Thus obtained is equol-containing powder that contains equol ten times greater than the equol in an equol-containing fermented soybean hypocotyl. With this high equol content, the equol-containing powder more effectively expresses the useful activities derived from equol. The purpose or method of use of the equol-containing powder obtained in Method II is the same as that of the equol-containing powder obtained in Method I.

2. Equol Purification Method

The present invention also provides a method for purifying an equol-containing substance to obtain equol. The equol purification method of the present invention is divided into the following Purification Methods 1 and 2. The following details an equol-containing fermented soybean hypocotyl to be refined by the purification method of the present invention and describes in detail Purification Methods 1 and 2.

Equol-Containing Substance

In the purification method of the present invention, the equol-containing substance to be subjected to the purification process is not limited as long as it contains equol. For example, the equol-containing substance used for the method may be a reaction product containing equol generated by chemical synthesis, or an equol-containing fermented substance produced by fermentation. The equol-containing fermented substance obtained through fermentation contains many kinds of isoflavone similar in structure to equol. However, since the method of the present invention can advantageously separate equol from isoflavone in a efficient manner, an equol-containing fermented substance is suitable for an equol-containing substance for the purification method of the present invention.

The following explains an equol-containing fermented substance.

The equol-containing fermented substance was produced through a publicly-known fermentation method using an equol-producing microorganism. More specifically, a microorganism with the ability (metabolic activity) to produce equol by metabolizing at least one daidzein compound selected from the group consisting of daidzein glycosides, daidzein, and dihydrodaidzein, is inoculated in a fermenting material (material to be subjected to the fermentation) containing the daidzeins. The sample is then fermented (cultured) under the conditions suitable to grow the microorganism. The resulting fermented substance contains equol.

The equol-producing microorganism is selected from the list of "Equol-Containing Fermented Soybean Hypocotyl" in the section "1. Production Method for Equol-Containing Extract".

The fermenting material containing daidzein compounds is not limited by other factors; however, the material is preferably approved for its safety as a food material. Examples of the fermenting material containing daidzein compounds include soybeans, soybean hypocotyl, soybean hypocotyl extract, tofu, deep-fried tofu, soy milk, fermented soybeans, soy sauce, bean paste, a tempeh, and a red clove or its extract, alfalfa or its extract. A suitable fermenting material containing daidzein compounds is a soybean hypocotyl because of its high daidzein content.

Further, an isoflavone containing any of above-described daidzein compound may be added in advance to the fermenting material containing daidzein compounds. With this extra addition of isoflavone to the fermenting material, the equol content of the resulting fermented substance increases.

Further, as required, some additives may be used in the fermenting material containing daidzein compounds to improve fermentation efficiency etc. Examples of the additives include nitrogen sources such as a yeast extract, poly peptone, or a meat extract; carbon sources such as glucose or sucrose; inorganic salts such as phosphate, carbonate or hydrosulfate; vitamins; and nutritional components such as amino acid.

Various fermentation conditions including water content, time, temperature, atmosphere in the production of an equol-containing fermented substance are determined depending on the type of the equol-producing microorganism, the type of the fermenting material, the production amount of equol, the residual daidzein compound amount, or the like.

For the equol-containing substance used for the purification method of the present invention, the equol-containing fermented soybean hypocotyl described in the section "1. Production Method for Equol-Containing Extract" is particularly preferable.

2-1. Purification Method 1

The Purification Method 1 refines equol by carrying out the following Steps 1-1 to 1-5.

Step 1-1

The purification method of the present invention carries out extraction with respect to an equol-containing substance using an aqueous ethanol solution as an extractant, and then collects the resulting liquid extract (Step 1-1).

A typical ethanol concentration of the aqueous ethanol solution used in Step 1-1 is 20 to 98 vol. %, preferably 45 to 95 vol. %, and more preferably 45 to 60 vol. %. Ensuring this ethanol concentration, it is possible to efficiently extract equol from the equol-containing substance.

The extraction in Step 1-1 uses an aqueous ethanol solution in an amount of, for example, 1 to 1000 parts by weight, preferably 2 to 500 parts by weight, more preferably 5 to 20 parts by weight, per part by weight (dry weight) of the equol-containing substance.

The conditions in the extraction in Step 1-1 are not particularly limited, and a warm or cold dipping extraction method, percolation method or the like may be used. More specifically, an aqueous ethanol solution is added to the equol-containing substance, and the mixture is allowed to stand or stirred for at least one minute at room temperature, more preferably 5 minutes to 48 hours at room temperature.

After such extraction, the liquid extract is isolated to obtain an equol-containing fraction. The collection of the liquid extract is performed by a publicly-known method such as filtration or centrifugation.

The liquid extract thus isolated in Step 1-1 contains a reduced amount of oil in the equol-containing substance, and isoflavone including glycitein compounds and saponin, as well as equol.

The liquid extract thus obtained in Step 1-1 is subjected to the following Step 1-2.

Step 1-2

After removing the extractant from the liquid extract obtained in Step 1-1, the residue is subjected to extraction using ethanol as an extractant, and the liquid extract is isolated (Step 1-2).

In Step 1-2, the removal of the extractant from the liquid extract obtained in Step 1-1, and another extraction of the thus-obtained residue using an ethanol, and the collection of the liquid extract are carried out in the same conditions as those of Step I-2 of Production Method I in the section "1. Production Method for Equol-Containing Extract".

The liquid extract collected in Step 1-2 contains a reduced amount of saponin, and contains isoflavone including glycitein compounds, as well as equol. The liquid extract thus obtained in Step 1-2 is subjected to the following Step 1-3.

Step 1-3

After removing the extractant from the liquid extract obtained in Step 1-2, the residue is suspended in hexane to isolate an insoluble matter (Step 1-3).

In Step 1-3, the removal of extractant from the liquid extract obtained in Step 1-2 may be performed by a publicly-known method such as distillation under reduced pressure, drying or the like.

The extractant is removed from the liquid extract obtained in Step 1-2, and hexane is added to the residue (hereinafter occasionally referred to as "second material residue") to suspend the residue in hexane.

The extraction in Step 1-3 uses hexane in an amount of 1 to 50 parts by weight, and more preferably 5-10 parts by weight, per part by weight (dry weight) of the second material residue.

The conditions for the extraction in Step 1-3 are not particularly limited. For example, a warm or cold dipping extraction method may be adopted. More specifically, hexane is added to the second material residue, and the mixture is allowed to stand or stirred for at least 5 minute at room temperature, preferably 3 minutes to an hour at room temperature.

After such suspension using hexane, equol is extracted as an insoluble matter. Therefore, by collecting the insoluble matter, an equol-containing extract is obtained. The collection of the insoluble residue is performed by a publicly-known method such as filtration or centrifugation.

Through Step 1-3, lipid-soluble impurities are removed from the liquid extract obtained in Step 1-2. The insoluble residue obtained in Step 1-3 is subjected to the following Step 1-4.

Step 1-4

Step 1-4 comprises subjecting the insoluble residues obtained in Step 1-3 to extraction using a mixed solution of hexane and ether as an extractant, and collecting the resulting liquid extract (Step 1-4).

The ether, as one of the components of the extractant used in Step 1-4, is not particularly specified. Examples of the ether include dimethylether, methylethylether, and diethylether, and they may be used singly or in combination. Among them, diethylether is particularly preferred because of its equol refining efficiency.

The mixture ratio of the mixed solution of hexane and ether used in Step 1-4 is not particularly limited; however, to obtain equol of desired purity, the ratio of hexane to ether in volume is 10:90 to 20:80, and preferably 30:70 to 25:75.

The extraction in Step 1-4 uses the mixed solution of hexane and ether in an amount of 50 to 5000 parts by weight, more preferably 200 to 1000 parts by weight, per part by weight (dry weight) of the insoluble residue obtained in Step 1-3.

The conditions for the extraction in Step 1-4 are not particularly limited. For example, a warm or cold dipping extraction method or percolation method may be adopted. More specifically, the mixed solution of hexane and ether is added to the insoluble matter obtained in Step 1-3, and the mixture is allowed to stand or stirred for at least 10 minutes at room temperature, preferably 15 minutes to 30 hours at room temperature.

After such extraction, the liquid extract is isolated to obtain equol. The collection of the liquid extract is performed by a publicly-known method such as filtration or centrifugation.

Step 1-5

The liquid extract obtained in Step 1-4 is subjected to silica gel chromatography to obtain an equol-containing fraction (Step 1-5).

Step 1-5 may adopt any kind of silica gel chromatography that uses separate columns each containing silica gel as a filler. Examples of silica gel column chromatography Include open column chromatography that causes a solvent flow by gravity drop, flash column chromatography that makes a solvent flow using a pump, and high-performance liquid chromatography. Open column chromatography and flash column chromatography are particularly preferred, as they can be easily carried out in an industrial manner. When carrying out silica gel column chromatography, it is preferable to use a mixed solution of hexane and ether as a mobile phase (developing solvent) to further improve the equol refining degree. The ether used for the mobile phase is not limited. Examples of the ether include dimethylether, methylether, and diethylether, and they may be used solely or in combination. To improve the equol refining degree, the ether is preferably the same as that used for the mixed solution of hexane and ether in Step 1-4. In the elution of equol using silica gel column chromatography in Step 1-5, it is preferable to use a mixed solution of hexane and ether identical in composition to that used in Step 1-4 as the initial mobile phase, and the ratio of ether is gradually increased according to the gradient method. Such an increase of the ratio of ether in the mobile phase causes the equol to separate from other impurities, together with the mobile phase in which hexane and ether is mixed at 40:60 to 20:80, more preferably 30:70 to 25:50. Thereafter, the fraction containing equol having been eluted by silica gel column chromatography is isolated to obtain highly pure equol. Then, the extractant is removed from the equol-containing fraction by a publicly-known method such as distillation under reduced pressure, drying or the like. This removes most of the impurities from the fraction, thereby leaving a highly pure equol solid.

2-2. Purification Method 2

Step 2-1

Purification method 2 of the present invention carries out extraction with respect to an equol-containing substance using, as an extractant, an organic solvent or an aqueous organic solvent of at least one member selected from the group consisting of ethyl acetate, alcohol, acetone, dioxane, acetonitrile, diethylether, and toluene, and then concentrates the liquid extract (Step 2-1).

In Step 2-1, the extractant may be an organic solvent of at least one member selected from the group consisting of ethyl acetate, alcohol, acetone, dioxane, acetonitrile, diethylether, and toluene. However, to ensure efficient equol extraction, it is more preferable to use an aqueous organic solvent that is obtained by adding water to the aforementioned organic solvent.

Examples of the alcohol used as an extractant include methanol, ethanol, isopropyl alcohol, and n-propyl alcohol.

A typical concentration of the aqueous organic solvent is 80 to 99 vol. %, preferably 90 to 97 vol. %. Ensuring this concentration, it is possible to obtain a liquid extract with a high equol content.

One preferable extractant used in Step 2-1 is aqueous ethyl acetate.

The extraction conditions are not particularly limited, and a warm or cold dipping extraction method or the like may be used. More specifically, an extractant is added to the equol-containing substance, and the mixture is allowed to stand or stirred for at least 30 minutes at room temperature, more preferably for 1 hour to 50 hours at room temperature.

The conditions in the Step 1-1 extraction are also not particularly limited, and a warm or cold dipping extraction method, percolation method or the like may be used.

After such extraction, equol educed in the liquid extract is isolated by a publicly-known solid-liquid dividing method such as filtration or centrifugation. The obtained liquid extract is then concentrated, for example, under reduced pressure to obtain an equol concentrate. The equol concentrate thus obtained is subjected to the following Step 2-2.

Step 2-2

The equol concentrate obtained in Step 2-1 is subjected to silica gel column chromatography to obtain an equol-containing fraction (Step 2-2).

In Step 2-2, the equol concentrate obtained in Step 2-1 may be directly subjected to silica gel column chromatography.

Further, if the extraction in Step 2-1 is carried out with an aqueous solvent containing alcohol, an equivalent amount of ethyl acetate and water that is 5 to 10 times in volume the concentrated liquid extract are added to the concentrate, and the ethyl acetate fraction is separated and concentrated to be subjected to column chromatography. This column chromatography in Step 2-2 may be any kind of chromatography that uses separate columns each containing silica gel as a filler. Examples of silica gel column chromatography include open column chromatography that causes a solvent flow by gravity drop, flash column chromatography that makes a solvent flow using a pump, and high-performance liquid chromatography. Open column chromatography and flash column chromatography are particularly preferred, as they can be easily carried out in an industrial manner.

In the silica gel column chromatography in Step 2-2, it is preferable to use a mixed solution of an ethyl ether or ethyl acetate solution (Solution A, hereinafter) and an n-hexane, petroleum ether or n-heptane solution (Solution B, hereinafter) as a mobile phase. The ratio of Solution B in the mixed solution is 2 to 50 parts by volume, more preferably 3 to 10 parts by volume, per part by volume of Solution A.

The liquid extract obtained in Step 2-1 is thus subjected to silica gel column chromatography to isolate the equol-containing fraction.

The equol-containing fraction obtained in Step 2-2 is subjected to Step 2-3

Step 2-3

The solvent is removed from the equol-containing fraction obtained in Step 2-2, and the resulting residue is subjected to recrystallization. The precipitated crystals are then isolated (Step 2-3).

The removal of a solvent from the equol-containing fraction obtained in Step 2-2 may be performed by a publicly-known solvent removal method, such as concentration under reduced pressure.

The solvent used for the recrystallization in Step 2-3 is not particularly limited as long as it can be used for the recrystallization of equol. A typical solvent is a mixed solution of ethanol and water (aqueous ethanol solution), ethyl acetate, a mixed solution of ethyl acetate and hexane, or a mixed solution of ethanol and hexane. The mixed solution of ethyl acetate and hexane and the aqueous ethanol solution are particularly preferable. More specifically, the mixed solution of ethyl acetate and hexane typically contains ethyl acetate and hexane at a volume ratio of 10:1 to 1:10. The ethanol concentration of the aqueous ethanol solution used for the recrystallization is typically 30 to 90 vol. %, preferably 40 to 70 vol. %. By carrying out the recrystallization using the mixed solution of ethyl acetate and hexane or an aqueous ethanol solution adjusted to the foregoing concentration, the purity of the resultant equol further increases.

The recrystallization in Step 2-3 can be carried out using a general method. For example, a solvent for recrystallization is added to the residue resulted from the removal of solvent from the equol-containing fraction obtained in Step 2-2, and the residue is dissolved in the solvent by heating. The solution is then cooled to precipitate equol crystals. To further facilitate or accelerate equol crystallization, equol crystal seeds may be inoculated in the sample.

The temperature condition in the crystallization is determined according to the boiling point and the freezing point of the solvent. Generally, the residue is dissolved at about the boiling point of the solvent, and crystals are precipitated at about 0 to 25° C.

3. Food Material

The present invention further provides a food material in which the equol-containing fermented soybean hypocotyl or its extract is dispersed in cacao mass. The following describes the details, such as the ingredients, of the food material of the present invention.

Equol-Containing Fermented Soybean Hypocotyl and Extraction Thereof

The equol-containing fermented soybean hypocotyl used for the food material of the present invention is the same as the equol-containing fermented soybean hypocotyl described above in the section "1. Production Method for Equol-Containing Extract". The equol-containing fermented soybean hypocotyl may be used for the food material of the present invention immediately after the fermentation, or after dried into a dry solid as required. To improve the conservation stability of the equol-containing fermented soybean hypocotyl, it is more preferable to solidify the equol-containing fermented soybean hypocotyl by heated air-drying or the like. The air-dried equol-containing fermented soybean hypocotyl may be further processed into powder as required.

The extract of the equol-containing fermented soybean hypocotyl designates an equol-containing extract resulted from solvent extraction with respect to the equol-containing fermented soybean hypocotyl.

The extract of the equol-containing fermented soybean hypocotyl is not particularly limited; however, the extract is preferably the equol-containing extract obtained by the method described above in the section "1. Production Method for Equol-Containing Extract", more preferably the equol-containing extract obtained by Production Method I described above. The extract of the equol-containing fermented soybean hypocotyl of the present invention may be used in a liquid state; however, it is more preferable to solidify the liquid extract by removing the extractant.

The food material of the present invention may contain either of the equol-containing fermented soybean hypocotyl or the extract thereof; however, the equol-containing fermented soybean hypocotyl is nutritionally preferred.

Cacao Mass

Cacao mass is a food material mainly used as an ingredient of chocolate. The cacao mass is obtained by processing cacao beans with fermentation, torrefaction, and grinding. The cacao mass used as a food material of the present invention is not particularly limited, as long as its safety as a food material is approved.

Proportion of Equol-Containing Fermented Soybean Hypocotyl or Extract Thereof and Cacao Mass In the food material of the present invention, the proportion of the equol-containing fermented soybean hypocotyl or extract thereof and cacao mass is not limited; however, in order to improve the flavor of the food more preferably, the proportion of cacao mass is generally 10 to 2000 parts by weight (dry weight), preferably 20 to 900 parts by weight, more preferably 20 to 400 parts by weight, based on 100 parts by weight of the equol-containing fermented soybean hypocotyl or extract thereof. Particularly, when using the equol-containing fermented soybean hypocotyl, the proportion of cacao mass is generally 100 to 2000 parts by weight (dry weight), preferably 200 to 900 parts by weight, and more preferably 200 to 400 parts by weight, based on 100 parts by weight of the equol-containing fermented soybean hypocotyl or extract thereof.

The food material of the present invention may consist only of the equol-containing fermented soybean hypocotyl or extract thereof and cacao mass, but may also contain other ingredients as detailed below. The sum proportion of the equol-containing fermented soybean hypocotyl or extract thereof and cacao mass is 40 to 100 wt. %, preferably 60 to 95 wt. %, and more preferably 70 to 95 wt. %, based on the gross amount of the food material of the present invention. By thus adjusting the proportion of the ingredients, the useful bioactivity derived from the equol-containing fermented soybean hypocotyl can be effectively expressed, and the food will have a good flavor.

Arbitrary Ingredients

Insofar as the effects of the invention are not impaired, the food material of the present invention may contain various ingredients in addition to the (a) equol-containing fermented soybean hypocotyl or extract thereof, and (b) cacao mass.

Examples of suitable ingredients for the food material of the present invention include sweeteners such as sugar, trehalose, acesulfam K, xylitol, sucralose, erythritol, aspartame and starch syrup; oils and fats such as cacao butter or vegetable oils; emulsifiers such as soybean lecithin; perfume; perfume preparations; milk; and water.

Form of Food Material

The shape of the food material of the present invention is not particularly limited, and may be a form of powder, granule, chip, or plate, depending on the target product form of the food. To make good use of the texture characteristic of the food material of the present invention in the product, the food material is preferably processed in the form of a granule or a chip, particularly preferably a granule or a chip of about 30 to 1000 mg per piece.

Production Method for Food Material of the Present Invention

The food material of the present invention is prepared by mixing the equol-containing fermented soybean hypocotyl or extract thereof, cacao mass, and other necessary ingredients at a temperature where the cacao butter in the cacao mass dissolves (preferably 30 to 50° C.), and then cooling and solidifying the mixture. As a result, the food material of the present invention in which the equol-containing fermented soybean hypocotyl is dispersed in cacao mass is prepared. As required, the food material of the present invention is subjected to pulverization, trituration, sizing or the like to be formed into a desired shape. Alternatively, the food material of the present invention may be shaped using extrusion granulation during the production.

Use of Food Material

The food material of the present invention may be incorporated into various kinds of foodstuffs, as a raw material of an equol-containing food, or as a food additive. The present invention also provides such equol-containing foods made of the above-described food material.

The equol-containing food of the present invention is not particularly limited, and includes baked confectionaries and frozen desserts.

Examples of the baked confectionaries include various glutinous rice crackers; wheat crackers such as wafers or waffles; biscuits; cookies; soda crackers; pies; cakes; doughnuts; and bread. Examples of the frozen desserts include ice cream, shaved ice, and ice pops.

Among them, baked confectionaries are one of the suitable forms of equol-containing food. Particularly, a baked confectionary made of soybean powder contains not only equol but also other soybean-derived useful components; therefore, the baked confectionary is highly useful, providing a superior health maintenance effect.

One preferred example of the baked confectionary made of soybean powder contains soybean powder, egg, and butter, but no wheat. The soybean powder to be used for this type of cookie is preferably processed by heating or the like to deactivate or diminish the lipoxygenases and to remove or reduce the soybean smell. Such a baked confectionary can be produced by, for example, using 0 to 35 parts by weight of egg, 10 to 65 parts by weight of butter, 0.1 to 50 parts by weight of the food material of the present invention, and other ingredients, per 100 parts by weight of soybean powder. These ingredients are mixed with an appropriate amount of water to make the dough. The dough is then formed into a predetermined shape, and baked at about 60 to 250° C. for 2 to 60 minutes.

The proportion of the food material of the present invention in the equol-containing food is not particularly limited, and is adjusted depending on the equol content in the food material of the present invention, the form of the equol-containing food or the like. The proportion of the food material of the present invention is generally 3 to 30 wt. %, preferably 5 to 20 wt. %, and more preferably 5 to 8 wt. %, based on the total amount of the materials of the equol-containing food.

Further, the proportion of equol in the equol-containing food is generally 0.002 to 0.1 wt. %, preferably 0.004 to 0.05 wt. %, and more preferably 0.005 to 0.03 wt. %, based on the total amount of the materials of the equol-containing food. By ensuring this proportion of the food material of the present invention, the useful bioactivity derived from the equol-containing fermented soybean hypocotyl is expressed in the food, while maintaining the good flavor of the equol-containing food.

The equol-containing food is produced by mixing the food material of the present invention with a predetermined amount of the other ingredients, and subjecting the mixture to forming, baking, cooling etc. depending on the target form of the food product. The equol-containing food is made of an equol-containing fermented soybean hypocotyl, and contains various useful bioactivity materials including equol, thereby expressing various bioactivities or pharmacological activities. Therefore, the equol-containing food is useful not only as a general food but also as a food for specified health use, nutritional supplement, functional food, invalid food or the like. The food containing the fermented soybean hypocotyl of the present invention is particularly useful as a nutraceutical product.

For example, the equol-containing food has an effect of preventing or treating various diseases or symptoms including menopausal disorders, osteoporosis, prostatic hypertrophy, and metabolic syndrome; or for blood cholesterol level reduction, skin-whitening, pimples, intestinal control, obesity, and diuresis. Particularly, the equol-containing food is suitable for prevention or treatment of indefinite complaint or post-menopausal symptoms (e.g., osteoporosis, menopausal disorder) of middle-aged women.

The intake of the equol-containing food per day is determined depending on the equol content in the food, age, weight, symptom of the consumer, or the dosage number.

4. Foods of Various Forms

The present invention further provides various forms of food containing the equol-containing fermented soybean hypocotyl or extract thereof. Examples of the foods of the present invention includes beverages, dietary supplements, creamy foods, desserts, confectionaries, seasonings, retort-packed foods, processed meat products, fish pastes, processed egg products, canned foods, breads, frozen desserts, processed soybean foods, cooked rice products, and soup.

The following explains in detail the equol-containing fermented soybean hypocotyl and the extract thereof, and each form of food provided by the present invention.

Equol-Containing Fermented Soybean Hypocotyl and Extract Thereof

The equol-containing fermented soybean hypocotyl or extract thereof used for the present invention is the same as that used in the section "3. Food Material".

The food of the present invention may contain any of the items in the foregoing list of equol-containing fermented soybean hypocotyls or extracts thereof. The food of the present invention preferably contains an equol-containing fermented soybean hypocotyl.

Forms of Food

The equol-containing fermented soybean hypocotyl or extract thereof is effective in preventing or treating various diseases or symptoms including menopausal disorders, osteoporosis, prostatic hypertrophy, and metabolic syndrome; or for blood cholesterol level reduction, skin-whitening, pimples, intestinal control, obesity, and diuresis. Particularly, the equol-containing food is suitable for the prevention or treatment of indefinite complaints or post menopausal symptoms (e.g. osteoporosis, menopausal disorders) of middle-aged women. Accordingly, the various forms of food of the present invention may be provided as functional foods effective for those diseases or symptoms. More specifically, the food of the present invention containing fermented soybean hypocotyl is not only useful as a general food, but also useful as a food for specified health use, a nutritional supplement, a functional food, an invalid diet food or the like. The food of the present invention containing fermented soybean hypocotyl is particularly useful as a nutritional supplement.

The following explains specific examples of the food forms of the present invention.

(1) Beverage

The present invention provides a beverage containing the equol-containing fermented soybean hypocotyl or extract thereof.

The beverage of the present invention may be any kind of beverage; however, it is suitable for beverages containing fruit juice; beverages containing vegetable juice; carbonated beverages such as sparkling water, cola, a fruit-juice-containing carbonated beverage, ginger ale, soda; soft drinks such as a sports drink; coffee beverages such as coffee or milk coffee; teas such as English-style tea, green tea, or oolong tea; cocoa; lactic acid bacteria beverages; milk beverages such as cow's milk, fruit-flavored milk, or sour milk beverages; alcoholic beverages such as beer, shochu (distilled spirit), whiskey, cocktails, or shochu mixed with soda water.

The content of the equol-containing fermented soybean hypocotyl or extract thereof in each beverage of the present invention is not limited, and is individually determined according to the equol content in the fermented soybean hypocotyl or extract thereof, the type of beverage, the expected effect or the like. For example, the content of the fermented soybean hypocotyl or extract thereof in the beverage is generally 0.02 to 15 wt. %, preferably 0.1 to 1 wt. %, and more preferably 0.2 to 0.5 wt. % (dry weight).

(2) Dietary Supplement

The present invention provides a dietary supplement containing the equol-containing fermented soybean hypocotyl or extract thereof.

The form of the dietary supplement of the present invention is not limited, and includes a softgel, a tablet, powder or the like, among which a softgel is particularly preferred. The softgel or powder is preferably contained in a capsule at a predetermined amount.

One of the suitable embodiments of the softgel of the present invention is a softgel that contains gelatin, water and glycerin having the equol-containing fermented soybean hypocotyl or extract therein. The softgel may further contain other additives such as soybean oil, beeswax, lecithin, or β-carotin.

The content of the equol-containing fermented soybean hypocotyl or extract thereof in each dietary supplement of the present invention is not limited, and is individually determined according to the equol content in the fermented soybean hypocotyl or extract thereof, the type of supplement, the expected effect or the like. For example, the content of the fermented soybean hypocotyl or extract thereof in the dietary supplement is 2 to 100 wt. % (dry weight).

(3) Creamy Food

The present invention provides a creamy food containing the equol-containing fermented soybean hypocotyl or extract thereof.

The creamy food of the present invention is not particularly limited and may include whipped cream, custard cream, butter cream, fresh cream, and coffee whitener.

The content of the equol-containing fermented soybean hypocotyl or extract thereof in each creamy food of the present invention is not limited, and is individually determined according to the equol content in the fermented soybean hypocotyl or extract thereof, the type of creamy food, the expected effect or the like. For example, the content of the fermented soybean hypocotyl or extract thereof in the creamy food is generally 0.03 to 5 wt. %, preferably 0.15 to 1 wt. %, and more preferably 0.3 to 0.5 wt. % (dry weight).

(4) Dessert

The present invention provides a dessert containing the equol-containing fermented soybean hypocotyl or extract thereof.

The dessert is not particularly limited and may include yoghurt, jelly, pudding, mousse or the like.

The content of the equol-containing fermented soybean hypocotyl or extract thereof in each dessert of the present invention is not limited, and is individually determined according to the equol content in the fermented soybean hypocotyl or extract thereof, the type of dessert, the expected effect or the like. For example, the content of the fermented soybean hypocotyl or extract thereof in the dessert is generally 0.03 to 5 wt. %, preferably 0.15 to 1 wt. %, and more preferably 0.3 to 0.5 wt. % (dry weight).

(5) Snack

The present invention provides a snack containing the equol-containing fermented soybean hypocotyl or extract thereof.

The snack is not particularly limited and may include any western or Japanese sweets including baked or steamed confectionary. Examples of the snack of the present invention include candies, lollies, caramels, pretzels, tablets, gums, chocolates, cookies, bean confectionery, wafer, cheese crackers, gummy candies, ordinary rice crackers, and Suhama (Japanese traditional confectionery), dry confectionery, and Yokan (azuki bean jelly), steamed bean-jam bun, bracken-starch dumplings, pound cakes, apple pie fillings, savory snacks, and glutinous rice crackers. Among them, one of the suitable embodiments of the snack is a baked confectionery containing soy flour.

The content of the equol-containing fermented soybean hypocotyl or extract thereof in each snack of the present invention is not limited, and is individually determined according to the equol content in the fermented soybean hypocotyl or extract thereof, the type of snack, the expected effect or the like. For example, the content of the fermented soybean hypocotyl or extract thereof in the snack is generally 0.01 to 99 wt. %, preferably 0.04 to 36 wt. %, and more preferably 0.08 to 18 wt. % (dry weight).

(6) Seasoning

The present invention provides a seasoning containing the equol-containing fermented soybean hypocotyl or extract thereof.

The seasoning is not particularly limited and may include barbecue sauce, sauce for Kabayaki (broiled seafood), seasoning of squid-chinmi, ketchup, tsuyu (soup), dressing, sesame dipping sauce, snack seasonings and soy sauce.

The content of the equol-containing fermented soybean hypocotyl or extract thereof in each seasoning of the present invention is not limited, and is individually determined according to the equol content in the fermented soybean hypocotyl or extract thereof, the type of seasoning, the expected effect or the like. For example, the content of the fermented soybean hypocotyl or extract thereof in the seasoning is generally 0.04 to 40 wt. %, preferably 0.2 to 8 wt. %, and more preferably 0.4 to 4 wt. % (dry weight).

(7) Retort-Packed Food

The present invention provides a retort-packed food (retort pouch food) containing the equol-containing fermented soybean hypocotyl or extract thereof.

The retort-packed food is not particularly limited and may include various seasoning materials including a sauce premix for curry sauce, hashed rice sauce, stew, meat sauce, or white sauce; a premix for Chinese-style donburi, beef donburi, and chicken and egg donburi; a premix for Ma-po Dou-fu (Tofu with chili and bean-based sauce), and a premix for Kamameshi (a Japanese rice dish cooked with various kinds of meat, seafood, and vegetables).

The content of the equol-containing fermented soybean hypocotyl or extract thereof in each retort-packed food of the present invention is not limited, and is individually determined according to the equol content in the fermented soybean hypocotyl or extract thereof, the type of retort-packed food, the expected effect or the like. For example, the content of the fermented soybean hypocotyl or extract thereof in the retort-packed food is generally 0.003 to 4 wt. %, preferably 0.01 to 0.8 wt. %, and more preferably 0.03 to 0.4 wt. % (dry weight).

(8) Processed Meat Product

The present invention provides a processed meat product containing the equol-containing fermented soybean hypocotyl or extract thereof.

The processed meat product of the present invention is not particularly limited and may include sausages (dry, semi-dry, bologna, wiener, smoke), liver paste, bacon, shoulder bacon, ham, hamburger steak, and meatballs.

The content of the equol-containing fermented soybean hypocotyl or extract thereof in each processed meat product of the present invention is not limited, and is individually determined according to the equol content in the fermented soybean hypocotyl or extract thereof, the type of processed meat product, the expected effect or the like. For example, the content of the fermented soybean hypocotyl or extract thereof in the processed meat product is generally 0.02 to 0.4 wt. %, preferably 0.1 to 0.8 wt. %, and more preferably 0.2 to 0.4 wt. % (dry weight).

(9) Fish Paste Product

The present invention provides a fish paste product containing the equol-containing fermented soybean hypocotyl or extract thereof.

The fish paste product of the present invention is not particularly limited and may include boiled fish paste and fish-cake tubes.

The content of the equol-containing fermented soybean hypocotyl or extract thereof in each fish paste product of the present invention is not limited, and is individually determined according to the equol content in the fermented soybean hypocotyl or extract thereof, the type of fish paste product, the expected effect or the like. For example, the content of the fermented soybean hypocotyl or extract thereof in the fish paste product is generally 0.03 to 5 wt. %, preferably 0.1 to 1 wt. %, and more preferably 0.3 to 0.5 wt. % (dry weight).

(10) Processed Egg Product

The present invention provides a processed egg product containing the equol-containing fermented soybean hypocotyl or extract thereof.

The processed egg product of the present invention is not particularly limited and may include Japanese rolled omelet, thick Japanese omelet, western-style omelet, and scrambled eggs.

The content of the equol-containing fermented soybean hypocotyl or extract thereof in each processed egg product of the present invention is not limited, and is individually determined according to the equol content in the fermented soybean hypocotyl or extract thereof, the type of processed egg product, the expected effect or the like. For example, the content of the fermented soybean hypocotyl or extract thereof in the processed egg product is generally 0.03 to 5 wt. %, preferably 0.1 to 1 wt. %, and more preferably 0.3 to 0.5 wt. % (dry weight).

(11) Canned Food

The present invention provides a canned food containing the equol-containing fermented soybean hypocotyl or extract thereof.

The canned food of the present invention is not particularly limited and may include canned fruit such as canned oranges or canned peaches; canned seafood such as canned tuna or canned sardines; canned jam; canned soup; and canned sauce.

The content of the equol-containing fermented soybean hypocotyl or extract thereof in each canned food of the present invention is not limited, and is individually determined according to the equol content in the fermented soybean hypocotyl or extract thereof, the type of canned food, the expected effect or the like. For example, the content of the fermented soybean hypocotyl or extract thereof in the canned food is generally 0.03 to 5 wt. %, preferably 0.1 to 1 wt. %, and more preferably 0.3 to 0.5 wt. % (dry weight).

(12) Bread

The present invention provides bread containing the equol-containing fermented soybean hypocotyl or extract thereof.

The bread of the present invention is not particularly limited and may include a loaf of bread, French bread, stuffed bread, melon bread, bean-jam bread, cream bread, jam bread, bread rolls, and croissants.

The content of the equol-containing fermented soybean hypocotyl or extract thereof in each bread of the present invention is not limited, and is individually determined according to the equol content in the fermented soybean hypocotyl or extract thereof, the type of bread, the expected effect or the like. For example, the content of the fermented soybean hypocotyl or extract thereof in the bread is generally 0.01 to 50 wt. %, preferably 0.05 to 0.6 wt. %, and more preferably 0.1 to 0.3 wt. % (dry weight).

(13) Frozen Dessert

The present invention provides a frozen dessert containing the equol-containing fermented soybean hypocotyl or extract thereof.

The bread of the present invention is not particularly limited and may include ice cream and sherbet.

The content of the equol-containing fermented soybean hypocotyl or extract thereof in each frozen dessert of the present invention is not limited, and is individually determined according to the equol content in the fermented soybean hypocotyl or extract thereof, the type of frozen dessert, the expected effect or the like. For example, the content of the fermented soybean hypocotyl or extract thereof in the frozen dessert is generally 0.03 to 5 wt. %, preferably 0.1 to 1 wt. %, and more preferably 0.3 to 0.5 wt. % (dry weight).

(14) Processed Soybean Food

The present invention provides a processed soybean food containing the equol-containing fermented soybean hypocotyl or extract thereof.

The processed soybean food of the present invention is not particularly limited and may include tofu, thick deep-fried tofu, fried tofu mixed with vegetables, soy milk skin, fermented soybeans, and soy milk.

The content of the equol-containing fermented soybean hypocotyl or extract thereof in each processed soybean food of the present invention is not limited, and is individually determined according to the equol content in the fermented soybean hypocotyl or extract thereof, the type of processed soybean food, the expected effect or the like. For example, the content of the fermented soybean hypocotyl or extract thereof in the processed soybean food is generally 0.03 to 0.5 wt. %, preferably 0.1-1 wt. %, and more preferably 0.3-0.5 wt. % (dry weight).

(15) Cooked Rice Product

The present invention provides a cooked rice product containing the equol-containing fermented soybean hypocotyl or extract thereof. The cooked rice product of the present invention is not particularly limited and may include fried rice, pilaf, rice gruel, steamed glutinous rice with chestnut, cooked white rice, red beans rice, and rice steamed with meat and vegetables.

The content of the equol-containing fermented soybean hypocotyl or extract thereof in each cooked rice product of the present invention is not limited, and is individually determined according to the equol content in the fermented soybean hypocotyl or extract thereof, the type of cooked rice product, the expected effect or the like. For example, the content of the fermented soybean hypocotyl or extract thereof in the cooked rice product is generally 0.01 to 2.5 wt. %, preferably 0.02 to 0.5 wt. %, and more preferably 0.04 to 0.25 wt. % (dry weight).

(16) Soup

The present invention provides soup containing the equol-containing fermented soybean hypocotyl or extract thereof.

The soup of the present invention is not particularly limited and may include corn cream soup, consomme, minestrone, onion soup, and potage.

The content of the equol-containing fermented soybean hypocotyl or extract thereof in each soup of the present invention is not limited, and is individually determined according to the equol content in the fermented soybean hypocotyl or extract thereof, the type of soup, the expected effect or the like. For example, the content of the fermented soybean hypocotyl or extract thereof in the soup is generally 0.02 to 15 wt. %, preferably 0.1 to 1 wt. %, and more preferably 0.2 to 0.5 wt. % (dry weight).

EXAMPLES

The following more specifically explains the present invention with reference to Reference Examples, Examples etc. The present invention is however not limited to these examples.

Reference Examples 1-1 to 1-3

Production of Equol-Containing Fermented Soybean Hypocotyl

Soybean hypocotyl powder, arginine, and water were mixed to prepare a soybean hypocotyl solution (material) having a composition as shown in Table 1. A *Lactococcus* 20-92 strain (FERM BP-10036) was inoculated in this soybean hypocotyl solution of 5 ml, and the sample was subjected to stationary culture for 96 hours at 37° C. under anaerobic conditions. After that, the resulting fermentation solution (culture solution) was sterilized by heating for a minute at 100° C., followed by drying at 80° C. The dried product was processed into a powder using a homogenizer to obtain fermented soybean hypocotyl powder.

Table 1 shows the viable cell count and pH of the culture after 96 hours culture, the amount of fermented soybean hypocotyl powder collected and the equol content of the fermented soybean hypocotyl powder. From the data, it is shown that fermentation of soybean hypocotyl powder using equol-producing bacteria produces equol with high efficiency.

TABLE 1

| | | Ref. Ex. 1-1 | Ref. Ex. 1-2 | Ref. Ex. 1-3 |
|---|---|---|---|---|
| Composition of Soybean Hypocotyl Solution (Material) | Soybean Hypocotyl Powder (dry wt.) | 0.25 g | 0.5 g | 0.75 g |
| | Arginine | 0.005 g | 0.005 g | 0.005 g |
| | Water | Appropriate Quantity | Appropriate Quantity | Appropriate Quantity |
| | Total Amount | 5 ml | 5 ml | 5 ml |
| | PH | 6.75 ± 0.03 | 6.54 ± 0.02 | 6.39 ± 0.03 |
| Analytical Result of Fermented Liquid | Viable Bacterial Counts of Fermented Liquid (log cfu/ml) | 7.9 ± 0.1 | 8.2 ± 0.1 | 8.3 ± 0.2 |
| | PH of Fermented Liquid | 7.00 ± 0.03 | 6.88 ± 0.01 | 6.76 ± 0.02 |
| Analysis of Composition of Fermented Soybean Hypocotyl Powder in terms of Isoflavone | Equol | 3.85 mg (—) | 3.44 mg (—) | 5.38 mg (48.9 wt. %) |
| | Daidzein Compounds | n.d. (—) | n.d. (—) | 1.18 mg (10.7 wt. %) |
| | Genistein Compounds | n.d. (—) | n.d. (—) | 1.45 mg (13.2 wt. %) |
| | Glycitein Compounds | n.d. (—) | n.d. (—) | 3.00 mg (27.2 wt. %) |

Each Example was performed using three lots of soybean hypocotyl powder (N=3). In the analysis of isoflavone composition in the table, the value on the left denotes a content (mg) of each isoflavone per gram of the fermented soybean hypocotyl, and the value in the bracket on the right denotes the ratio (wt. %) of each isoflavone to the gross isoflavone amount (100 wt. %) in the fermented soybean hypocotyl. "n.d." indicates that the measurement is not done, and "—" in the bracket indicates that the calculation is not done.

Reference Example 1-4

Production of Equol-Containing Fermented Soybean Hypocotyl

A *Lactococcus* 20-92 strain (FERM BP-10036) was inoculated to a 5 ml soybean hypocotyl solution containing 10 wt % of soybean hypocotyl powder and 0.1 wt. % of arginine, and the sample was subjected to fermentation by carrying out stationary culture for 96 hours at 37° C. under anaerobic conditions. After that, the resulting fermentation solution (culture solution) was sterilized by heating for a minute at 100° C., followed by drying at 80° C. The dried product was processed into powder using a homogenizer to obtain fermented soybean hypocotyl powder.

The respective components of the soybean hypocotyl powder ("Pre-fermentation" in Table 2 and Table 3) and of the fermented soybean hypocotyl powder ("Post-fermentation" in Table 2 and Table 3) were analyzed. Table 2 shows an analysis regarding soy isoflavone, and Table 3 shows an analysis regarding nutritional components. These tables show that the fermented soybean hypocotyl obtained by the fermentation of soybean hypocotyl using a *Lactococcus* 20-92 strain has a high equol content. Further, oligosaccharide content for such oligosaccharides as raffinose or stachyose remains substantially the same after fermentation, which indicates that the fermentation did not influence the oligosaccharide content. Meanwhile, the tables show that arginine was converted into ornithine by the fermentation. Accordingly, by adding arginine to the soybean hypocotyl before fermentation using a *Lactococcus* 20-strain, the resulting fermented substance contains not only equol but also ornithine.

TABLE 2

Soybean Isoflavones

| Component | Pre-fermentation | Post-fermentation Per 100 g |
|---|---|---|
| Equol | N.D. | 632.0 mg |
| Daidzin | 566.4 mg | 29.7 mg |
| Malonyldaidzin | 124.9 mg | N.D. |
| Acetyldaidzin | 364.8 mg | 25.4 mg |
| Daidzein | 7.1 mg | 24.4 mg |
| Dihydrodaidzein | N.D. | 49.4 mg |
| Genistin | 111.7 mg | 3.2 mg |
| Malonylgenistin | 35.1 mg | N.D. |
| Acetylgenistin | 146.1 mg | 3.7 mg |
| Genistein | 0.9 mg | 22.5 mg |
| Dihydrogenistein | N.D. | 112.0 mg |
| Glycitin | 331.7 mg | 53.6 mg |
| Malonylglycitin | 65.0 mg | N.D. |

TABLE 2-continued

Soybean Isoflavones

| Component | Pre-fermentation | Post-fermentation Per 100 g |
|---|---|---|
| Acetylglycitin | 169.2 mg | 34.8 mg |
| Glycitein | 19.1 mg | 292.3 mg |
| Dihydroglycitein | N.D. | 8.2 mg |
| Total Isoflavones | 1942.0 mg | 1291.2 mg |

N.D. refers to "Not Detected"

TABLE 3

Nutritional Component Per 100 g

| Component | Pre-fermentation | Post-fermentation |
|---|---|---|
| Moisture | 3.2 g | 6.2 g |
| Protein | 38.1 g | 38.3 g |
| Fat | 13.0 g | 14.5 g |
| Ash | 4.3 g | 4.0 g |
| Saccharide | 30.9 g | 26.8 g |
| Dietary Fiber | 10.5 g | 10.2 g |
| Energy | 414 kcal | 411 kcal |
| Sucrose | 7.95 g | 7.42 g |
| Raffinose | 1.37 g | 1.34 g |
| Stachyose | 9.04 g | 8.38 g |
| Trans Fatty Acids | N.D. | N.D. |
| Phospholipids (as stear-, ole-, and lecithin) | 3.33 g | 2.92 g |
| Free Arginine | 881 mg | 12 mg |
| Free Ornithine | N.D. | 1.06 g |
| Soyasapogenol A | N.D. | N.D. |
| Soyasapogenol B | N.D. | N.D. |
| Soybean Saponin | 3.6 g | 3.8 g |

N.D. refers to "Not Detected"

Reference Examples 1-5 to 1-11

Production of Equol-Containing Fermented Soybean Hypocotyl

In these examples, fermented soybean hypocotyl powder (Reference Examples 1-5 to 1-11) were produced in the same manner as in Reference Examples 1-3 except that seven lots of soybean hypocotyl powder different from the three lots of Reference Example 1-3 were used. The compositions of isoflavone in the obtained fermented soybean hypocotyl was analyzed as shown in Table 4. This result also shows that each of the fermented soybean hypocotyls of Reference Examples 1-5 to 1-11 has a high equol content with isoflavone proportion that was not attained by any known arts.

TABLE 4

Isoflavone Proportions

| | Equol | Daidzein Compounds | Genistein Compounds | Glycitein Compounds |
|---|---|---|---|---|
| Ref. Ex. 1-5 | 6.51 mg (62.2 wt. %) | 0.71 mg (6.8 wt. %) | 0.53 mg (5.1 wt. %) | 2.71 mg (25.9 wt. %) |
| Ref. Ex. 1-6 | 6.25 mg (61.3 wt. %) | 0.48 mg (4.7 wt. %) | 0.35 mg (3.4 wt. %) | 3.12 mg (30.6 wt. %) |
| Ref. Ex. 1-7 | 5.38 mg (48.9 wt. %) | 1.18 mg (10.7 wt. %) | 1.45 mg (13.2 wt. %) | 3.00 mg (27.2 wt. %) |
| Ref. Ex. 1-8 | 6.43 mg (63.4 wt. %) | 0.61 mg (6.0 wt. %) | 0.48 mg (4.7 wt. %) | 2.62 mg (25.8 wt. %) |
| Ref. Ex. 1-9 | 6.05 mg (64.2 wt. %) | 0.51 mg (5.4 wt. %) | 0.30 mg (3.2 wt. %) | 2.57 mg (27.3 wt. %) |
| Ref. Ex. 1-10 | 6.11 mg (65.6 wt. %) | 0.37 mg (4.0 wt. %) | 0.10 mg (1.1 wt. %) | 2.74 mg (29.4 wt. %) |

TABLE 4-continued

| | Isoflavone Proportions | | | |
|---|---|---|---|---|
| | Equol | Daidzein Compounds | Genistein Compounds | Glycitein Compounds |
| Ref. Ex. 1-11 | 6.3 mg (60.9 wt. %) | 0.49 mg (4.73 wt. %) | 0.37 mg (3.6 wt. %) | 3.19 mg (30.8 wt. %) |

The value in the upper column denotes a content (mg) of each isoflavone per gram of the fermented soybean hypocotyl, and the value in the lower column denotes the ratio (wt. %) of each isoflavone to the gross isoflavone amount (100 wt. %) in the fermented soybean hypocotyl.

Reference Experiment Example 1

Allergen Confirmation Test

Soybean hypocotyl is known to contain allergens including Gym4, Gm30K, Gm28K, 7S globulin mix (β-conglycine), oleosin, and trypsin inhibitors. The existence of allergens in the equol-containing fermented soybean hypocotyl produced in Reference Example 1-1 was examined using the following test.

First, an appropriate amount of the equol-containing fermented soybean hypocotyl obtained in Reference Example 1-1 was added to an extraction buffer (Tris HCl, pH 7.5, containing 1M EDTA and an appropriate amount of protease inhibitor). The sample was stirred well to extract a water-soluble component. The resulting solution was filtered to remove the solid content to obtain a liquid extract. All proteins contained in this liquid extract were detected using a protein assay system (Bio-Rad). Further, the major allergens (Gym4, Gm30K, Gm28K, 7S globulin mix, oleosin, and trypsin inhibitor) contained in the liquid extract were detected using western blotting. Further, for comparison, the detection of total protein and allergen was carried out in the same manner using soybean cotyledon powder and soybean hypocotyl powder, instead of the fermented soybean hypocotyl.

FIGS. 1 to 3 show the result. FIG. 1 shows the result for the detection of total protein; FIG. 2 shows the result for the detection of Gym4, Gm30K, and Gm28K; and FIG. 3 shows the result for the detection of 7S globulin mix, oleosin, and trypsin inhibitor.

These results show that the major allergen content of a soybean or a soybean hypocotyl is reduced in the equol-containing fermented soybean hypocotyl.

Example 1

Production of Equol-Containing Extract

Example 1-1

Production of Equol-Containing Extract by Production Method I

One gram of the equol-containing fermented soybean hypocotyl powder produced under the same conditions as in Reference Examples 1 to 3 was added to 20 ml of the extractant according to Table 5; and 120 minutes of shaking was performed at room temperature. Thereafter, the residue ("Residue 1", hereinafter) was removed by centrifugation to isolate a liquid extract ("Liquid Extract 1-1", hereinafter). Next, Liquid Extract 1-1 was evaporated to dryness using an evaporator, 5 ml of ethanol was added thereto, and 10 minutes of shaking was performed at room temperature. Thereafter, the residue ("Residue 2", hereinafter) was removed by centrifugation to isolate a liquid extract ("Liquid Extract 1-2", hereinafter). Liquid Extract 1-2 was then evaporated to dryness using an evaporator to obtain a solid extract.

Further, another 20 ml of extractant of the same composition was added to Residue 1, and 120 minutes shaking was performed at room temperature. Thereafter, the residue was removed by centrifugation to isolate a liquid extract (Liquid Extract 2-1, hereinafter). Liquid Extract 2-1 was then evaporated to dryness using an evaporator. 5 ml of ethanol was added thereto, and 10 minutes of shaking was performed at room temperature. Thereafter, the residue was removed by centrifugation to isolate an extract ("Liquid Extract 2-2", hereinafter). Liquid Extract 2-2 was evaporated to dryness using an evaporator to obtain a solid extract.

TABLE 5

| Name of Extractant | Composition of Extractant |
|---|---|
| 25Et | Ethanol Solution containing 25 vol. % of Ethanol and 75 vol. % of Purified Water |
| 50Et | Ethanol Solution containing 50 vol. % of Ethanol and 50 vol. % of Purified Water |
| 75Et | Ethanol Solution containing 75 vol. % of Ethanol and 25 vol. % of Purified Water |
| 100Et | 100 vol. % of Ethanol |

Liquid Extracts 1-1 and 1-2, Liquid Extracts 2-1 and 2-2, and Residue 2 were subjected to thin-layer chromatography (TLC) analysis (as a mobile phase, hexane:chloroform:ethyl acetate=1:1:1 (volume ratio) was used for equol detection; and ethyl acetate:propanol:chloroform:methanol:0.9% KCl=25:25:25:10:9 (volume ratio) was used for saponin detection) so as to measure saponin content and equol content. The weight of the solid extract obtained from Liquid Extract 1-2 and its equol concentration were measured. FIGS. 4 to 7 and Table 6 show the results. FIG. 4 shows the results of TLC analysis of the equol contents in Liquid Extracts 1-2 and 2-2; FIG. 5 shows the results of TLC analysis of the saponin contents in Liquid Extracts 1-2 and 2-2; FIG. 6 shows the results of TLC analysis of the equol contents in Liquid Extract 1-2 and Residue 2; and FIG. 7 shows the results of TLC analysis of the saponin contents in Liquid Extract 1-2 and Residue 2.

According to the figures, it was found that when the equol-containing fermented soybean hypocotyl was subjected to the extraction using ethanol, the extract contained a large amount of oil, and the equol recovery rate was low.

In contrast, when the equol-containing fermented soybean hypocotyl was subjected to the extraction using an aqueous ethanol, the inclusion of oil was suppressed, and the equol recovery rate increased. Particularly, it became clear that use of an aqueous ethanol solution having an ethanol concentration of 75 vol. 5, significantly increases the equol collection rate. Further, it was also found that extraction using a 75 vol. % ethanol minimizes the extraction of fat components. Furthermore, according to the fact that saponin in a concentrated amount was detected in Residue 2, saponin can be removed without reducing the equol amount by subjecting the residue, which was obtained by removing solvent from Liquid Extract 1-1, to extraction using ethanol.

TABLE 6

| Extract Type | EQL-containing Fermented Soybean Hypocotyl | | | Solid Extract Collected from Liquid Extract 1-2 | | | | |
|---|---|---|---|---|---|---|---|---|
| | Amount Used for Extraction (g) | EQL Content (mg) | EQL Concentration (wt. %) | Dry Weight (mg) | EQL Content (mg) | EQL Concentration (wt. %) | EQL Collection Rate (%) | EQL Concentration Rate |
| 25Et | 1 | 5.38 | 0.54 | 43 | 1.78 | 4.14 | 33.1 | 7.7 |
| 50Et | 1 | 5.38 | 0.54 | 36 | 2.68 | 7.44 | 49.8 | 13.8 |
| 75Et | 1 | 5.38 | 0.54 | 121 | 5.56 | 4.60 | 103.4 | 8.5 |
| 100Et | 1 | 5.38 | 0.54 | 146 | 1.50 | 1.03 | 27.9 | 1.9 |

EQL represents equol. The "concentration rate" represents the EQL concentration rate of the solid extract when assuming the EQL concentration in the EQL-containing fermented soybean hypocotyl is 1.

Example 1-2

Production of Equol-Containing Extract by Production Method I

In this example, equol-containing fermented soybean hypocotyl powder was produced under the same conditions as in Reference Example 1-3 except that a different lot of soybean hypocotyl powder was used.

30 g of the equol-containing fermented soybean hypocotyl powder was added to 150 ml of a 70 vol. % aqueous ethanol solution (100 ml consisting of ethanol and 30 ml of water) or 150 ml of a 90 vol. aqueous ethanol solution (100 ml consisting of ethanol and 10 ml of water); and eight hours stirring was performed at room temperature. After removing the residue by filtration, the residue was washed with a 20 ml of aqueous ethanol solution having the same composition as that of the extractant. The filtrate and the liquid after washing were collected to obtain a liquid extract. The liquid extract was concentrated under reduced pressure to obtain a solid extract.

The weight of the obtained solid extract and the weight of equol contained therein and the concentrations of daidzein, dihydrodaidzein, genistein, dihydrogenistein, glystein, dihydroglystein were measured, as shown in Tables 7 and 8.

TABLE 7

Extraction Results for 70 vol. % Ethanol Solution

| | EQL-containing Fermented Soybean Hypocotyl | | Collected Solid Extract | | | |
|---|---|---|---|---|---|---|
| Weight | Amount for Extraction (g) | 30 | Dry Weight (mg) | 8000 | | |
| EQL | EQL Content (mg) 161.40 | EQL Concentration (wt. %) 0.54 | EQL Content (mg) 158.98 | EQL Concentration (wt. %) 1.98 | EQL Collection Rate (%) 98.5 | EQL Concentration Rate 3.7 |
| DZN | DZN Content (mg) 6.00 | DZN Concentration (wt. %) 0.02 | DZN Content (mg) 0.00 | DZN Concentration (wt. %) 0.00 | DZN Collection Rate (%) 0.0 | DZN Concentration Rate (%) 0.0 |
| DHD | DHD Content (mg) 9.00 | DHD Concentration (wt. %) 0.03 | DHD Content (mg) 0.09 | DHD Concentration (wt. %) 0.00 | DHD Collection Rate (%) 0.00 | DHD Concentration Rate (%) 0.00 |
| GNT | GNT Content (mg) 6.90 | GNT Concentration (wt. %) 0.02 | GNT Content (mg) 0.31 | GNT Concentration (wt. %) 0.00 | GNT Collection Rate (%) 4.5 | GNT Concentration Rate (%) 0.2 |
| DHG | DHG Content (mg) 32.7 | DHG Concentration (wt. %) 0.11 | DHG Content (mg) 6.96 | DHG Concentration (wt. %) 0.09 | DHG Collection Rate (%) 21.3 | DHG Concentration Rate (%) 0.5 |
| GLY | GLY Content (mg) 62.70 | GLY Concentration (wt. %) 0.21 | GLY Content (mg) 33.17 | GLY Concentration (wt. %) 0.41 | GLY Collection Rate (%) 52.9 | GLY Concentration Rate (%) 2.0 |
| DHG | DHG Content (mg) 0.9 | DHG Concentration (wt. %) 0.00 | DHG Content (mg) 0.00 | DHG Concentration (wt. %) 0.00 | DHG Collection Rate (%) 0.00 | DHG Concentration Rate (%) 0.00 |

EQL represents equol;
DZN represents daidzein;
DHD represents dihydrodaidzein;
GNT represents genistein;
DHG represents dihydrogenistein;
GLY represents glystein; and
DHG represents dihydroglystein.

The isoflavone content (mg) denotes the gross weight of each isoflavone contained in the EQL-containing fermented soybean hypocotyl (material: 30 g) or in the obtained isolated extract (8000 mg); and the isoflavone concentration (wt. %) denotes the proportion of each isoflavone contained in the EQL-containing fermented soybean hypocotyl (material) or in the obtained isolated extract. The "Concentration Rate" represents the concentration rate of each component in the solid extract when assuming the concentration of the component in the EQL-containing fermented soybean hypocotyl is 1.

TABLE 8

Extraction Results for 90 vol. % Ethanol Solution

| | EQL-containing Fermented Soybean Hypocotyl | | | Collected Solid Extract | | | |
|---|---|---|---|---|---|---|---|
| Weight | Amount for Extraction (g) | 30 | | Dry Weight (mg) | 4100 | | |
| EQL | EQL Content (mg) 161.40 | EQL Concentration (wt. %) 0.54 | | EQL Content (mg) 158.13 | EQL Concentration (wt. %) 3.89 | EQL Collection Rate (%) 98.0 | EQL Concentration Rate 7.2 |
| DZN | DZN Content (mg) 6.00 | DZN Concentration (wt. %) 0.02 | | DZN Content (mg) 0.00 | DZN Concentration (wt. %) 0.00 | DZN Collection Rate (%) 0.0 | DZN Concentration Rate (%) 0.0 |
| DHD | DHD Content (mg) 9.00 | DHD Concentration (wt. %) 0.03 | | DHD Content (mg) 0.12 | DHD Concentration (wt. %) 0.00 | DHD Collection Rate (%) 1.3 | DHD Concentration Rate (%) 0.1 |
| GNT | GNT Content (mg) 6.90 | GNT Concentration (wt. %) 0.02 | | GNT Content (mg) 0.34 | GNT Concentration (wt. %) 0.01 | GNT Collection Rate (%) 4.9 | GNT Concentration Rate (%) 0.4 |
| DHG | DHG Content (mg) 32.7 | DHG Concentration (wt. %) 0.11 | | DHG Content (mg) 6.89 | DHG Concentration (wt. %) 0.17 | DHG Collection Rate (%) 21.1 | DHG Concentration Rate (%) 1.4 |
| GLY | GLY Content (mg) 62.70 | GLY Concentration (wt. %) 0.21 | | GLY Content (mg) 32.64 | GLY Concentration (wt. %) 0.80 | GLY Collection Rate (%) 52.1 | GLY Concentration Rate (%) 3.8 |
| DHG | DHG Content (mg) 0.9 | DHG Concentration (wt. %) 0.00 | | DHG Content (mg) 0.00 | DHG Concentration (wt. %) 0.00 | DHG Collection Rate (%) 0.00 | DHG Concentration Rate (%) 0.00 |

EQL represents equol;
DZN represents daidzein;
DHD represents dihydrodaidzein;
GNT represents genistein;
DHG represents dihydrogenistein;
GLY represents glystein; and
DHG represents dihydroglystein.

The isoflavone content (mg) denotes the gross weight of each isoflavone contained in the EQL-containing fermented soybean hypocotyl (material: 30 g) or in the obtained isolated extract (4100 mg); and the isoflavone concentration (wt. %) denotes the proportion of each isoflavone contained in the EQL-containing fermented soybean hypocotyl (material) or in the obtained isolated extract. The "Concentration Rate" represents the concentration rate of each component in the solid extract when assuming the concentration of the component in the EQL-containing fermented soybean hypocotyl is 1.

The tables show that, by carrying out extraction on an equol-containing fermented soybean hypocotyl using an aqueous ethanol solution, the equol collection rate increases and glystein was also collected. Meanwhile, the concentrations of other isoflavones were all very low in this extract.

Example 1-3

Production of Equol-Containing Extract by Production Method I

In this example, equol-containing fermented soybean hypocotyl powder was produced under the same conditions as in Reference Example 1-3 except that a different lot of soybean hypocotyl powder was used.

50 g of the equol-containing fermented soybean hypocotyl powder was mixed with 7 ml of purified water, and then further mixed with 250 ml of n-hexane; and seven hours of stirring was performed at room temperature. Insoluble residue ware isolated by filtration, and seven hours of drying was performed at 60° C. to obtain defatted equol-containing fermented soybean hypocotyl powder.

20 g of the defatted equol-containing fermented soybean hypocotyl powder was added to 100 ml of a 80 vol. % aqueous ethanol solution (100 ml consisting of ethanol and 20 ml of water) or 100 ml of a 90 vol. % aqueous ethanol solution (100 ml consisting of ethanol and 10 ml of water), and fourteen hours of stirring was performed at room temperature. After removing the residue by filtration, the residue was washed using 10 ml of an aqueous ethanol solution having the same composition as that of the extractant. The filtrate and the liquid after washing were isolated to obtain a liquid extract.

The liquid extract was dried for six hours at 60° C. to obtain a solid extract.

The weight of the obtained solid extract and the weight of equol contained therein and the concentrations of daidzein, dihydrodaidzein, genistein, dihydrogenistein, glystein, dihydroglystein were measured, as shown in Tables 9 and 10.

TABLE 9

Extraction Results for 80 vol. % Ethanol Solution

|  | Defatted EQL-containing Fermented Soybean Hypocotyl powder | | | Collected Solid Extract | | |
|---|---|---|---|---|---|---|
| Weight | Amount for Extraction (g) | 20 | Dry Weight (mg) | | 4000 | |
| EQL | EQL Content (mg) 107.60 | EQL Concentration (wt. %) 0.54 | EQL Content (mg) 114.89 | EQL Concentration (wt. %) 2.88 | EQL Collection Rate (%) 106.8 | EQL Concentration Rate 5.3 |
| DZN | DZN Content (mg) 4.00 | DZN Concentration (wt. %) 0.02 | DZN Content (mg) 0.00 | DZN Concentration (wt. %) 0.00 | DZN Collection Rate (%) 0.0 | DZN Concentration Rate (%) 0.0 |
| DHD | DHD Content (mg) 6.00 | DHD Concentration (wt. %) 0.03 | DHD Content (mg) 0.10 | DHD Concentration (wt. %) 0.00 | DHD Collection Rate (%) 1.7 | DHD Concentration Rate (%) 0.1 |
| GNT | GNT Content (mg) 4.60 | GNT Concentration (wt. %) 0.02 | GNT Content (mg) 0.28 | GNT Concentration (wt. %) 0.01 | GNT Collection Rate (%) 0.01 | GNT Concentration Rate (%) 0.4 |
| DHG | DHG Content (mg) 32.7 | DHG Concentration (wt. %) 0.11 | DHG Content (mg) 6.96 | DHG Concentration (wt. %) 0.13 | DHG Collection Rate (%) 21.3 | DHG Concentration Rate (%) 0.9 |
| GLY | GLY Content (mg) 41.80 | GLY Concentration (wt. %) 0.21 | GLY Content (mg) 24.03 | GLY Concentration (wt. %) 0.60 | GLY Collection Rate (%) 57.5 | GLY Concentration Rate (%) 2.9 |
| DHG | DHG Content (mg) 0.6 | DHG Concentration (wt. %) 0.00 | DHG Content (mg) 0.00 | DHG Concentration (wt. %) 0.00 | DHG Collection Rate (%) 0.00 | DHG Concentration Rate (%) 0.00 |

EQL represents equol;
DZN represents daidzein;
DHD represents dihydrodaidzein;
GNT represents genistein;
DHG represents dihydrogenistein;
GLY represents glystein; and
DHG represents dihydroglystein.

The isoflavone content (mg) denotes the total weight of each isoflavone contained in the defatted EQL-containing fermented soybean hypocotyl (material: 20 g) or in the collected extract (4000 mg); and the isoflavone concentration (wt. %) denotes the proportion of each isoflavone contained in the defatted EQL-containing fermented soybean hypocotyl (material) or in the collected extract. The "Concentration Rate" represents the concentration rate of each component in the solid extract when assuming the concentration of the component in the defatted EQL-containing fermented soybean hypocotyl is 1.

TABLE 10

Extraction Results for 90 vol. % Ethanol Solution

|  | Defatted EQL-containing Fermented Soybean Hypocotyl powder | | | Collected Solid Extract | | |
|---|---|---|---|---|---|---|
| Weight | Amount for Extraction (g) | 20 | Dry Weight (mg) | | 2200 | |
| EQL | EQL Content (mg) 107.60 | EQL Concentration (wt. %) 0.54 | EQL Content (mg) 106.88 | EQL Concentration (wt. %) 4.81 | EQL Collection Rate (%) 99.3 | EQL Concentration Rate 8.9 |
| DZN | DZN Content (mg) 4.00 | DZN Concentration (wt. %) 0.02 | DZN Content (mg) 0.00 | DZN Concentration (wt. %) 0.00 | DZN Collection Rate (%) 0.0 | DZN Concentration Rate (%) 0.0 |
| DHD | DHD Content (mg) 6.00 | DHD Concentration (wt. %) 0.03 | DHD Content (mg) 0.10 | DHD Concentration (wt. %) 0.00 | DHD Collection Rate (%) 1.7 | DHD Concentration Rate (%) 0.2 |

TABLE 10-continued

Extraction Results for 90 vol. % Ethanol Solution

| | Defatted EQL-containing Fermented Soybean Hypocotyl powder | | Collected Solid Extract | | | |
|---|---|---|---|---|---|---|
| GNT | GNT Content (mg) 4.60 | GNT Concentration (wt. %) 0.02 | GNT Content (mg) 0.21 | GNT Concentration (wt. %) 0.01 | GNT Collection Rate (%) 0.01 | GNT Concentration Rate (%) 0.4 |
| DHG | DHG Content (mg) 32.7 | DHG Concentration (wt. %) 0.11 | DHG Content (mg) 6.96 | DHG Concentration (wt. %) 0.21 | DHG Collection Rate (%) 21.3 | DHG Concentration Rate (%) 1.5 |
| GLY | GLY Content (mg) 41.80 | GLY Concentration (wt. %) 0.21 | GLY Content (mg) 21.97 | GLY Concentration (wt. %) 0.99 | GLY Collection Rate (%) 52.6 | GLY Concentration Rate (%) 4.7 |
| DHG | DHG Content (mg) 0.6 | DHG Concentration (wt. %) 0.00 | DHG Content (mg) 0.00 | DHG Concentration (wt. %) 0.00 | DHG Collection Rate (%) 0.00 | DHG Concentration Rate (%) 0.00 |

EQL represents equol;
DZN represents; daidzein;
DHD represents dihydrodaidzein;
GNT represents genistein;
DHG represents dihydrogenistein;
GLY represents glystein; and
DHG represents dihydroglystein.

The isoflavone content (mg) denotes the gross weight of each isoflavone contained in the defatted EQL-containing fermented soybean hypocotyl (material: 20 g) or in the collected extract (2200 mg); and the isoflavone concentration (wt. %) denotes the proportion of each isoflavone contained in the defatted EQL-containing fermented soybean hypocotyl (material) or in the collected extract. The "Concentration Rate" represents the concentration rate of each component in the solid extract when assuming the concentration of the component in the defatted EQL-containing fermented soybean hypocotyl is 1.

The tables show that the high equol collection rate obtained in Example 1-2 was ensured even when defatting the equol-containing fermented soybean hypocotyl in advance.

Example 1-4

Production of Equol-Containing Extract by Production Method II

In this example, equol-containing fermented soybean hypocotyl powder (equol concentration=6.2 mg/g) was produced under the same conditions as in Reference Example 1-3 except that a different lot of soybean hypocotyl powder was used.

80 g of the equol-containing fermented soybean hypocotyl powder was suspended in 900 ml of water. 5 ml of acetic acid was added to the suspension while it was being stirred, until the pH became approximately 4.0. After 24 hours standing at room temperature, insoluble residue was collected by filtration, and dried. 50.33 g of insoluble residue was thus obtained.

Then, 250 ml of an aqueous ethanol solution (ethanol concentration=75 vol. %) was added to the 50.33 g of insoluble residue, and two days stirring was performed at room temperature. After removing the residue by filtration under reduced pressure, the filtrate was collected. The filtrate was evaporated to dryness into a solid with an evaporator to obtain 7.53 g of equol-containing powder.

The equol concentration of the obtained equol-containing powder was 60.0 mg/g, which was about ten times the equol concentration (6.2 mg/g) of the equol-containing fermented soybean hypocotyl which was used as the starting material. The recovery rate of equol was 91%.

Example 2

Equol Purification

Example 2-1

Equol Purification Method 1

Equol-containing fermented soybean hypocotyl powder (equol concentration=6.2 mg/g) was produced under the same conditions as in Reference Example 1-3 except that a different lot of soybean hypocotyl powder was used.

10 g of the equol-containing fermented soybean hypocotyl powder was added to 50 ml of a 50 vol. % aqueous ethanol solution, and two hours shaking was performed at room temperature. Thereafter, the residue ("Residue 1", hereinafter) was removed by centrifugation (2500 rpm, 25 minutes) to isolate a liquid extract ("Liquid Extract A-1", hereinafter). Next, 50 ml of a 50 vol. % aqueous ethanol solution was added to Residue 1, and an hour of shaking was performed at room temperature. Thereafter, the residue was removed by centrifugation (2500 rpm, 25 minutes) to isolate a liquid extract ("Liquid Extract A-2", hereinafter). Extracts A-1 and A-2 were mixed and then evaporated to dryness using an evaporator to obtain a residual solid ("Residual Solid 1", hereinafter).

Then, 10 ml of ethanol was added to Residual Solid 1, and 30 minutes of shaking was performed at room temperature under supersonic treatment. Thereafter, the residue was removed by centrifugation (1000 rpm, 10 minutes) to isolate a liquid extract ("Liquid Extract B", hereinafter). Liquid Extract B was evaporated to dryness using an evaporator to obtain about 1 g of a residual solid ("Residual Solid 2", hereinafter).

Next, 10 ml of hexane was added to the 1 g of Residual Solid 2, and 30 minutes of shaking was performed at room temperature. Then, the liquid extract was removed by centrifugation (1000 rpm, 10 minutes) to collect 0.3 g of insoluble residue.

2 ml of a mixed solution of hexane and dimethylether (hexane:dimethylether=2:3 (volume ratio)) was added to the obtained 0.3 mg of insoluble residue, and 30 minutes shaking was performed at room temperature. Then, the residue was removed by centrifugation (1000 rpm, 10 minutes) to collect a liquid extract. The obtained liquid extract was subjected to silica gel chromatography under the following conditions.

Column: A column 2 cm in internal diameter, filled with silica gel.

Mobile Phase:

200 ml of a mixed solution of hexane and diethylether (hexane:diethylether=40:60 (volume ratio));

200 ml of a mixed solution of hexane and diethylether (hexane:diethylether=30:70 (volume ratio));

200 ml of a mixed solution of hexane and diethylether (hexane:diethylether=25:75 (volume ratio));

200 ml of a mixed solution of hexane and diethylether (hexane:diethylether=20:80 (volume ratio));

and 200 ml of hexane were supplied sequentially.

Every 50 ml elution from the column was collected. The fraction eluted by the mixed solution of hexane and diethylether (hexane:diethylether=40:60 (volume ratio)) and the mixed solution of hexane and diethylether (hexane:diethylether=25:75 (volume ratio)) contained 40 mg of equol (recovery rate=80%), and the purity of equol was 99.9% per dry solid. FIG. 8 shows the TLC Analysis of the fraction eluted using silica gel chromatography. As shown in the figure, the fraction eluted by the mixed solution of hexane and diethylether (hexane:diethylether=30:70 (volume ratio)) and the mixed solution of hexane and diethylether (hexane:diethylether=25:75 (volume ratio)) contained equol with high purity. Table 11 details the samples supplied to the lanes of FIG. 8.

TABLE 11

| Lane in FIG. 8 | Sample Details |
|---|---|
| Lane 1 | Standard Product of Equol |
| Lane 2 | Elution Fraction obtained while the elution amount of Mixed Solution of Hexane and Diethylether (Hexane:Diethylether = 40:60 (Capacity Ratio)) ranges between 0 to 50 ml |
| Lane 3 | Elution Fraction obtained while the elution amount of Mixed Solution of Hexane and Diethylether (Hexane:Diethylether = 40:60 (Capacity Ratio)) ranges between 50 to 100 ml |
| Lane 4 | Elution Fraction obtained while the elution amount of Mixed Solution of Hexane and Diethylether (Hexane:Diethylether = 30:70 (Capacity Ratio)) ranges between 0 to 50 ml |
| Lane 5 | Elution Fraction obtained while the elution amount of Mixed Solution of Hexane and Diethylether (Hexane:Diethylether = 30:70 (Capacity Ratio)) ranges between 50 to 100 ml |
| Lane 6 | Elution Fraction obtained while the elution amount of Mixed Solution of Hexane and Diethylether (Hexane:Diethylether = 25:75 (Capacity Ratio)) ranges between 0 to 50 ml |
| Lane 7 | Elution Fraction obtained while the elution amount of Mixed Solution of Hexane and Diethylether (Hexane:Diethylether = 25:75 (Capacity Ratio)) ranges between 50 to 100 ml |
| Lane 8 | Elution Fraction obtained while the elution amount of Mixed Solution of Hexane and Diethylether (Hexane:Diethylether = 20:80 (Capacity Ratio)) ranges between 0 to 50 ml |

Example 2-2

Equol Purification Method 2

Equol-containing fermented soybean hypocotyl powder (equol concentration=6.2 mg/g) was produced under the same conditions as in Reference Example 1-3 except that a different lot of soybean hypocotyl powder was used.

100 g of the equol-containing fermented soybean hypocotyl powder was added to 500 ml of a 95 vol. % aqueous ethyl acetate solution, and four hours of stirring was performed at room temperature. Thereafter, insoluble residue were removed by filtration to collect an extract. The separated insoluble residue was washed with 80 ml of ethyl acetate, and the liquid after washing was mixed with the filtrate, and the mixture was concentrated under reduced pressure to collect 12 g of oily matter. The oily matter was subjected to silica gel chromatography.

Column: A column 2 cm in internal diameter, filled with 70 g of silica gel using hexane.

Mobile phase: Supplied with 500 ml of hexane, and a mixed solution of ethyl acetate and hexane (ethyl acetate: hexane=1:5 (volume ratio)) subsequently.

The solvent was distilled off from the equol-containing elution solvent thus collected, and 630 mg of a yellow crystalline solid was obtained.

The crystalline solid was added to 2 ml of ethyl acetate and dissolved by heating at 80° C. 8 ml of hexane was added thereto and 30 minutes of stirring was performed while cooling the mixture with ice to precipitate equol crystals. The obtained equol crystals were collected by filtration, and washed with hexane. Then the crystals were dried to obtain 530 mg of equol-containing solid (pale yellow crystals).

Further, the 530 mg equol-containing solid was added to 4 ml of aqueous ethanol solution (ethanol concentration=62.5 vol. %), and heated to 80° C. to be dissolved in the solution. The solution was allowed to stand for twelve hours at 10° C. to recrystallize equol, and then filtered and dried. As a result, 390 mg of white needle-shaped equol crystals were obtained.

The angle of rotation $[\alpha]_D^{25}$ of the obtained equol crystals was −21.6° in a 25° C. ethanol. The fusing point was 188-190° C. It was confirmed that the obtained equol was nearly 100% pure.

Example 3

Food Material Containing an Equol-Containing Fermented Soybean Hypocotyl or Extract Thereof, and Foods Containing the Food Material Example 3-1

Production of Food Material Containing an Equol-Containing Fermented Soybean Hypocotyl and Cacao Mass An equol-containing fermented soybean hypocotyl produced under the same conditions as in Reference Examples 1-3 was mixed with cacao mass having been dissolved by heat at a ratio of 1:3 (weight ratio). The mixture was cooled to obtain a food material in which an equol-containing fermented soybean hypocotyl is dispersed in cacao mass.

The taste of the food material thus produced was evaluated by 10 panelists, with the result that all of the panelists concluded that the bitter taste derived from the equol-containing fermented soybean hypocotyl was suppressed, and the food material possessed a pleasing flavor.

Example 3-2

Food Material Containing an Extract of Equol-Containing Fermented Soybean Hypocotyl A solid extract ("75Et extract", hereinafter) obtained by evaporating Liquid Extract 2-1 produced in Example 1-1 using 75Et was mixed with cacao mass having been dissolved by heat at a ratio of 1:24 (weight ratio). The mixture was cooled to obtain a food material in which a 75Et extract was dispersed in cacao mass.

The taste of the food material thus produced was evaluated by 10 panelists, with the result that all of the panelists concluded that the bitter taste derived from the 75Et extract was suppressed, and the food material possessed a pleasing flavor.

Example 3-3

Baked Confectionery

The ingredients shown in Table 12 were mixed, and the mixture was formed into a rectangle (about 1.5 cm×1.5 cm×10 cm) and baked in an oven at 180° C. to produce a baked confectionery.

The taste of the baked confectionery thus produced was evaluated by 10 panelists, with the result that all of the panelists concluded that the bitter taste derived from the equol-containing fermented soybean hypocotyl was suppressed, and the baked confectionery possessed a pleasing chocolate flavor and an original pleasing taste.

TABLE 12

|  | Proportion (wt. %) |
| --- | --- |
| Chip-shaped Food Material Obtained in Example 3-1 (about 0.1 g per chip) | 5 |
| Soy Flour | 25 |
| Raisins | q.s. |
| Butter | q.s. |
| Sugar | q.s. |
| Egg | q.s. |
| Orange Peel | q.s. |
| Pineapple | q.s. |
| Indigestible Dextrin | q.s. |
| *Cacao* Mass | q.s. |
| Sliced Almonds | q.s. |
| Cocoa Powder | q.s. |
| Salt | q.s. |
| Baking Powder | q.s. |
| Flavor | q.s. |
| Total | 100 |

Comparative Example 3-1

Baked Confectionery

A baked confectionery was produced under the same conditions as in Example 3-3 except that 1 g of the equol-containing fermented soybean hypocotyl produced under the same conditions as in Example 1-3 was mixed with 5 g of chocolate chips instead of the chip-shaped food material obtained in Example 3-1.

The taste of the baked confectionery thus produced was evaluated by 10 panelists, with the result that all of the panelists concluded that the pleasing taste disappeared and the bitter taste derived from the equol-containing fermented soybean hypocotyl remained throughout the confectionary.

Example 3-4

Baked Confectionery

A baked confectionery was produced under the same conditions as in Example 3-3 except for the inclusion of the same amount of chip-shaped food material obtained in Example 3-2 instead of the chip-shaped food materials obtained in Example 3-1.

The taste of the baked confectionery thus produced was evaluated by 10 panelists, with the result that all of the panelists concluded that the bitter taste derived from the 75Et extract was suppressed, and the baked confectionery possessed a pleasing chocolate flavor and an original pleasing taste.

Example 4

Food Comprising Equol-Containing Fermented Soybean Hypocotyl Material or Its Extract Example 4-A Beverage Hereinafter, specific production examples of the beverage according to the present invention are given.

Example 4-A-1

Sparkling Water

Sparkling water was obtained by preparing a mint-flavored syrup having the following composition, and mixing the resultant mint-flavored syrup with carbonated water in a volumetric ratio of 3:1.

Composition of Mint-Flavored Syrup

| Equol-containing fermented soybean hypocotyl material (Reference Example 1-3) | 0.27 (Kg) |
| --- | --- |
| Sugar | 0.60 |
| Citric acid (crystalline) | 0.01 |
| Table Salt | 0.012 |
| Potassium chloride | 0.005 |
| Calcium lactate | 0.008 |
| Peppermint extract | 0.03 |
| Peppermint flavor | 0.20 |
| Water | Balance |
| Total | 100.00 L |

Example 4-A-2

Sparkling Water

Sparkling water was produced under the same conditions as in Example 4-A-1, except that the mint-flavored syrup was prepared by adding, instead of the equol-containing fermented soybean hypocotyl material, 0.034 kg of the solid extract prepared in Example 1-1 by evaporating Liquid Extract 1-2 obtained using 75Et to dryness.

Example 4-A-3

Orange-Flavored Carbonated Beverage Containing No Orange Juice

An orange-flavored carbonated beverage containing no orange juice was obtained by preparing an orange-flavored syrup having the following composition, and mixing the resultant orange-flavored syrup with carbonated water in a volumetric ratio of 9:11.
Composition of Orange-Flavored Syrup

| | |
|---|---|
| Equol-containing fermented soybean hypocotyl material (Reference-Example 1-3) | 0.20 (Kg) |
| Sugar | 10.00 |
| Citric acid (crystalline) | 0.03 |
| DL-malic acid | 0.07 |
| Food coloring | 0.05 |
| Flavor | 0.10 |
| Water | Balance |
| Total | 45.00 L |

Example 4-A-4

Orange-Flavored Carbonated Beverage Containing No Orange Juice

An orange-flavored carbonated beverage containing no orange juice was produced under the same conditions as in Example 4-A-3, except that the orange-flavored syrup was prepared by adding, instead of the equol-containing fermented soybean hypocotyl material, 0.025 kg of the solid extract prepared in Example 1-1 by evaporating Liquid Extract 1-2 obtained using 75Et to dryness.

Example 4-A-5

Low-Calorie Cola

Sugarless cola was obtained by preparing a cola syrup having the following composition, and mixing the resultant cola syrup with carbonated water in a volumetric ratio of 8:12.
Composition of Cola Syrup

| | |
|---|---|
| Equol-containing fermented soybean hypocotyl material (Reference Example 1-2) | 0.20 (Kg) |
| Sucralose | 0.02 |
| Phosphoric acid | 0.05 |
| Citric acid (crystalline) | 0.07 |
| Caffeine | 0.10 |
| Caramel coloring | 0.20 |
| Flavor (cola flavor) | 0.10 |
| Water | Balance |
| Total | 40.00 L |

Example 4-A-6

Low-Calorie Cola

Low-calorie cola was produced under the same conditions as in Example 4-A-5, except that the cola syrup was prepared by adding, instead of the equol-containing fermented soybean hypocotyl material, 0.03 kg of the solid extract prepared in Example 1-1 by evaporating Liquid Extract 1-2 obtained using 75Et to dryness.

Example 4-A-7

Carbonated Apple Beverage

A carbonated apple beverage was obtained by preparing apple-flavored syrup having the following composition, and mixing the resultant apple-flavored syrup with carbonated water in a volumetric ratio of 13:7.
Composition of Apple-Flavored Syrup

| | |
|---|---|
| Equol-containing fermented soybean hypocotyl material (Reference Example 1-2) | 0.20 (Kg) |
| 5 times concentrated apple juice | 11.00 |
| Fructose/glucose syrup | 5.00 |
| Citric acid (crystalline) | 0.10 |
| Food coloring | 0.05 |
| Flavor | 0.10 |
| Water | Balance |
| Total | 65.00 L |

Example 4-A-8

Carbonated Apple Beverage

A carbonated apple beverage was produced under the same conditions as in Example 4-A-7, except that the apple-flavored syrup was prepared by adding, instead of the equol-containing fermented soybean hypocotyl material, 0.03 kg of the solid extract prepared in Example 1-1 by evaporating Liquid Extract 1-2 obtained using 75Et to dryness.

Example 4-A-9

Carbonated Grape Beverage

A carbonated grape beverage was obtained by preparing a grape-flavored syrup having the following composition, and mixing the resultant grape-flavored syrup with carbonated water in a volumetric ratio of 9:11.
Composition of Grape-Flavored Syrup

| | |
|---|---|
| Equol-containing fermented soybean hypocotyl material (Reference Example 1-1) | 0.20 (Kg) |
| 5 times concentrated clear grape juice | 4.40 |
| Citric acid (crystalline) | 0.25 |
| Food coloring | 0.05 |
| Flavor | 0.20 |
| Water | Balance |
| Total | 45.00 L |

Example 4-A-10

Carbonated Grape Beverage

A carbonated grape beverage was produced under the same conditions as in Example 4-A-9, except that the grape-flavored syrup was prepared by adding, instead of the equol-containing fermented soybean hypocotyl material, 0.03 kg of the solid extract prepared in Example 1-1 by evaporating Liquid Extract 1-2 obtained using 75Et to dryness.

Example 4-A-11

Beverage Containing Apple Juice

A beverage containing apple juice having the following composition was produced.

| | |
|---|---|
| Equol-containing fermented soybean hypocotyl material (Reference Example 1-3) | 0.40 (Kg) |
| 5 times concentrated apple juice | 22.00 |
| Flavor | 0.05 |
| Water | Balance |
| Total | 100.00 L |

Example 4-A-12

Beverage Containing Apple Juice

A beverage containing apple juice was produced under the same conditions as in Example 4-A-11, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-13

Beverage Containing Orange Juice

A beverage containing orange juice having the following composition was produced.

| | |
|---|---|
| Equol-containing fermented soybean hypocotyl material (Reference Example 1-3) | 0.40 (Kg) |
| Concentrated Valencia orange juice (Brix: 55 degree) | 4.40 |
| Sugar | 5.00 |
| Citric acid (crystalline) | 0.16 |
| Native gellan gum | 0.025 |
| Vitamin C | 0.03 |
| Pectin | 0.0025 |
| Orange flavor | 0.25 |
| Water | Balance |
| Total | 100.00 L |

Example 4-A-14

Beverage Containing Orange Juice

A beverage containing orange juice was produced under the same conditions as in Example 4-A-13, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-15

Low-Calorie Beverage Containing Fruit Juice

A low-calorie beverage containing fruit juice having the following composition was produced.

| | |
|---|---|
| Equol-containing fermented soybean hypocotyl material (Reference Example 1-1) | 0.40 (Kg) |
| 5 times concentrated citrus juice | 4.40 |
| Sucralose | 0.009 |
| Citric acid (crystalline) | 0.18 |
| L-ascorbic acid | 0.03 |
| Gellan gum | 0.024 |
| Flavor | 0.10 |
| Water | Balance |
| Total | 100.00 L |

Example 4-A-16

Low-Calorie Beverage Containing Fruit Juice

A low-calorie beverage containing fruit juice was produced under the same conditions as in Example 4-A-15, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-17

Sugarless Near Water (Soft Drink Similar to Water)

Sugarless near water (soft drink similar to water) having the following composition was produced.

| | |
|---|---|
| Equol-containing fermented soybean hypocotyl material (Reference Example 1-3) | 0.40 (Kg) |
| Sucralose | 0.008 |
| Polydextrose | 2.20 |
| 5 times concentrated grapefruit juice | 0.44 |
| Citric acid (crystalline) | 0.53 |
| Calcium lactate | 0.06 |
| Potassium chloride | 0.01 |
| L-ascorbic acid | 0.03 |
| Dibenzoyl thiamine hydrochloride | 0.0002 |
| Pyridoxine hydrochloride | 0.00015 |
| Nicotinamide | 0.0015 |
| Flavor | 0.10 |
| Water | Balance |
| Total | 100.00 L |

Example 4-A-18

Sugarless Near Water (Soft Drink Similar to Water)

Sugarless near water (soft drink similar to water) was produced under the same conditions as in Example 4-A-17, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-19

Sports Drink

A sports drink having the following composition was produced.

| | |
|---|---|
| Equol-containing fermented soybean hypocotyl material (Reference Example 1-2) | 0.40 (Kg) |
| Clear lemon juice | 0.50 |

-continued

| | |
|---|---|
| Sucralose | 0.02 |
| Lactic minerals | 1.00 |
| Vitamin mix | 0.25 |
| Sodium L-ascorbate | 0.05 |
| Citric acid | 0.125 |
| Water | Balance |
| Total | 100.00 L |

Example 4-A-20

Sports Drink

A sports drink was produced under the same conditions as in Example 4-A-19, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-21

Powdered Green Tea-Milk Drink

A powdered green tea-milk drink having the following composition was produced.

| | |
|---|---|
| Equol-containing fermented soybean hypocotyl material (Reference Example 1-2) | 0.40 (Kg) |
| Cow's milk | 10.00 |
| Skimmed milk | 3.50 |
| Powdered green tea (RS-20, produced by ITO EN, LTD.) | 0.50 |
| Sugar | 7.00 |
| Emulsifier | 0.70 |
| Food coloring | 0.03 |
| Flavor | 0.20 |
| Sodium hydrogen carbonate | for adjusting pH to 6.8 |
| Water | Balance |
| Total | 100.00 L |

Example 4-A-22

Powdered Green Tea-Milk Drink

A powdered green tea-milk drink was produced under the same conditions as in Example 4-A-21, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-23

Sugarless Yogurt Drink

A sugarless yogurt drink having the following composition was produced.

| | |
|---|---|
| Equol-containing fermented soybean hypocotyl material (Reference Example 1-3) | 0.40 (Kg) |
| Fermented milk (SNF20%) | 40.00 |
| Water-soluble soybean polysaccharide | 0.20 |
| Pectin | 0.20 |
| Flavor | 0.20 |
| Lactic acid | for adjusting pH to 4.2 |
| Water | Balance |
| Total | 100.00 L |

Example 4-A-24

Sugarless Yogurt Drink

A sugarless yogurt drink was produced under the same conditions as in Example 4-A-23, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-25

Pasteurized Lactic Acid Bacteria Beverage

A pasteurized lactic acid bacteria beverage having the following composition was produced.

| | |
|---|---|
| Equol-containing fermented soybean hypocotyl material (Reference Example 1-3) | 0.40 (Kg) |
| Fermented milk (SNF20%) | 15.00 |
| Water-soluble soybean polysaccharide | 0.40 |
| Sugar | 8.00 |
| Flavor | 0.10 |
| Lactic acid | for adjusting pH to 3.8 |
| Water | Balance |
| Total | 100.00 L |

Example 4-A-26

Pasteurized Lactic Acid Bacteria Beverage

A pasteurized lactic acid bacteria beverage was produced under the same conditions as in Example 4-A-25, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-27

Low-Calorie Sour Milk Beverage

A low-calorie sour milk beverage having the following composition was produced.

| | |
|---|---|
| Equol-containing fermented soybean hypocotyl material (Reference Example 1-3) | 0.40 (Kg) |
| Skimmed milk | 3.50 |
| Water-soluble soybean polysaccharide | 0.40 |
| Sugar | 5.00 |
| Sucralose | 0.0006 |
| Fructose/glucose syrup (75%) | 5.00 |
| Citric acid (crystalline) | 0.45 |
| Flavor | 0.10 |
| Lactic acid | for adjusting pH to 3.8 |
| Water | Balance |
| Total | 100.00 L |

Example 4-A-28

Low-Calorie Sour Milk Beverage

Low-calorie sour milk beverage was produced under the same conditions as in Example 4-A-27, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-29

Strawberry-Flavored Milk Drink

A strawberry-flavored milk drink having the following composition was produced.

| | |
|---|---|
| Equol-containing fermented soybean hypocotyl material (Reference Example 1-3) | 0.40 (Kg) |
| Skimmed milk | 2.80 |
| Whole milk powder | 3.00 |
| Sugar | 12.00 |
| Emulsifier | 0.06 |
| Food coloring | 0.05 |
| Flavor (strawberry flavor) | 0.10 |
| Water | Balance |
| Total | 100.00 L |

Example 4-A-30

Strawberry-Flavored Milk Drink

Strawberry-flavored milk drink was produced under the same conditions as in Example 4-A-29, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-31

Non-Fat Milk

Non-fat milk having the following composition was produced.

| | |
|---|---|
| Equol-containing fermented soybean hypocotyl material (Reference Example 1-1) | 0.40 (Kg) |
| Skimmed milk | 12.00 |
| Egg calcium | 1.00 |
| Emulsifier | 0.06 |
| Flavor | 0.10 |
| Water | Balance |
| Total | 100.00 L |

Example 4-A-32

Non-Fat Milk

Non-fat milk was produced under the same conditions as in Example 4-A-31, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-33

Cream Soda

A cream soda having the following composition was produced.

| | |
|---|---|
| Equol-containing fermented soybean hypocotyl material (Reference Example 1-1) | 0.20 (Kg) |
| Skimmed sweetened condensed milk | 3.00 |
| Citric acid (crystalline) | 0.04 |
| Sugar | 15.00 |
| Food coloring | 0.60 |
| Flavor | 0.10 |
| Water | Balance |
| Total | 40.00 L |

Example 4-A-34

Cream Soda

A cream soda was produced under the same conditions as in Example 4-A-33, except for using, instead of the equol-containing fermented soybean hypocotyl material, 0.025 kg of the solid extract prepared in Example 1-1 by evaporating Liquid Extract 1-2 obtained using 75Et to dryness.

Example 4-A-35

Powdered Green Tea-Milk Drink

A powdered green tea-milk drink having the following composition was produced.

| | |
|---|---|
| Equol-containing fermented soybean hypocotyl material (Reference Example 1-2) | 0.40 (Kg) |
| Skimmed milk | 3.50 |
| Cow's milk | 10.00 |
| Emulsifier | 0.70 |
| Sugar | 6.00 |
| Water | Balance |
| Total | 100.00 L |

Example 4-A-36

Powdered Green Tea-Milk Drink

Powdered green tea-milk drink was produced under the same conditions as in Example 4-A-35, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-37

Black Tea

Black tea having the following composition was produced.

| | |
|---|---|
| Equol-containing fermented soybean hypocotyl material (Reference Example 1-2) | 0.40 (Kg) |
| Darjeeling tea extract (40 times) | 20.00 |
| Sugar | 5.00 |
| Flavor | 0.05 |
| Water | Balance |
| Total | 100.00 L |

Example 4-A-38

Black Tea

Black tea was produced under the same conditions as in Example 4-A-37, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-39

Beverage Containing Apple Juice

A beverage containing apple juice having the following composition was produced.

| | |
|---|---|
| Equol-containing fermented soybean hypocotyl material (Reference Example 1-3) | 0.40 (Kg) |
| 5 times concentrated clear apple juice | 2.20 |
| Oligosaccharide | 1.00 |
| Reducing maltose syrup | 1.50 |
| Vitamin C | 0.05 |
| Citric acid | 0.10 |
| Water-soluble dietary fiber | 8.00 |
| Water | Balance |
| Total | 100.00 L |

Example 4-A-40

Beverage Containing Apple Juice

A beverage containing apple juice was produced under the same conditions as in Example 4-A-39, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-41

Soft Drink

A soft drink having the following composition was produced.

| | |
|---|---|
| Equol-containing fermented soybean hypocotyl material (Reference Example 1-3) | 0.40 (Kg) |
| Fructose | 3.70 |
| Fructose/glucose syrup | 8.00 |
| Sugar | 0.30 |
| DL-malic acid | 0.07 |
| Sodium citrate | 0.03 |
| Emulsifier | 0.052 |
| Flavor | 0.22 |
| Water | Balance |
| Total | 100.00 L |

Example 4-A-42

Soft Drink

A soft drink was produced under the same conditions as in Example 4-A-41, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-43

Beverage Containing Orange Juice

A beverage containing orange juice having the following composition was produced.

| | |
|---|---|
| Equol-containing fermented soybean hypocotyl material (Reference Example 1-3) | 0.40 (Kg) |
| Fructose/glucose syrup | 2.50 |
| Beet oligosaccharide | 0.026 |
| Sugar | 4.00 |
| Concentrated orange juice | 4.40 |
| Citric acid | 0.026 |
| Sodium citrate | 0.003 |
| L-ascorbic acid | 0.01 |
| Flavor | 0.10 |
| Water | Balance |
| Total | 100.00 L |

Example 4-A-44

Beverage Containing Orange Juice

A beverage containing orange juice was produced under the same conditions as in Example 4-A-43, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-45

Beverage Containing Apple Juice

A beverage containing apple juice having the following composition was produced.

| | |
|---|---|
| Equol-containing fermented soybean hypocotyl material (Reference Example 1-3) | 0.40 (Kg) |
| Concentrated apple juice | 4.40 |
| Sugar | 8.00 |
| Citric acid | 0.15 |
| Flavor | 0.12 |
| Water | Balance |
| Total | 100.00 L |

Example 4-A-46

Beverage Containing Apple Juice

A beverage containing apple juice was produced under the same conditions as in Example 4-A-45, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-47-1

Vegetable Juice

Vegetable juice having the following composition was produced.

| | |
|---|---|
| Equol-containing fermented soybean hypocotyl material (Reference Example 1-2) | 0.40 (Kg) |
| Vegetable fruit juice | 20.00 |
| Water | Balance |
| Total | 100.00 L |

Example 4-A-47-2

Vegetable Juice

Vegetable juice was produced under the same conditions as in Example 4-A-47-1, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-48-1

Sports Drink

A sports drink having the following composition was produced.

| | |
|---|---|
| Equol-containing fermented soybean hypocotyl material (Reference Example 1-2) | 0.40 (Kg) |
| Lactic minerals | 1.00 |
| Vitamin mix | 0.25 |
| Citric acid | 0.125 |
| Sodium L-ascorbate | 0.05 |
| Lemon juice | 0.50 |
| Sugar | 12.00 |
| Water | Balance |
| Total | 100.00 L |

Example 4-A-48-2

Sports Drink

A sports drink was produced under the same conditions as in Example 4-A-48-1, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-49

Oolong Tea

Oolong tea having the following composition was produced.

| | |
|---|---|
| Equol-containing fermented soybean hypocotyl material (Reference Example 1-3) | 0.40 (Kg) |
| Oolong tea extract | 3.00 |
| Sodium L-ascorbate | 0.01 |
| Flavor | 0.20 |
| Water | Balance |
| Total | 100.00 L |

Example 4-A-50

Oolong Tea

Oolong tea was produced under the same conditions as in Example 4-A-49, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-51

Tea with Lemon

Tea with lemon having the following composition was produced.

| | |
|---|---|
| Equol-containing fermented soybean hypocotyl material (Reference Example 1-3) | 0.40 (Kg) |
| Black tea extract | 6.00 |
| Reducing maltose syrup powder | 3.00 |
| Sugar | 3.00 |
| Lemon juice | 0.50 |
| L-ascorbic acid | 0.02 |
| Flavor | 0.10 |
| Water | Balance |
| Total | 100.00 L |

Example 4-A-52

Tea with Lemon

Tea with lemon was produced under the same conditions as in Example 4-A-51, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-53

Tea with Milk

Tea with milk having the following composition was produced.

| | |
|---|---|
| Equol-containing fermented soybean hypocotyl material (Reference Example 1-3) | 0.40 (Kg) |
| Cow's milk | 7.00 |
| Whole milk powder | 0.25 |
| Sugar | 4.00 |
| Tea extract | 35.00 |
| Emulsifier | 0.05 |
| Flavor | 0.10 |
| Water | Balance |
| Total | 100.00 L |

Example 4-A-54

Tea with Milk

Tea with milk was produced under the same conditions as in Example 4-A-53, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-55

Coffee Drink

A coffee drink having the following composition was produced.

| | |
|---|---|
| Equol-containing fermented soybean hypocotyl material (Reference Example 1-1) | 0.40 (Kg) |
| Coffee extract | 30.00 |
| Cow's milk | 25.00 |
| Emulsifier | 0.10 |
| Sodium bicarbonate | 0.12 |
| *Stevia* | 0.01 |
| Sugar | 3.00 |
| L-rhamnose | 0.01 |
| Flavor | 0.05 |
| Water | Balance |
| Total | 100.00 L |

Example 4-A-56

Coffee Drink

A coffee drink was produced under the same conditions as in Example 4-A-55, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-57

Cocoa Milk Drink

A Cocoa milk drink having the following composition was produced.

| | |
|---|---|
| Equol-containing fermented soybean hypocotyl material (Reference Example 1-1) | 0.40 (Kg) |
| Cow's milk | 10.00 |
| Skimmed milk | 3.50 |
| Fructose | 5.50 |
| Sugar | 0.40 |

-continued

| | |
|---|---|
| Cocoa powder | 1.00 |
| Emulsifier | 0.45 |
| Flavor | 0.08 |
| Water | Balance |
| Total | 100.00 L |

Example 4-A-58

Cocoa Milk Drink

A cocoa milk drink was produced under the same conditions as in Example 4-A-57, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-59

Powdered Green Tea-Milk Drink

A powdered green tea-milk drink having the following composition was produced.

| | |
|---|---|
| Equol-containing fermented soybean hypocotyl material (Reference Example 1-1) | 0.40 (Kg) |
| Cow's milk | 10.00 |
| Skimmed milk | 3.50 |
| Fructose | 5.80 |
| Sugar | 0.40 |
| Powdered green tea | 0.90 |
| Emulsifier | 0.48 |
| Flavor | 0.27 |
| Food coloring | 0.03 |
| Water | Balance |
| Total | 100.00 L |

Example 4-A-60

Powdered Green Tea-Milk Drink

A powdered green tea-milk drink was produced under the same conditions as in Example 4-A-59, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-61

Sour Milk Beverage

A sour milk beverage having the following composition was produced.

| | |
|---|---|
| Equol-containing fermented soybean hypocotyl material (Reference Example 1-3) | 0.40 (Kg) |
| Skimmed milk | 1.50 |
| Fructose | 2.50 |
| Sugar | 0.50 |
| Concentrated strawberry juice | 0.22 |
| Sodium citrate | 0.32 |

-continued

| | |
|---|---|
| Emulsifier | 0.40 |
| Flavor | 0.12 |
| Water | Balance |
| Total | 100.00 L |

Example 4-A-62

Sour Milk Beverage

A sour milk beverage was produced under the same conditions as in Example 4-A-61, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-63

Beverage Containing Vitamins

A beverage containing vitamins having the following composition was produced.

| | |
|---|---|
| Equol-containing fermented soybean hypocotyl material (Reference Example 1-3) | 0.40 (Kg) |
| Sugar | 24.00 |
| Citric acid | 0.20 |
| L-ascorbic acid | 0.30 |
| Vitamin mix | 0.06 |
| Flavor | 0.10 |
| Carbonated water | Balance |
| Total | 100.00 L |

Example 4-A-64

Beverage Containing Vitamins

A beverage containing vitamins was produced under the same conditions as in Example 4-A-63, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-65

Red Bean Soup

A red bean soup of the following composition was produced.

| | |
|---|---|
| Equol-containing fermented soybean hypocotyl material (Reference Example 1-3) | 0.40 (Kg) |
| Red bean paste | 10.00 |
| Sugar alcohol | 6.50 |
| Sugar | 24.00 |
| Table salt | 0.10 |
| Emulsifier | 0.60 |
| Flavor | 0.10 |
| Water | Balance |
| Total | 100.00 L |

Example 4-A-66

Red Bean Soup

A red bean soup was produced under the same conditions as in Example 4-A-65, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-67

Green Tea

Green tea having the following composition was produced.

| | |
|---|---|
| Equol-containing fermented soybean hypocotyl material (Reference Example 1-1) | 0.40 (Kg) |
| Green tea extract | 3.00 |
| Sodium L-ascorbate | 0.01 |
| Flavor | 0.20 |
| Water | Balance |
| Total | 100.00 L |

Example 4-A-68

Green Tea

Green tea was produced under the same conditions as in Example 4-A-67, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-69

Powdered Orange Juice Drink

A powdered orange juice drink having the following composition was produced.

| | |
|---|---|
| Equol-containing fermented soybean hypocotyl material (Reference Example 1-2) | 0.40 (Kg) |
| Fructose/glucose syrup | 2.50 |
| Beet oligosaccharide | 0.026 |
| Sugar | 4.00 |
| Powdered orange juice | 2.00 |
| Citric acid | 0.026 |
| Sodium citrate | 0.003 |
| L-ascorbic acid | 0.01 |
| Flavor | 0.10 |
| Water | Balance |
| Total | 100.00 L |

Example 4-A-70

Powdered Orange Juice Drink

A powdered orange juice drink was produced under the same conditions as in Example 4-A-69, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-71

Amino Acid Drink

An amino acid drink having the following composition was produced.

| | |
|---|---|
| Equol-containing fermented soybean hypocotyl material (Reference Example 1-3) | 0.40 (Kg) |
| Sugar | 15.00 |
| Fructose | 15.00 |
| Citric acid | 4.00 |
| Sodium citrate | 1.00 |
| L-valine | 2.00 |
| L-leucine | 4.00 |
| L-isoleucine | 2.00 |
| L-arginine | 2.00 |
| Flavor | 0.10 |
| Water | Balance |
| Total | 100.00 L |

Example 4-A-72

Amino Acid Drink

An amino acid drink was produced under the same conditions as in Example 4-A-71, except for using, instead of the equol-containing fermented soybean hypocotyl material, 0.05 kg of the solid extract prepared in Example 1-1 by evaporating Liquid Extract 1-2 obtained using 75Et to dryness.

Example 4-A-73

Soya Milk Drink

A soya milk drink having the following composition was produced.

| | |
|---|---|
| Equol-containing fermented soybean hypocotyl material (Reference Example 1-3) | 0.40 (part by weight) |
| Soya Milk | 100.00 |

Example 4-A-74

Soya Milk Drink

A soya milk drink was produced under the same conditions as in Example 4-A-73, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-A-75

Energy Drink

An energy drink having the following composition was produced.

| | |
|---|---|
| Equol-containing fermented soybean hypocotyl material (Reference Example 1-3) | 0.40 (Kg) |
| Taurine | 1.00 |
| Nicotinamide | 0.02 |
| Vitamin B1 | 0.005 |
| Vitamin B2 | 0.005 |
| Vitamin B6 | 0.005 |
| Caffeine | 0.05 |
| Sugar | 15.00 |
| Fructose | 15.00 |
| Citric acid | 0.10 |
| Flavor | 0.10 |
| Water | Balance |
| Total | 100.00 L |

Example 4-A-76

Amino Acid Drink

An amino acid drink was produced under the same conditions as in Example 4-A-75, except for using, instead of the equol-containing fermented soybean hypocotyl material, 0.05 kg of the solid extract prepared in Example 1-1 by evaporating Liquid Extract 1-2 obtained using 75Et to dryness.

Example 4-B

Dietary Supplement

Hereinafter, specific production examples of the dietary supplement according to the present invention are given.

Example 4-B-1

Softgel

A softgel was produced according to a known method using equol-containing fermented soybean hypocotyl material (Reference Example 1-3), gelatin, glycerine, citric acid, soybean oil, beeswax, lecithin, β carotene, and water.

Example 4-B-2

Softgel

A softgel was produced under the same conditions as in Example 4-B-1, except for using, instead of the equol-containing fermented soybean hypocotyl material, the solid extract prepared in Example 1-1 by evaporating Liquid Extract 1-2 obtained using 75Et to dryness.

Example 4-C

Creamy Food

Hereinafter, specific production examples of the creamy food according to the present invention are given.

Example 4-C-1

Whipped Cream

Whipped cream having the following composition was produced.

| | |
|---|---|
| Equol-containing fermented soybean hypocotyl material (Reference Example 1-3) | 0.40 (g) |
| Coconut oil (mp: 35° C.) | 27.00 |
| Glycerine fatty acid ester | 0.10 |
| Skimmed milk | 3.30 |
| Sucralose | 0.012 |
| Reducing starch sugar | 25.00 |
| Lecithin | 0.15 |
| Emulsifier | 0.70 |
| Sodium metaphosphate | 0.10 |
| Water | Balance |
| Total | 100.00 g |

Example 4-C-2

Whipped Cream

Whipped cream was produced under the same conditions as in Example 4-C-1, except for using, instead of the equol-containing fermented soybean hypocotyl material, 0.05 g of the solid extract prepared in Example 1-1 by evaporating Liquid Extract 1-2 obtained using 75Et to dryness.

Example 4-C-3

Coffee Whitener

A coffee whitener having the following composition was produced.

| | |
|---|---|
| Equol-containing fermented soybean hypocotyl material (Reference Example 1-3) | 0.40 (g) |
| Purified coconut oil | 36.00 |
| Sodium casein | 4.50 |
| Skimmed milk | 5.00 |
| Lecithin | 0.05 |
| Trisodium citrate | 0.20 |
| Sucrose fatty acid ester | 0.40 |
| Milk flavor | 0.10 |
| Water | Balance |
| Total | 100.00 g |

Example 4-C-4

Coffee Whitener

A coffee whitener was produced under the same conditions as in Example 4-C-3, except for using, instead of the equol-containing fermented soybean hypocotyl material, 0.05 g of the solid extract prepared in Example 1-1 by evaporating Liquid Extract 1-2 obtained using 75Et to dryness.

Example 4-C-5

Custard

Custard having the following composition was produced.

| | |
|---|---|
| Equol-containing fermented soybean hypocotyl material (Reference Example 1-3) | 0.40 (Kg) |
| Margarine | 20.00 |
| Starch syrup | 5.00 |
| Whole egg | 3.00 |
| Cornstarch | 4.00 |
| Modified starch | 6.00 |
| Lactic protein | 2.00 |
| Sugar | 30.00 |
| Water | Balance |
| Total | 100.00 kg |

Example 4-C-6

Custard

Custard was produced under the same conditions as in Example 4-C-5, except for using, instead of the equol-containing fermented soybean hypocotyl material, 0.05 kg of the solid extract prepared in Example 1-1 by evaporating Liquid Extract 1-2 obtained using 75Et to dryness.

Example 4-C-7

Custard

Custard having the following composition was produced.

| | |
|---|---|
| Equol-containing fermented soybean hypocotyl material (Reference Example 1-3) | 0.40 (Kg) |
| Carrageenan | 0.40 |
| Gelatin | 0.50 |
| Cornstarch | 4.00 |
| Corn syrup solids | 3.00 |
| Granulated sugar | 10.00 |
| Glucose | 7.00 |
| Skimmed milk | 4.00 |
| Whole egg | 3.50 |
| Isomerized sugar | 7.00 |
| Skimmed sweetened condensed milk | 3.00 |
| Unsalted butter | 6.50 |
| Water | 50.00 |

Example 4-C-8

Custard

Custard was produced under the same conditions as in Example 4-C-7, except for using, instead of the equol-containing fermented soybean hypocotyl material, 0.05 kg of the solid extract prepared in Example 1-1 by evaporating Liquid Extract 1-2 obtained using 75Et to dryness.

Example 4-D

Dessert

Hereinafter, specific production examples of the dessert according to the present invention are given.

Example 4-D-1

Hard Yogurt

The ingredients of the following composition were homogenized, and a starter yogurt was added thereto to be fermented, thereby producing hard yogurt.

| | |
|---|---|
| Equol-containing fermented soybean hypocotyl material (Reference Example 1-3) | 0.40 (Kg) |
| Skimmed milk | 9.00 |
| Unsalted butter | 5.00 |
| Sugar | 6.50 |
| Gelling agent | 0.60 |
| Water | Balance |
| Total | 100.00 kg |

Example 4-D-2

Hard Yogurt

Hard yogurt was produced under the same conditions as in Example 4-D-1, except for using, instead of the equol-containing fermented soybean hypocotyl material, 0.05 kg of the solid extract prepared in Example 1-1 by evaporating Liquid Extract 1-2 obtained using 75Et to dryness.

Example 4-D-3

Soft Yogurt

The ingredients of the following composition were homogenized, and a starter yogurt was added thereto to be fermented, thereby producing soft yogurt.

| | |
|---|---|
| Equol-containing fermented soybean hypocotyl material (Reference Example 1-3) | 0.40 (Kg) |
| Skimmed milk | 9.00 |
| Butter | 5.25 |
| Sugar | 6.50 |
| Locust bean gum | 0.30 |
| Water | Balance |
| Total | 100.00 kg |

Example 4-D-4

Soft Yogurt

Soft yogurt was produced under the same conditions as in Example 4-D-3, except for using, instead of the equol-containing fermented soybean hypocotyl material, 0.05 kg of the solid extract prepared in Example 1-1 by evaporating Liquid Extract 1-2 obtained using 75Et to dryness.

Example 4-D-5

White Peach Jelly

A white peach jelly was produced in accordance with a general production method of a jelly, using the ingredients of the following composition.

| | |
|---|---|
| Equol-containing fermented soybean hypocotyl material (Reference Example 1-3) | 0.40 (part by weight) |
| Sugar | 14.40 |
| κ-Carrageenan | 0.60 |
| White peach puree | 20.00 |
| Water | Balance |
| Total | 100.00 parts by weight |

Example 4-D-6

White Peach Jelly

A white peach jelly was produced under the same conditions as in Example 4-D-5, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-D-7

Grapefruit Jelly

A grapefruit jelly was produced in accordance with a general production method of a jelly, using the ingredients of the following composition.

| | |
|---|---|
| Equol-containing fermented soybean hypocotyl material (Reference Example 1-2) | 0.40 (part by weight) |
| Sugar | 18.00 |
| Gellan gum | 0.25 |
| Grapefruit juice | 20.00 |
| Calcium lactate | 0.10 |
| Citric acid | 0.20 |
| Flavor | 0.10 |
| Water | Balance |
| Total | 100.00 parts by weight |

Example 4-D-8

Grapefruit Jelly

A grapefruit jelly was produced under the same conditions as in Example 4-D-7, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-D-9

Coffee Jelly

A coffee jelly was produced in accordance with a general production method of a jelly, using the ingredients of the following composition.

| | |
|---|---|
| Equol-containing fermented soybean hypocotyl material (Reference Example 1-2) | 0.40 (part by weight) |
| Reducing starch syrup | 10.00 |
| Xylitol | 5.00 |
| κ-Carrageenan | 0.50 |
| Agar | 0.20 |
| Locust bean gum | 0.20 |
| Sugar | 3.00 |
| Flavor | 0.15 |
| Water | Balance |
| Total | 100.00 parts by weight |

Example 4-D-10

Coffee Jelly

A coffee jelly was produced under the same conditions as in Example 4-D-9, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-D-11

Strawberry Milk Jelly

A strawberry milk jelly was produced in accordance with a general production method of a jelly, using the ingredients of the following composition.

| | |
|---|---|
| Equol-containing fermented soybean hypocotyl material (Reference Example 1-2) | 0.40 (part by weight) |
| Purified coconut oil | 30.00 |
| Emulsifier | 0.25 |
| Skimmed milk | 3.30 |
| Sugar | 3.50 |
| Reducing starch syrup | 20.00 |
| Lactitol | 8.00 |
| Stabilizer | 0.70 |
| Xylitol | 5.00 |
| Gelatin | 0.90 |
| Strawberry puree | 5.00 |
| Concentrated strawberry juice | 5.00 |
| Citric acid | 0.10 |
| Water | Balance |
| Total | 100.00 parts by weight |

Example 4-D-12

Strawberry Milk Jelly

A strawberry milk jelly was produced under the same conditions as in Example 4-D-11, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E

Snack

Hereinafter, specific production examples of the snack according to the present invention are given.

Example 4-E-1

Hard Candy

A hard candy was produced in accordance with a general production method of a hard candy, using the ingredients of the following composition.

| | |
|---|---|
| Equol-containing fermented soybean hypocotyl material (Reference Example 1-3) | 4.00 (g) |
| Sugar | 70.00 |
| Starch syrup | 40.00 |
| Water | 20.00 |

Example 4-E-2

Hard Candy

A hard candy was produced under the same conditions as in Example 4-E-1, except for using, instead of the equol-containing fermented soybean hypocotyl material, 0.5 g of the solid extract prepared in Example 1-1 by evaporating Liquid Extract 1-2 obtained using 75Et to dryness.

Example 4-E-3

Ginger Candy

A ginger candy was produced in accordance with a general production method of a candy, using the ingredients of the following composition.

| | |
|---|---|
| Equol-containing fermented soybean hypocotyl material (Reference Example 1-1) | 4.00 (g) |
| Ginger paste | 1.50 |
| Reducing lactose | 60.00 |
| Reducing maltose syrup | 56.00 |
| Sucralose | 0.03 |
| Flavor | 0.075 |
| Water | 30.00 |

Example 4-E-4

Ginger Candy

A ginger candy was produced under the same conditions as in Example 4-E-3, except for using, instead of the equol-containing fermented soybean hypocotyl material, 0.5 g of the solid extract prepared in Example 1-1 by evaporating Liquid Extract 1-2 obtained using 75Et to dryness.

Example 4-E-5

Throat Soothing Herb Candy

A throat soothing herb candy was produced in accordance with a general production method of a candy, using the ingredients of the following composition.

| | |
|---|---|
| Equol-containing fermented soybean hypocotyl material (Reference Example 1-2) | 4.00 (g) |
| Mixed herb extract | 0.60 |
| Sugar | 40.00 |
| Reducing maltose syrup | 56.00 |
| Peppermint Flavor | 0.20 |
| Caramel coloring | 0.20 |
| Water | 20.00 |

Example 4-E-6

Throat Soothing Herb Candy

A throat soothing herb candy was produced under the same conditions as in Example 4-E-5, except for using, instead of the equol-containing fermented soybean hypocotyl material, 0.5 g of the solid extract prepared in Example 1-1 by evaporating Liquid Extract 1-2 obtained using 75Et to dryness.

Example 4-E-7

Lemon Gummy Candy

A lemon gummy candy was produced in accordance with a general production method of a gummy candy, using the ingredients of the following composition.

| | |
|---|---|
| Equol-containing fermented soybean hypocotyl material (Reference Example 1-2) | 4.00 (g) |
| Acid gelatin (250 blooms) | 7.00 |
| Reducing starch syrup | 100.00 |
| 4 times concentrated lemon juice | 1.25 |
| Citric acid (crystalline) | 1.00 |
| Sucralose | 0.02 |
| Food coloring | 0.02 |
| Flavor | 0.02 |
| Water | 12.00 |

Example 4-E-8

Lemon Gummy Candy

A lemon gummy candy was produced under the same conditions as in Example 4-E-7, except for using, instead of the equol-containing fermented soybean hypocotyl material, 0.5 g of the solid extract prepared in Example 1-1 by evaporating Liquid Extract 1-2 obtained using 75Et to dryness.

Example 4-E-9

Caramel Candy

A caramel candy was produced in accordance with a general production method of a caramel candy, using the ingredients of the following composition.

| | |
|---|---|
| Equol-containing fermented soybean hypocotyl material (Reference Example 1-1) | 4.00 (g) |
| Sweetened condensed milk | 45.00 |
| Starch syrup | 45.00 |
| Vegetable fat and oil | 3.50 |
| Lecithin | 0.20 |
| Fondant | 5.00 |
| Flavor (caramel flavor) | 0.10 |

Example 4-E-10

Caramel Candy

A caramel candy was produced under the same conditions as in Example 4-E-9, except for using, instead of the equol-containing fermented soybean hypocotyl material, 0.5 g of the solid extract prepared in Example 1-1 by evaporating Liquid Extract 1-2 obtained using 75Et to dryness.

Example 4-E-11

Pretzel

The following ingredients were mixed to prepare dough, which was baked in an oven; thereby, a pretzel was produced.

| | |
|---|---|
| Equol-containing fermented soybean hypocotyl material (Reference Example 1-1) | 4.00 (g) |
| Strong flour | 100.00 |
| Baking powder | 1.35 |
| Unsalted butter | 25.00 |
| Table salt | 2.00 |
| Sugar | 17.50 |
| Soybean dietary fiber | 0.80 |
| Sucrose fatty acid ester | 0.30 |
| Flavor | 0.20 |
| Water | 40.00 |

Example 4-E-12

Pretzel

A pretzel was produced under the same conditions as in Example 4-E-11, except for using, instead of the equol-containing fermented soybean hypocotyl material, 0.5 g of the solid extract prepared in Example 1-1 by evaporating Liquid Extract 1-2 obtained using 75Et to dryness.

Example 4-E-13

Mint Tablet

A mint tablet was produced in accordance with a general production method of a tablet, using the ingredients of the following composition.

| | |
|---|---|
| Equol-containing fermented soybean hypocotyl material (Reference Example 1-3) | 4.00 (g) |
| Sorbitol | 90.00 |
| Sucralose | 0.15 |
| Peppermint flavor | 5.00 |
| Sucrose fatty acid ester | 1.00 |

Example 4-E-14

Mint Tablet

A mint tablet was produced under the same conditions as in Example 4-E-13, except for using, instead of the equol-containing fermented soybean hypocotyl material, 0.5 g of the solid extract prepared in Example 1-1 by evaporating Liquid Extract 1-2 obtained using 75Et to dryness.

Example 4-E-15

Yogurt Tablet

A yogurt tablet was produced in accordance with a general production method of a tablet, using the ingredients of the following composition.

| | |
|---|---|
| Equol-containing fermented soybean hypocotyl material (Reference Example 1-2) | 4.00 (g) |
| Trehalose (granulation) | 88.60 |
| Sucralose | 0.08 |
| Powdered fermented milk | 5.00 |
| Anhydrous citric acid | 1.00 |
| Yogurt flavor | 0.20 |
| Sucrose fatty acid ester | 1.50 |

Example 4-E-16

Yogurt Tablet

A yogurt tablet was produced under the same conditions as in Example 4-E-15, except for using, instead of the equol-containing fermented soybean hypocotyl material, 0.5 g of the solid extract prepared in Example 1-1 by evaporating Liquid Extract 1-2 obtained using 75Et to dryness.

Example 4-E-17

Lemon Tablet

A lemon tablet was produced in accordance with a general production method of a tablet, using the ingredients of the following composition.

| | |
|---|---|
| Equol-containing fermented soybean hypocotyl material (Reference Example 1-1) | 4.00 (g) |
| Sugar (granulation) | 89.50 |
| Powdered lemon juice | 2.00 |
| L-ascorbic acid | 3.00 |
| Anhydrous citric acid | 1.00 |
| Sucrose fatty acid ester | 1.00 |

Example 4-E-18

Lemon Tablet

A lemon tablet was produced under the same conditions as in Example 4-E-17, except for using, instead of the equol-containing fermented soybean hypocotyl material, 0.5 g of the solid extract prepared in Example 1-1 by evaporating Liquid Extract 1-2 obtained using 75Et to dryness.

Example 4-E-19

Mint Chewing Gum

Mint chewing gum was produced in accordance with a general production method of a chewing gum, using the ingredients of the following composition.

| | |
|---|---|
| Equol-containing fermented soybean hypocotyl material (Reference Example 1-1) | 4.00 (g) |
| Gum base | 25.00 |
| Lactitol | 63.20 |
| Sugar alcohol | 5.00 |
| Sucralose | 0.13 |
| Glycerine | 0.50 |
| Peppermint oil | 1.50 |
| Mint Flavor | 0.50 |
| Food coloring | 0.20 |

Example 4-E-20

Mint Chewing Gum

Mint chewing gum was produced under the same conditions as in Example 4-E-19, except for using, instead of the equol-containing fermented soybean hypocotyl material, 0.5 g of the solid extract prepared in Example 1-1 by evaporating Liquid Extract 1-2 obtained using 75Et to dryness.

Example 4-E-21

Apple Bubble Gum

Apple bubble gum was produced in accordance with a general production method of a chewing gum, using the ingredients of the following composition.

| | |
|---|---|
| Equol-containing fermented soybean hypocotyl material (Reference Example 1-1) | 4.00 (g) |
| Gum base | 30.00 |
| Palatinit | 70.00 |
| Sucralose | 0.084 |
| Glycerine | 0.50 |
| Citric acid (crystalline) | 1.00 |
| Apple flavor | 0.80 |

Example 4-E-22

Apple Bubble Gum

Apple bubble gum was produced under the same conditions as in Example 4-E-21, except for using, instead of the equol-containing fermented soybean hypocotyl material, 0.5 g of the solid extract prepared in Example 1-1 by evaporating Liquid Extract 1-2 obtained using 75Et to dryness.

Example 4-E-23

Strawberry Chewing Gum

Strawberry chewing gum was produced in accordance with a general production method of a chewing gum, using the ingredients of the following composition.

| | |
|---|---|
| Equol-containing fermented soybean hypocotyl material (Reference Example 1-3) | 4.00 (g) |
| Gum base | 23.00 |
| Powdered sugar | 62.00 |
| Starch syrup | 5.00 |
| Sucralose | 0.001 |
| Citric acid (crystalline) | 1.20 |
| Red cabbage color | 0.20 |
| Strawberry flavor | 0.20 |

Example 4-E-24

Strawberry Chewing Gum

Strawberry chewing gum was produced under the same conditions as in Example 4-E-23, except for using, instead of the equol-containing fermented soybean hypocotyl material, 0.5 g of the solid extract prepared in Example 1-1 by evaporating Liquid Extract 1-2 obtained using 75Et to dryness.

Example 4-E-25

Chocolate

Chocolate was produced in accordance with a general production method of chocolate, using the ingredients of the following composition.

| | |
|---|---|
| Equol-containing fermented soybean hypocotyl material (Reference Example 1-3) | 4.00 (g) |
| *Cacao* mass | 40.00 |
| Cocoa butter | 25.00 |
| Reduced powder sugar | 50.00 |
| Sucralose | 0.03 |
| Lecithin | 0.40 |
| Vanillin | 0.05 |

Example 4-E-26

Chocolate

Chocolate was produced under the same conditions as in Example 4-E-25, except for using, instead of the equol-containing fermented soybean hypocotyl material, 0.5 g of the solid extract prepared in Example 1-1 by evaporating Liquid Extract 1-2 obtained using 75Et to dryness.

Example 4-E-27

Strawberry-Flavored Chocolate

Strawberry-flavored chocolate was produced in accordance with a general production method of chocolate, using the ingredients of the following composition.

| | |
|---|---|
| Equol-containing fermented soybean hypocotyl material (Reference Example 1-3) | 4.00 (g) |
| Cocoa butter | 25.00 |
| Hard butter | 7.00 |
| Whole milk powder | 27.00 |
| Sugar | 41.00 |
| Strawberry flavor | 0.20 |
| Beet red | 0.50 |
| Sucralose | 0.001 |
| Lecithin | 0.30 |
| Vanillin | 0.02 |

Example 4-E-28

Strawberry-Flavored Chocolate

Strawberry-flavored chocolate was produced under the same conditions as in Example 4-E-27, except for using, instead of the equol-containing fermented soybean hypocotyl material, 0.5 g of the solid extract prepared in Example 1-1 by evaporating Liquid Extract 1-2 obtained using 75Et to dryness.

Example 4-E-29

Cookie

The following ingredients were mixed to prepare dough, which was baked in an oven to produce a cookie.

| | |
|---|---|
| Equol-containing fermented soybean hypocotyl material (Reference Example 1-3) | 0.40 (part by weight) |
| Soft flour | 48.50 |
| Baking powder | 0.30 |
| Unsalted margarine | 24.00 |
| Table salt | 0.20 |
| Sugar | 12.00 |
| Egg yolk | 4.70 |
| Trehalose | 22.00 |
| Flavor | 0.20 |
| Water | 40.00 |

Example 4-E-30

Cookie

A cookie was produced under the same conditions as in Example 4-E-29, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E-31

Skin of Manju (a Bun Filled with Steamed Azuki Bean Jam)

The skin of a manju (a bun filled with steamed azuki bean jam) was produced in accordance with a general production method of a skin of manju, using the ingredients of the following composition.

| | |
|---|---|
| Equol-containing fermented soybean hypocotyl material (Reference Example 1-2) | 4.00 (part by weight) |
| Soft flour | 500.00 |
| Baking powder | 2.50 |
| Xanthan gum | 1.00 |
| Table salt | 6.00 |
| Sugar | 30.00 |
| Trehalose | 30.00 |
| Dry yeast | 7.50 |
| Lard | 15.00 |
| Water | 200.00 |

Example 4-E-32

Skin of Manju (a Bun Filled with Steamed Azuki Bean Jam)

The skin of a manju (a bun filled with steamed azuki bean jam) was produced under the same conditions as in Example 4-E-31, except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-E-33

Apple Pie Filling

An apple pie filling was produced using the following ingredients.

| | |
|---|---|
| Equol-containing fermented soybean hypocotyl material (Reference Example 1-1) | 0.40 (part by weight) |
| Apple | 200.00 |
| Maltose | 150.00 |
| Sucralose | 0.10 |
| Lemon juice | 10.00 |
| Walnut | 60.00 |
| Raisin | 60.00 |
| Apple flavor | 0.20 |

Example 4-E-34

Apple Pie Filling

An apple pie filling was produced under the same conditions as in Example 4-E-33, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E-35

Pound Cake

The following ingredients were mixed to prepare dough, which was baked in an oven to produce a pound cake.

| | |
|---|---|
| Equol-containing fermented soybean hypocotyl material (Reference Example 1-1) | 0.40 (part by weight) |
| Butter | 100.00 |
| Reducing maltose syrup | 100.00 |
| Sucralose | 0.03 |
| Stevia | 0.03 |
| Whole egg | 100.00 |
| Flavor | 0.22 |
| Soft flour | 120.00 |
| Baking powder | 1.50 |

Example 4-E-36

Pound Cake

A pound cake was produced under the same conditions as in Example 4-E-35, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E-37

Bracken-Starch Dumpling

A bracken-starch dumpling was produced using the following ingredients.

| | |
|---|---|
| Equol-containing fermented soybean hypocotyl material (Reference Example 1-1) | 0.40 (part by weight) |
| Rice starch | 20.00 |
| Sweet potato starch | 40.00 |
| Sugar | 6.00 |
| Water | Balance |
| Total | 100.00 parts by weight |

Example 4-E-38

Bracken-Starch Dumpling

A bracken-starch dumpling was produced under the same conditions as in Example 4-E-37, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E-39

Bean Confectionary

A bean confectionary was produced using the following ingredients.

| | |
|---|---|
| Equol-containing fermented soybean hypocotyl material (Reference Example 1-3) | 6.00 (part by weight) |
| Kanbaiko (ground toasted rice cake) | 7.00 |
| Sugar | 53.00 |
| Kinako (roasted soybean powder) | 4.00 |
| Baking powder | q.s. |
| Flavor | q.s. |
| Sweetener | q.s. |
| Total | 100.00 parts by weight |

Example 4-E-40

Bean Confectionary

A bean confectionary was produced under the same conditions as in Example 4-E-39, except for using, instead of the equol-containing fermented soybean hypocotyl material, 0.75 parts by weight of the solid extract prepared in Example 1-1 by evaporating Liquid Extract 1-2 obtained using 75Et to dryness.

Example 4-E-41

Bean Confectionary

A bean confectionary was produced using the following ingredients.

| | |
|---|---|
| Equol-containing fermented soybean hypocotyl material (Reference Example 1-2) | 12.00 (part by weight) |
| Rice flour | 13.00 |
| Sugar | 45.00 |
| Kinako (roasted soybean powder) | 15.00 |
| Powdered green tea | 15.00 |
| Baking powder | q.s. |
| Flavor | q.s. |
| Sweetener | q.s. |
| Total | 100.00 parts by weight |

Example 4-E-42

Bean Confectionary

A bean confectionary was produced under the same conditions as in Example 4-E-41, except for using, instead of the equol-containing fermented soybean hypocotyl material, 1.5 parts by weight of the solid extract prepared in Example 1-1 by evaporating Liquid Extract 1-2 obtained using 75Et to dryness.

Example 4-E-43

Bean Confectionary

A bean confectionary was produced using the following ingredients.

| | |
|---|---|
| Equol-containing fermented soybean hypocotyl material (Reference Example 1-1) | 18.00 (part by weight) |
| Kanbaiko (ground toasted rice cake) | 15.00 |
| Sugar | 52.00 |
| Kinako (roasted soybean powder) | 15.00 |
| Powdered green tea | 12.00 |
| Baking powder | q.s. |

-continued

| | |
|---|---|
| Flavor | q.s. |
| Sweetener | q.s. |
| Total | 100.00 parts by weight |

Example 4-E-44

Bean Confectionary

A bean confectionary was produced under the same conditions as in Example 4-E-43, except for using, instead of the equol-containing fermented soybean hypocotyl material, 2.25 parts by weight of the solid extract prepared in Example 1-1 by evaporating Liquid Extract 1-2 obtained using 75Et to dryness.

Example 4-E-45

Bean Confectionary

A bean confectionary was produced using the following ingredients.

| | |
|---|---|
| Equol-containing fermented soybean hypocotyl material (Reference Example 1-3) | 6.00 (part by weight) |
| Starch | 20.00 |
| Sugar | 32.00 |
| Kinako (roasted soybean powder) | 10.00 |
| Black sesame seeds | 20.00 |
| Baking powder | q.s. |
| Flavor | q.s. |
| Sweetener | q.s. |
| Total | 100.00 parts by weight |

Example 4-E-46

Bean Confectionary

A bean confectionary was produced under the same conditions as in Example 4-E-45, except for using, instead of the equol-containing fermented soybean hypocotyl material, 0.75 parts by weight of the solid extract prepared in Example 1-1 by evaporating Liquid Extract 1-2 obtained using 75Et to dryness.

Example 4-E-47

Nama-Fu Confectionary (Fresh Gluten Cake)

A nama-fu confectionary (fresh gluten cake) was produced using the following ingredients.

| | |
|---|---|
| Equol-containing fermented soybean hypocotyl material (Reference Example 1-3) | 10.00 (part by weight) |
| Gluten | 20.00 |
| Rice flour | 15.00 |
| Kinako (roasted soybean powder) | q.s. |
| Emulsifier | q.s. |
| Honey | q.s. |
| Sorbitol | 20.00 |
| Chocolate | 30.00 |

Example 4-E-48

Nama-Fu Confectionary (Fresh Gluten Cake)

A nama-fu confectionary (fresh gluten cake) was produced under the same conditions as in Example 4-E-47, except for using, instead of the equol-containing fermented soybean hypocotyl material, 1.25 parts by weight of the solid extract prepared in Example 1-1 by evaporating Liquid Extract 1-2 obtained using 75Et to dryness.

Example 4-E-49

Wafer (Rich Type)

A wafer (rich type) was produced in accordance with a general production method of a wafer, using the following ingredients.

| | |
|---|---|
| Equol-containing fermented soybean hypocotyl material (Reference Example 1-3) | 0.40 (part by weight) |
| Wheat flour | 100.00 |
| Sugar | 2.00 |
| Fats and oils | 3.00 |
| Whole egg | 3.00 |
| Skimmed milk | 2.00 |
| Sodium bicarbonate | 0.30 |
| Cow's milk | 50.00 |
| Water | 100.00 |

Example 4-E-50

Wafer (Rich Type)

A wafer (rich type) was produced under the same conditions as in Example 4-E-49, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E-51

Wafer (Plain)

A wafer (plain) was produced in accordance with a general production method of a wafer, using the following ingredients.

| | |
|---|---|
| Equol-containing fermented soybean hypocotyl material (Reference Example 1-3) | 0.40 (part by weight) |
| Wheat flour | 100.00 |
| Fats and oils | 2.50 |
| Whole egg | 0.30 |
| Ammonium carbonate | 0.40 |
| Sodium bicarbonate | 0.30 |
| Lecithin | 0.05 |
| Water | 150.00 |

Example 4-E-52

Wafer (Plain)

A wafer (plain) was produced under the same conditions as in Example 4-E-51, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E-53

Cheese Cracker

A cheese cracker was produced in accordance with a general production method, using the following ingredients.

| | |
|---|---|
| Equol-containing fermented soybean hypocotyl material (Reference Example 1-3) | 0.40 (part by weight) |
| Wheat flour | 100.00 |
| Fats and oils | 9.00 |
| Malt extract | 1.30 |
| Sodium bicarbonate | 0.60 |
| Spice | 0.10 |
| Cheese powder | 13.00 |
| Sugar | 80.00 |
| Table salt | 0.90 |
| Ammonium carbonate | 0.60 |
| Lecithin | 0.05 |
| Water | 33.00 |

Example 4-E-54

Cheese Cracker

A cheese cracker was produced under the same conditions as in Example 4-E-53, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-E-55

Yokan (Azuki Bean Jelly)

Yokan (azuki bean jelly) was produced in accordance with a general production method, using the following ingredients.

| | |
|---|---|
| Equol-containing fermented soybean hypocotyl material (Reference Example 1-3) | 4.00 (part by weight) |
| Agar | 7.50 |
| Granulated sugar | 320.00 |
| Red bean paste | 620.00 |
| Starch syrup | 50.00 |
| Water | 300.00 |

Example 4-E-56

Yokan (Azuki Bean Jelly)

Yokan (azuki bean jelly) was produced under the same conditions as in Example 4-E-55, except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-E-57

Soft Cookie

A soft cookie was produced in accordance with a general production method, using the following ingredients.

| | |
|---|---|
| Equol-containing fermented soybean hypocotyl material (Reference Example 1-3) | 4.00 (part by weight) |
| Wheat flour | 200.00 |
| Butter | 150.00 |
| Sugar | 80.00 |
| Whole egg | 150.00 |

Example 4-E-58

Soft Cookie

A soft cookie was produced under the same conditions as in Example 4-E-57, except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-E-59

Rice Cracker

A rice cracker was produced in accordance with a general production method, using the following ingredients.

| | |
|---|---|
| Equol-containing fermented soybean hypocotyl material (Reference Example 1-3) | 0.40 (part by weight) |
| Regular rice | 100.00 |
| Hot water | q.s. |

Example 4-E-60

Rice Cracker

A rice cracker was produced under the same conditions as in Example 4-E-59, except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-E-61

Suhama (Japanese Traditional Confectionary)

Suhama (Japanese traditional confectionary) was produced in accordance with a general production method, using the following ingredients.

| | |
|---|---|
| Equol-containing fermented soybean hypocotyl material (Reference Example 1-3) | 4.00 (part by weight) |
| White superior soft sugar | 600.00 |
| Kinako (roasted soybean powder) | 400.00 |
| Starch syrup | 130.00 |
| Water | 180.00 |

Example 4-E-62

Suhama (Japanese Traditional Confectionary)

Suhama (Japanese traditional confectionary) was produced under the same conditions as in Example 4-E-61, except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-E-63

Dry Confectionary

A dry confectionary was produced in accordance with a general production method, using the following ingredients.

| | |
|---|---|
| Equol-containing fermented soybean hypocotyl material (Reference Example 1-3) | 4.00 (part by weight) |
| Wasanbon sugar | 500.00 |
| Shitori (for making the ingredients wet during the process) | 25.00 |
| Kanbaiko (ground toasted rice cake) | 75.00 |

Example 4-E-64

Dry Confectionary

A dry confectionary was produced under the same conditions as in Example 4-E-63, except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-E-65

Fruit Gummy Candy

A fruit gummy candy was produced in accordance with a general production method, using the following ingredients.

| | |
|---|---|
| Equol-containing fermented soybean hypocotyl material (Reference Example 1-3) | 4.00 (part by weight) |
| Sugar | 30.00 |
| Starch syrup | 50.00 |
| Gelatin | 7.00 |
| Fruit juice | 5.00 |
| Citric acid | 1.50 |
| Flavor | 0.20 |

Example 4-E-66

Fruit Gummy Candy

A fruit gummy candy was produced under the same conditions as in Example 4-E-65, except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-E-67

Soy Flour-Containing Baked Confectionary

An amount of 1.25 wt. % of equol-containing fermented soybean hypocotyl material (Reference Example 1-3) and 25 wt. % of soy flour, as well as raisins, butter, sugar, egg, orange peel, pineapple, hard-to-digest dextrin, cacao mass, almond slices, cocoa powder, table salt, baking powder, and flavors were mixed in a suitable amount. The resultant mixture (100 wt. %) was then formed into a rectangle (about 1.5 cm×1.5 cm×10 cm) using a mold to be baked in an oven at 180° C., thereby producing a soy flour-containing baked confectionary.

Example 4-E-68

Soy Flour-Containing Baked Confectionary

A soybean flour-containing baked confectionary was produced under the same conditions as in Example 4-E-67, except for using, instead of the equol-containing fermented soybean hypocotyl material, 0.25 parts by weight of the solid extract prepared in Example 1-1 by evaporating Liquid Extract 1-2 obtained using 75Et to dryness.

Example 4-F

Seasoning

Hereinafter, specific production examples of the seasoning according to the present invention are given.

Example 4-F-1

Barbecue Sauce

A barbecue sauce having the following composition was produced.

| | |
|---|---|
| Equol-containing fermented soybean hypocotyl material (Reference Example 1-3) | 4.00 (Kg) |
| Reducing starch syrup | 20.00 |
| Trehalose | 0.50 |
| Mirin | 4.00 |
| Soy sauce (dark) | 24.00 |
| Apple puree | 19.00 |
| Garlic paste | 4.50 |
| Ginger paste | 4.50 |
| Sesame oil | 0.10 |
| Xanthan gum | 0.50 |
| Red pepper powder | 0.10 |
| Black pepper powder | 0.05 |
| Citric acid (crystalline) | 0.20 |
| Toasted sesame seeds | 0.40 |
| Water | Balance |
| Total | 100.00 kg |

Example 4-F-2

Barbecue Sauce

A barbecue sauce was produced under the same conditions as in Example 4-F-1, except for using, instead of the equol-containing fermented soybean hypocotyl material, 0.5 kg of the solid extract prepared in Example 1-1 by evaporating Liquid Extract 1-2 obtained using 75Et to dryness.

Example 4-F-3

Tomato Ketchup

A tomato ketchup having the following composition was produced.

| | |
|---|---|
| Equol-containing fermented soybean hypocotyl material (Reference Example 1-2) | 4.00 (Kg) |
| Tomato paste | 40.00 |
| Wine vinegar | 18.00 |
| Fructose/glucose syrup | 5.00 |
| Soy sauce (dark) | 24.00 |
| Table salt | 2.50 |
| Garlic powder | 0.07 |
| Onion powder | 0.10 |
| Cinnamon powder | 0.02 |
| Clove powder | 0.01 |
| Water | Balance |
| Total | 100.00 kg |

Example 4-F-4

Tomato Ketchup

A tomato ketchup was produced under the same conditions as in Example 4-F-3, except for using, instead of the equol-containing fermented soybean hypocotyl material, 0.5 kg of the solid extract prepared in Example 1-1 by evaporating Liquid Extract 1-2 obtained using 75Et to dryness.

Example 4-F-5

Tsuyu (Dipping Sauce)

Tsuyu (dipping sauce for tempura, i.e. Japanese deep-fried food) having the following composition was produced.

| | |
|---|---|
| Equol-containing fermented soybean hypocotyl material (Reference Example 1-2) | 4.00 (Kg) |
| Sugar | 7.00 |
| Soy sauce (dark) | 26.00 |
| Soy sauce (light) | 10.00 |
| Fish sauce | 5.00 |
| Mirin | 10.00 |
| Sodium L-glutamate monohydrate | 3.00 |
| Table salt | 0.60 |
| Water | Balance |
| Total | 100.00 Kg |

Example 4-F-6

Tsuyu (Soup)

Tsuyu (soup) was produced under the same conditions as in Example 4-F-5, except for using, instead of the equol-containing fermented soybean hypocotyl material, 0.5 kg of the solid extract prepared in Example 1-1 by evaporating Liquid Extract 1-2 obtained using 75Et to dryness.

Example 4-F-7

Dressing

The aqueous phase and the oil phase of the following composition were mixed in a weight ratio of 7:3 to produce a dressing (separate type).

Composition of Aqueous Phase

| | |
|---|---|
| Equol-containing fermented soybean hypocotyl material (Reference Example 1-3) | 4.00 (Kg) |
| Sugar | 6.00 |
| Soy sauce (dark) | 20.00 |
| Brewed vinegar (acidity: 10%) | 8.50 |
| Fish sauce | 3.00 |
| Lemon juice | 2.00 |
| Table salt | 2.00 |
| Sodium L-glutamate monohydrate | 0.20 |
| Red pepper powder | 0.05 |
| Toasted sesame seeds | 0.30 |
| Xanthan gum | 0.10 |
| Water | Balance |
| Total | 100.00 kg |

Composition of Oil Phase

| | |
|---|---|
| Sesame oil | 20.00 (Kg) |
| Corn salad oil | 79.00 |
| Seasoning flavor | 1.00 |
| Total | 100.00 kg |

Example 4-F-8

Dressing

A dressing (separate type) was produced under the same conditions as in Example 4-F-7, except for using, instead of the equol-containing fermented soybean hypocotyl material, 0.5 kg of the solid extract prepared in Example 1-1 by evaporating Liquid Extract 1-2 obtained using 75Et to dryness.

Example 4-F-9

Sesame Dipping Sauce for Shabu-Shabu (Thinly Sliced Meet and Vegetables Boiled Quickly in Hot Water)

Sesame dipping sauce for shabu-shabu having the following composition was produced.

| | |
|---|---|
| Equol-containing fermented soybean hypocotyl material (Reference Example 1-2) | 0.40 (Kg) |
| Soy sauce (light) | 12.00 |
| Brewed vinegar | 11.00 |
| Garlic powder | 0.10 |
| Ginger powder | 0.10 |
| White pepper | 0.10 |
| Chicken extract | 3.00 |
| Yeast extract | 3.00 |
| Sesame oil | 1.00 |
| Fructose/glucose syrup | 8.00 |
| Mirin | 15.00 |
| White miso | 10.00 |
| Thickener | 3.50 |
| Sugar | 8.00 |
| Table salt | 10.00 |
| Flavor | 0.15 |
| Water | Balance |
| Total | 100.00 kg |

Example 4-F-10

Sesame Dipping Sauce for Shabu-Shabu (Thinly Sliced Meet and Vegetables Boiled Quickly in Hot Water)

Sesame dipping sauce for shabu-shabu was produced under the same conditions as in Example 4-F-9, except for using, instead of the equol-containing fermented soybean hypocotyl material, 0.05 kg of the solid extract prepared in Example 1-1 by evaporating Liquid Extract 1-2 obtained using 75Et to dryness.

Example 4-F-11

Barbecue Sauce (Miso Flavor)

Barbecue sauce (miso flavor) having the following composition was produced.

| | |
|---|---|
| Equol-containing fermented soybean hypocotyl material (Reference Example 1-3) | 4.00 (Kg) |
| Soy sauce (dark) | 25.00 |
| Miso | 14.00 |
| D-sorbitol | 12.00 |
| Table salt | 3.20 |
| Garlic powder | 3.30 |
| Garlic paste | 2.00 |
| Beef extract | 1.00 |
| Toasted sesame seeds | 0.50 |
| Sodium L-glutamate monohydrate | 0.50 |
| Ginger paste | 0.40 |
| Amino acid seasoning | 0.01 |
| Thickener | 3.50 |
| Sugar | 10.00 |
| Water | Balance |
| Total | 100.00 kg |

Example 4-F-12

Barbecue Sauce (Miso Flavor)

Barbecue sauce (miso flavor) was produced under the same conditions as in Example 4-F-11, except for using, instead of the equol-containing fermented soybean hypocotyl material, 0.05 kg of the solid extract prepared in Example 1-1 by evaporating Liquid Extract 1-2 obtained using 75Et to dryness.

Example 4-F-13

Snack Seasoning

A snack seasoning having the following composition was produced.

| | |
|---|---|
| Equol-containing fermented soybean hypocotyl material (Reference Example 1-3) | 0.40 (part by weight) |
| Table salt | 14.00 |
| Tricalcium phosphate | 3.00 |
| Disodium succinate | 0.20 |
| Sodium L-glutamate monohydrate | 7.00 |
| Powdered soy sauce | 3.00 |
| Yeast extract | 1.50 |
| Onion powder | 1.50 |
| Paprika powder | 1.50 |
| Garlic powder | 6.00 |
| Red pepper powder | 0.50 |
| Chicken consommé | 21.00 |
| Beef consommé | 4.00 |
| Stevia | 0.60 |
| Glucose | 13.00 |
| Spice | 0.01 |
| Cornstarch | 23.00 |
| Sugar | 2.00 |

Example 4-F-14

Snack Seasoning

A snack seasoning was produced under the same conditions as in Example 4-F-13, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-F-15

Emulsified Soy Sauce

Emulsified soy sauce having the following composition was produced.

| | |
|---|---|
| Equol-containing fermented soybean hypocotyl material (Reference Example 1-2) | 0.40 (part by weight) |
| Salad oil | 34.00 |
| Soy sauce (dark) | 53.00 |
| Gum Arabic | 1.00 |
| Sugar | 12.00 |

Example 4-F-16

Emulsified Soy Sauce

Emulsified soy sauce was produced under the same conditions as in Example 4-F-15, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-F-17

Dressing

A dressing (emulsified type) having the following composition was produced.

| | |
|---|---|
| Equol-containing fermented soybean hypocotyl material (Reference Example 1-2) | 0.40 (part by weight) |
| Salad oil | 35.00 |
| Vinegar | 10.00 |
| Sugar | 11.00 |
| Table salt | 4.00 |
| Xanthan gum | 0.30 |
| Water | Balance |
| Total | 100.00 parts by weight |

Example 4-F-18

Dressing

A dressing (emulsified type) was produced under the same conditions as in Example 4-F-17, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-F-19

Sauce for Kabayaki (Broiled Seafood)

Sauce for Kabayaki (broiled seafood) having the following composition was produced.

| | |
|---|---|
| Equol-containing fermented soybean hypocotyl material (Reference Example 1-3) | 0.40 (part by weight) |
| D-sorbitol | 10.00 |
| Thickener | 0.30 |
| Soy sauce (dark) | 38.00 |
| Mirin | 20.00 |
| Umami extract | 2.00 |
| Table salt | 1.80 |
| Sodium L-glutamate monohydrate | 1.45 |
| Sodium inosinate | 0.025 |
| Sodium guanylate | 0.025 |
| Trehalose | 15.00 |
| Sugar | 6.00 |
| Caramel coloring | 0.50 |
| Onion color | 0.10 |
| Flavor | 0.50 |
| Water | Balance |
| Total | 100.00 parts by weight |

Example 4-F-20

Sauce for Kabayaki (Broiled Seafood)

Sauce for Kabayaki (broiled seafood) was produced under the same conditions as in Example 4-F-19, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-F-21

Seasoning for Squid Delicacies

A Seasoning for squid delicacies having the following composition was produced.

| | |
|---|---|
| Equol-containing fermented soybean hypocotyl material (Reference Example 1-2) | 0.40 (part by weight) |
| Soy sauce (dark) | 20.00 |
| Soy sauce (light) | 10.00 |
| Fish sauce | 5.00 |
| Mirin | 10.00 |
| Brewed vinegar | 2.00 |
| Sugar | 38.00 |
| Table salt | 1.00 |
| Sodium L-glutamate monohydrate | 2.00 |
| Umami extract | 1.40 |
| Disodium succinate | 0.20 |
| Garlic powder | 0.05 |
| Water | Balance |
| Total | 100.00 parts by weight |

Example 4-F-22

Seasoning for Squid Delicacies

A Seasoning for squid delicacies was produced under the same conditions as in Example 4-F-21, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-G

Retort-Packed Food

Hereinafter, specific production examples of the retort-packed food according to the present invention are given.

Example 4-G-1

Retort-Packed Curry

Retort-packed curry was produced in accordance with a general production method, using the following composition.

| | |
|---|---|
| Equol-containing fermented soybean hypocotyl material (Reference Example 1-3) | 0.40 (Kg) |
| Curry powder | 1.80 |
| Onion | 7.00 |
| Unsalted butter | 4.50 |
| Garlic paste | 0.60 |
| Ginger paste | 0.50 |
| Wheat flour | 4.50 |
| Fruit chutney | 3.00 |
| Tomato paste | 0.50 |
| Table salt | 0.55 |
| Sodium L-glutamate monohydrate | 0.48 |
| Nucleic acid seasoning | 0.015 |
| Demi-glace flavor | 1.00 |
| Pork extract seasoning | 0.50 |
| Bouillon flavor | 1.00 |
| Potato | 7.00 |
| Carrot | 5.00 |
| Beef | 10.00 |
| Water | Balance |
| Total | 100.00 Kg |

Example 4-G-2

Retort-Packed Curry

Retort-packed curry was produced under the same conditions as in Example 4-G-1, except for using, instead of the equol-containing fermented soybean hypocotyl material, 0.05 kg of the solid extract prepared in Example 1-1 by evaporating Liquid Extract 1-2 obtained using 75Et to dryness.

Example 4-G-3

Retort-Packed Premix of Chinese-Style Donburi

Retort-packed Premix of Chinese-style Donburi was produced in accordance with a general production method, using the following composition.

| | |
|---|---|
| Equol-containing fermented soybean hypocotyl material (Reference Example 1-3) | 0.40 (Kg) |
| Soy sauce (light) | 72.00 |
| Sake | 46.00 |
| Table salt | 4.00 |
| Sodium L-glutamate monohydrate | 1.30 |
| Nucleic acid seasoning | 0.07 |
| Chicken extract powder | 1.00 |
| Sugar | 7.00 |

-continued

| Water | 209.00 |
|---|---|
| Pork | 200.00 |
| Squid | 120.00 |
| Shrimp | 80.00 |
| Shiitake (*Lentinus edodes*) | 70.00 |
| Boiled bamboo shoots | 160.00 |
| Carrot | 60.00 |
| Onion | 240.00 |

Example 4-G-4

Retort-Packed Premix of Chinese-Style Donburi

Retort-packed premix of Chinese-style donburi was produced under the same conditions as in Example 4-G-3, except for using, instead of the equol-containing fermented soybean hypocotyl material, 0.05 kg of the solid extract prepared in Example 1-1 by evaporating Liquid Extract 1-2 obtained using 75Et to dryness.

Example 8

Processed Meat Product

Hereinafter, specific production examples of the processed meat product according to the present invention are given.

Example 4-H-1

Sausage

A sausage was produced in accordance with a general production method of a sausage, using the ingredients of the following composition.
Meat Portion

| 5 mm-minced pork (foreshank) | 70.00 (Kg) |
|---|---|
| 5 mm-minced pork (lard) | 10.00 |
| Ice water | 20.00 |
| Total | 100.00 kg |

Auxiliary Ingredients

| Equol-containing fermented soybean hypocotyl material (Reference Example 1-3) | 0.40 (Kg) |
|---|---|
| Table salt | 1.70 |
| Sodium nitrite | 0.012 |
| Polyphosphate | 0.30 |
| Sodium L-ascorbate | 1.00 |
| Sodium casein | 0.50 |
| White pepper powder | 0.10 |
| Potassium sorbate | 0.20 |
| Amino acid seasoning | 0.30 |
| Spice mix | 0.50 |

Example 4-H-2

Sausage

A sausage was produced under the same conditions as in Example 4-H-1, except for using, instead of the equol-containing fermented soybean hypocotyl material, 0.05 kg of the solid extract prepared in Example 1-1 by evaporating Liquid Extract 1-2 obtained using 75Et to dryness.

Example 4-H-3

Smoked Sausage

The meat portion and the seasoning having the following components respectively were mixed at a ratio of 16:1. Using the resultant mixture, smoked sausages were produced in accordance with a general production method of a smoked sausage.
Meat Portion

| Minced pork (foreshank) | 85.00 (Kg) |
|---|---|
| Whole egg | 4.00 |
| Cow's milk | 3.00 |
| Ice water | 7.00 |

Seasoning

| Equol-containing fermented soybean hypocotyl material (Reference Example 1-3) | 0.40 (Kg) |
|---|---|
| Table salt | 24.00 |
| Amino acid seasoning | 3.20 |
| Spice | 8.65 |
| Minced Onion | 16.00 |
| Sugar | 48.00 |

Example 4-H-4

Smoked Sausage

A smoked sausage was produced under the same conditions as in Example 4-H-3, except for using, instead of the equol-containing fermented soybean hypocotyl material, 0.05 kg of the solid extract prepared in Example 1-1 by evaporating Liquid Extract 1-2 obtained using 75Et to dryness.

Example 4-H-5

Hamburger Steak

A hamburger steak was produced in accordance with a general production method, using the following composition.

| Equol-containing fermented soybean hypocotyl material (Reference Example 1-3) | 0.40 (part by weight) |
|---|---|
| Mixture of ground beef and pork | 45.00 |
| Pork | 9.00 |
| Onion | 12.00 |
| Whole egg | 5.00 |
| Granulated soy protein | 9.00 |
| Sodium casein | 5.00 |
| Carrageenan | 1.50 |
| Locust bean gum | 0.50 |
| Spice | 0.30 |
| Yeast extract | 0.20 |
| Table salt | 1.00 |
| Sugar | 1.20 |
| Water-soluble dietary fiber | 1.00 |
| Water | Balance |
| Total | 100.00 parts by weight |

Example 4-H-6

Hamburger Steak

A hamburger steak was produced under the same conditions as in Example 4-H-5, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-I

Fish Paste

Hereinafter, specific production examples of the fish paste according to the present invention are given.

Example 4-I-1

Fried Kamaboko (Fish Paste Cake)

A fried Kamaboko (fish paste cake) was produced in accordance with a general production method of a fish paste cake, using the ingredients of the following composition.

| | |
|---|---|
| Equol-containing fermented soybean hypocotyl material (Reference Example 1-3) | 0.40 (Kg) |
| Surimi | 50.00 |
| Table salt | 1.50 |
| Amino acid seasoning | 0.30 |
| Glycine | 0.50 |
| Sodium acetate anhydrous | 0.30 |
| Potato starch | 8.00 |
| Mirin | 1.00 |
| Ice water | Balance |
| Total | 100.00 Kg |

Example 4-I-2

Fried Kamaboko (Fish Paste Cake)

A fried kamaboko (fish paste cake) was produced under the same conditions as in Example 4-I-1, except for using, instead of the equol-containing fermented soybean hypocotyl material, 0.05 kg of the solid extract prepared in Example 1-1 by evaporating Liquid Extract 1-2 obtained using 75Et to dryness.

Example 4-J

Processed Egg Product

Hereinafter, specific production examples of the processed egg product according to the present invention are given.

Example 4-J-1

Thick Japanese Omelet

A thick Japanese omelet was produced in accordance with a general production method of a thick Japanese omelet, using the ingredients of the following composition.

| | |
|---|---|
| Equol-containing fermented soybean hypocotyl material (Reference Example 1-3) | 0.40 (part by weight) |
| Whole egg | 70.00 |
| Table salt | 0.40 |
| Starch | 2.00 |
| Soup stock | 2.00 |
| Sugar | 1.20 |
| Sodium acetate | 1.00 |
| Water | Balance |
| Total | 100.00 parts by weight |

Example 4-J-2

Thick Japanese Omelet

A thick Japanese omelet was produced under the same conditions as in Example 4-J-1, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-K

Canned Food

Hereinafter, specific production examples of the canned food according to the present invention are given.

Example 4-K-1

Canned Mandarin Orange

A canned mandarin orange was produced by filling mandarin orange pulp and a syrup having the following composition in a can

| | |
|---|---|
| Equol-containing fermented soybean hypocotyl material (Reference Example 1-3) | 0.40 (part by weight) |
| Sugar | 10.00 |
| Fructose/glucose syrup | 10.00 |
| Citric acid | 0.25 |
| Trisodium citrate | 0.10 |
| Water | Balance |
| Total | 100.00 parts by weight |

Example 4-K-2

Canned Mandarin Orange

Canned mandarin orange was produced under the same conditions as in Example 4-K-1, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-L

Bread Product

Hereinafter, specific production examples of the bread according to the present invention are given.

Example 4-L-1

Loaf of Bread

A loaf of bread was produced using dough having the following composition.

Sponge Dough

| | |
|---|---|
| Strong flour | 70.00 (Kg) |
| Yeast food | 0.10 |
| Live yeast | 2.00 |
| Water | 40.00 |

Main Dough

| | |
|---|---|
| Equol-containing fermented soybean hypocotyl material (Reference Example 1-3) | 0.40 (Kg) |
| Strong flour | 30.00 |
| Sugar | 3.00 |
| Table salt | 2.00 |
| Skimmed milk | 2.00 |
| Shortening | 5.00 |
| Water | 25.00 |

Example 4-L-2

Loaf of Bread

A loaf of bread was produced under the same conditions as in Example 4-L-1, except for using, instead of the equol-containing fermented soybean hypocotyl material, 0.05 kg of the solid extract prepared in Example 1-1 by evaporating Liquid Extract 1-2 obtained using 75Et to dryness.

Example 4-M

Frozen Desert

Hereinafter, specific production examples of the frozen dessert according to the present invention are given.

Example 4-M-1

Ice Cream

Ice cream having the following composition was produced.

| | |
|---|---|
| Equol-containing fermented soybean hypocotyl material (Reference Example 1-3) | 0.40 (part by weight) |
| Raw cream | 8.80 |
| Butter | 5.00 |
| Starch syrup | 16.00 |
| Skimmed milk | 6.50 |
| Trehalose | 7.00 |
| Sugar | 5.00 |
| Stabilizer | 0.20 |
| Flavor | 0.15 |
| Water | Balance |
| Total | 100.00 parts by weight |

Example 4-M-2

Ice Cream

Ice cream was produced under the same conditions as in Example 4-M-1, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-N

Processed Soybean Food

Hereinafter, specific production examples of the processed soybean food according to the present invention are given.

Example 4-N-1

Fermented Soybeans

An amount of 99.6 parts by weight of steamed soybeans and 0.4 parts by weight of equol-containing fermented soybean hypocotyl material (Reference Example 1-3) were mixed. The resultant mixture was then inoculated with *Bacillus natto* for fermentation; thereby fermented soybeans were produced.

Example 4-N-2

Fermented Soybeans

Fermented Soybeans were produced under the same conditions as in Example 4-N-1, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-N-3

Tofu

Tofu having the following composition was produced.

| | |
|---|---|
| Equol-containing fermented soybean hypocotyl material (Reference Example 1-3) | 0.40 (part by weight) |
| Soya Milk | 99.30 |
| Magnesium chloride | 0.20 |
| Potassium sorbate | 0.10 |
| Total | 100.00 parts by weight |

Example 4-N-4

Tofu

Tofu was produced under the same conditions as in Example 4-N-3, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-O

Cooked Rice Product

Hereinafter, specific production examples of the cooked rice product according to the present invention are given.

Example 4-O-1

Rice Gruel

Rice gruel was produced in accordance with a general production method of rice gruel, using the ingredients of the following composition.

| | |
|---|---|
| Equol-containing fermented soybean hypocotyl material (Reference Example 1-3) | 0.40 (part by weight) |
| Rice | 160.00 |
| Table salt | 1.00 |
| Water | 900.00 |

Example 4-O-2

Rice Gruel

Rice gruel was produced under the same conditions as in Example 4-O-1, except for using, instead of the equol-containing fermented soybean hypocotyl material, 0.05 parts by weight of the solid extract prepared in Example 1-1 by evaporating Liquid Extract 1-2 obtained using 75Et to dryness.

Example 4-O-3

Steamed Glutinous Rice with Chestnuts

Steamed glutinous rice with chestnuts was produced in accordance with a general production method, using the following ingredients.

| | |
|---|---|
| Equol-containing fermented soybean hypocotyl material (Reference Example 1-3) | 4.00 (part by weight) |
| Glutinous rice | 1000.00 |
| Peeled chestnut | 300.00 |
| Soup stock | 230.00 |
| Black sesame seeds | 30.00 |
| Salt solution | 6.00 |

Example 4-O-4

Steamed Glutinous Rice with Chestnuts

Steamed glutinous rice with chestnuts was produced under the same conditions as in Example 4-O-3 except for using, instead of the equol-containing fermented soybean hypocotyl material, 0.5 parts by weight of the solid extract prepared in Example 1-1 by evaporating Liquid Extract 1-2 obtained using 75Et to dryness.

Example 4-P

Soup

Hereinafter, specific production examples of the soup according to the present invention are given.

Example 4-P-1

Corn Cream Soup

Corn cream soup was produced in accordance with a general production method of a soup, using the ingredients of the following composition.

| | |
|---|---|
| Equol-containing fermented soybean hypocotyl material (Reference Example 1-3) | 0.40 (part by weight) |
| Cow's milk | 180.00 |
| Corn | 190.00 |
| Consomme | 20.00 |
| Salad oil | 15.00 |
| Table salt | q.s. |
| Pepper | q.s. |
| Water | 360.00 |

Example 4-P-2

Corn Cream Soup

Corn cream soup was produced under the same conditions as in Example 4-P-1, except for using, instead of the equol-containing fermented soybean hypocotyl material, 0.05 parts by weight of the solid extract prepared in Example 1-1 by evaporating Liquid Extract 1-2 obtained using 75Et to dryness.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
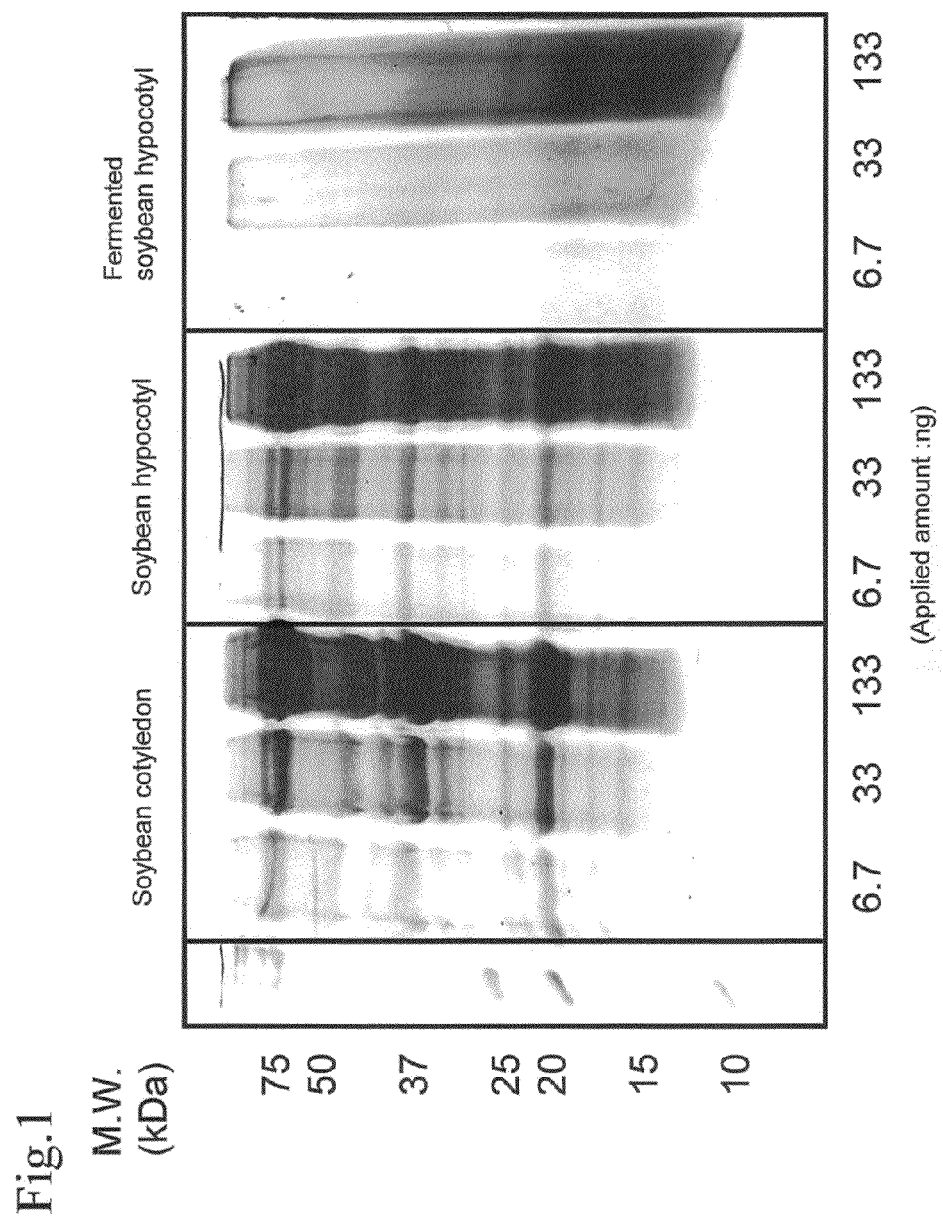
FIG. 1 is an electropherogram showing the total proteins contained in equol-containing fermented soybean hypocotyl obtained in Reference Example 1-1, soybean cotyledon, and the soybean hypocotyl.
Figure 2:
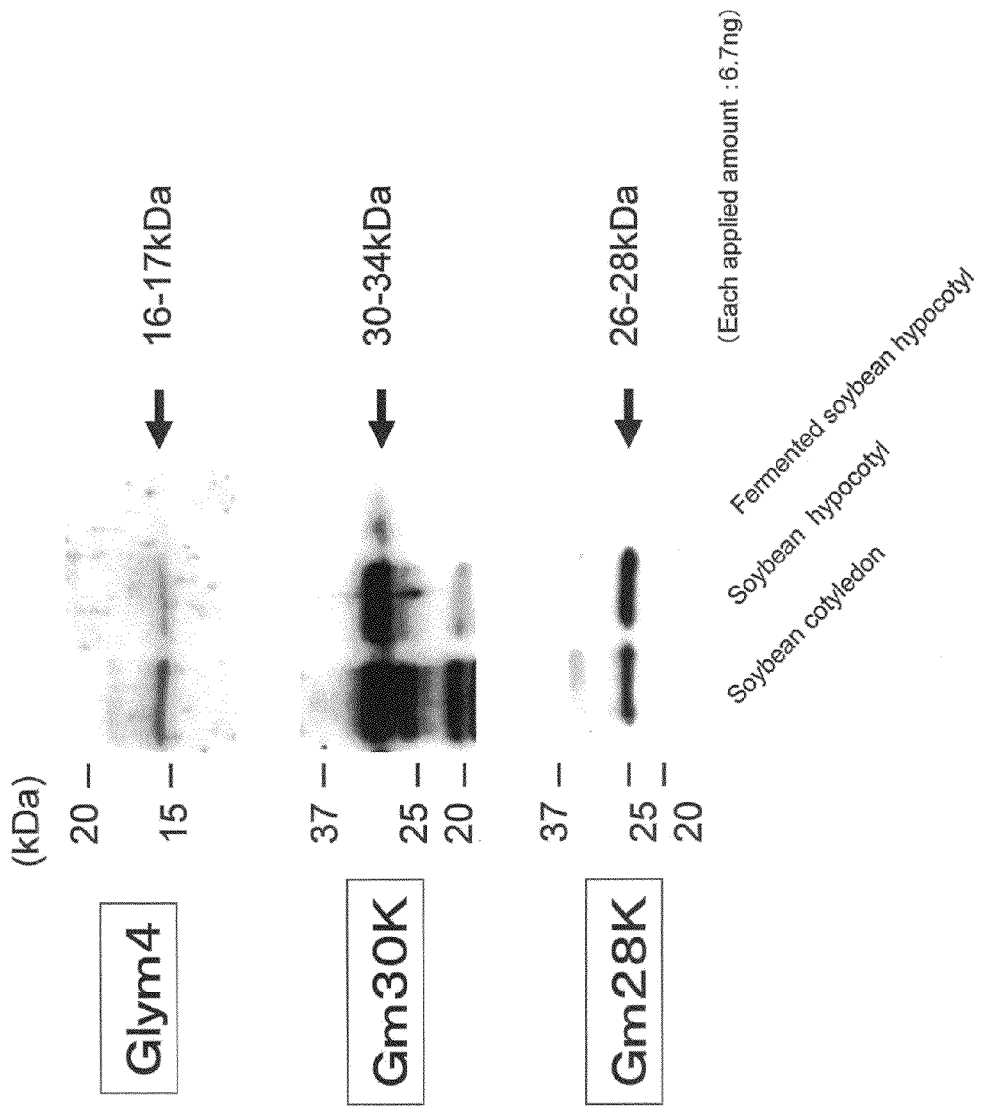
FIG. 2 is an electropherogram showing the results of the detection of major allergens (Gym4, Gm30K, and Gm28K) contained in the equol-containing fermented soybean hypocotyl obtained in Reference Example 1-1, soybean cotyledon, and the soybean hypocotyl.
Figure 3:
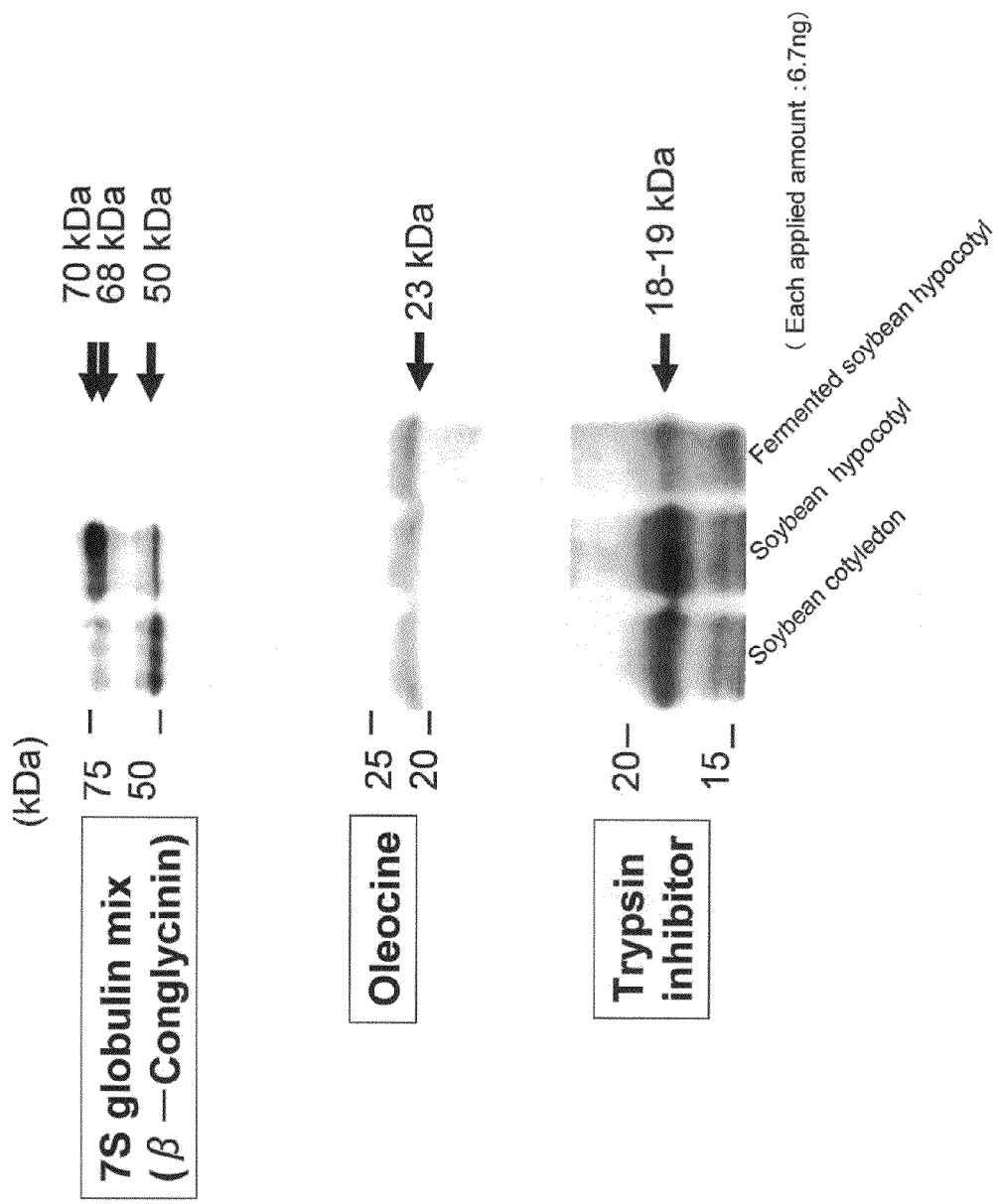
FIG. 3 is an electropherogram showing the results of the detection of major allergens (7S globulin mix, oleocine, and trypsin inhibitor) contained in the equol-containing fermented soybean hypocotyl obtained in Reference Example 1-1, soybean cotyledon, and the soybean hypocotyl.
Figure 4:
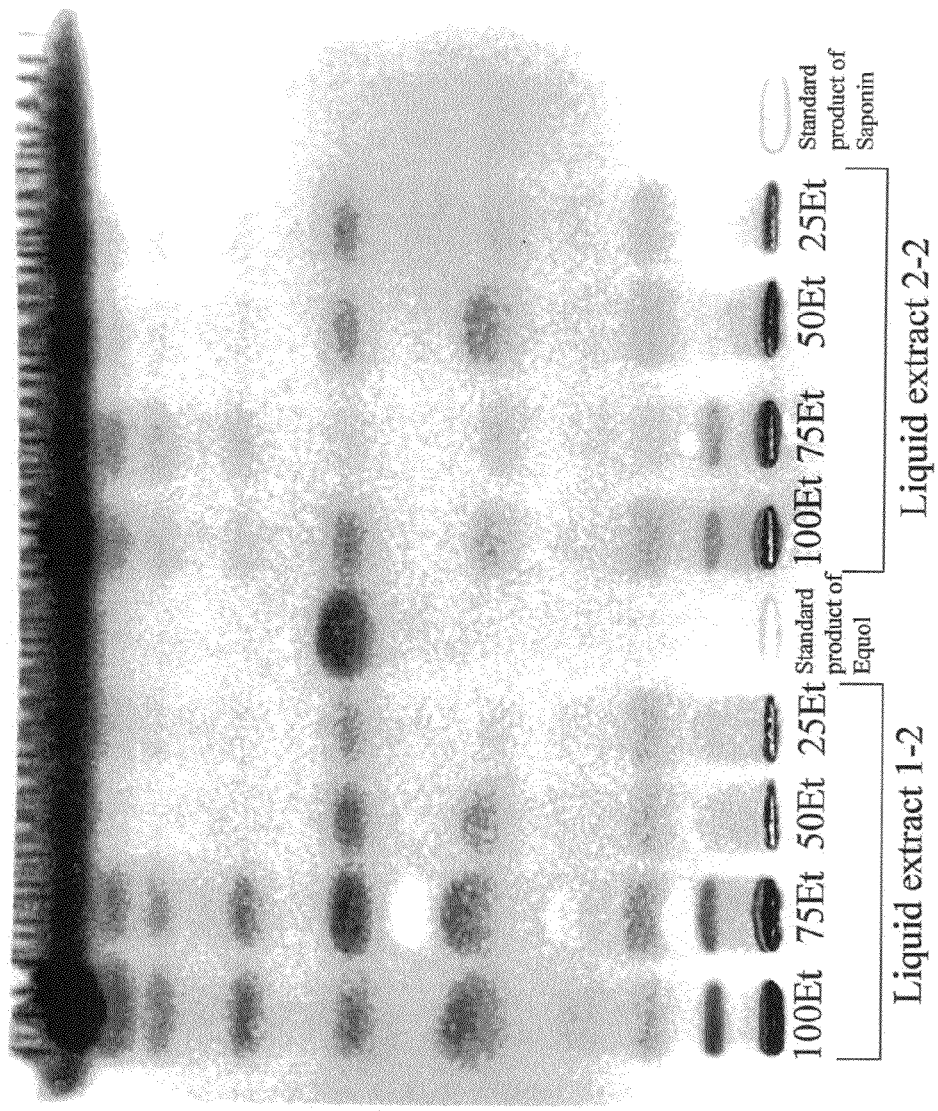
FIG. 4 shows TLC analysis results indicating the equol contents of Liquid Extracts 1-2 and 2-2 in Example 1-1.
Figure 5:
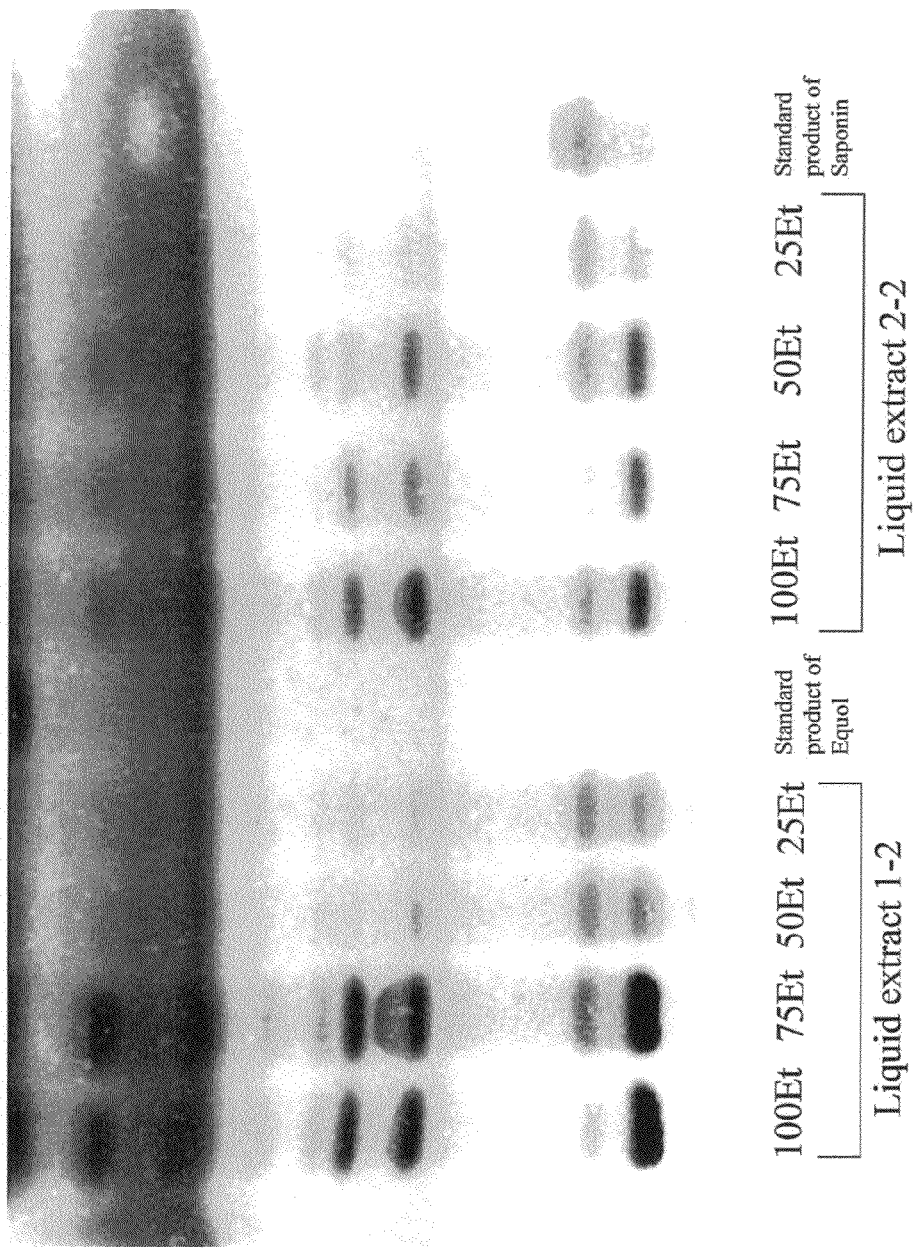
FIG. 5 shows TLC analysis results indicating the saponin contents of Liquid Extracts 1-2 and 2-2 in Example 1-1.
Figure 6:
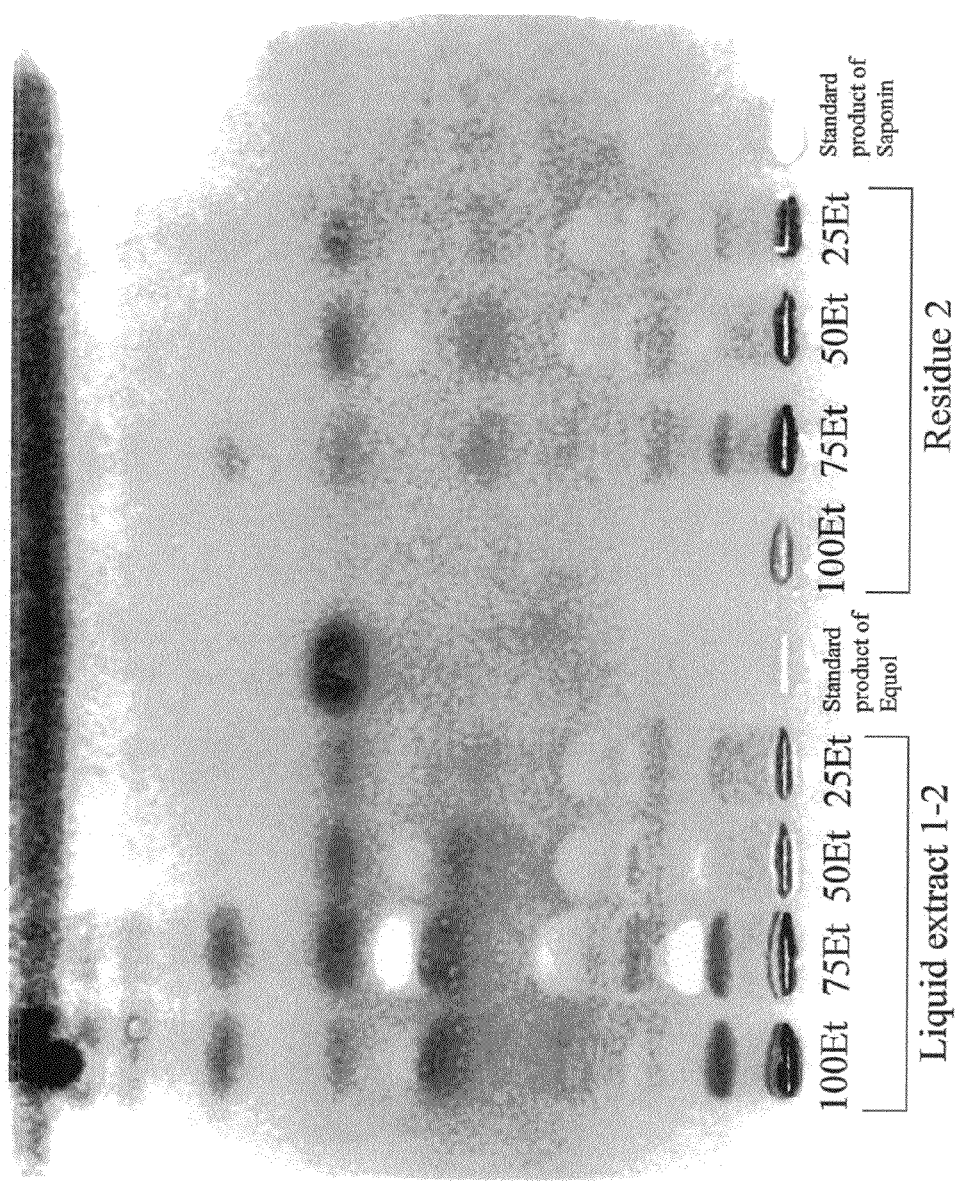
FIG. 6 shows the TLC analysis results indicating the equol contents of Liquid Extracts 1-2 and Residue 2 in Example 1-1.
Figure 7:
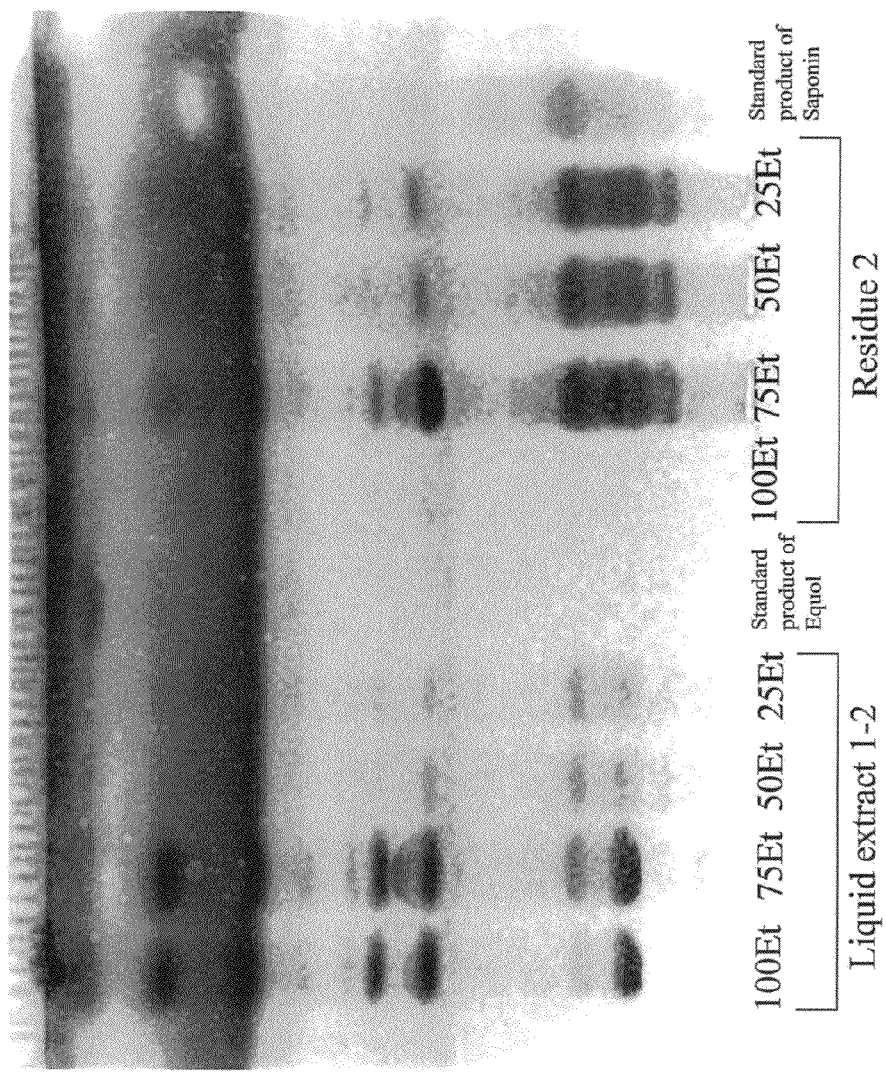
FIG. 7 shows TLC analysis results indicating the saponin contents of Liquid Extracts 1-2 and Residue 2 in Example 1-1.
Figure 8:
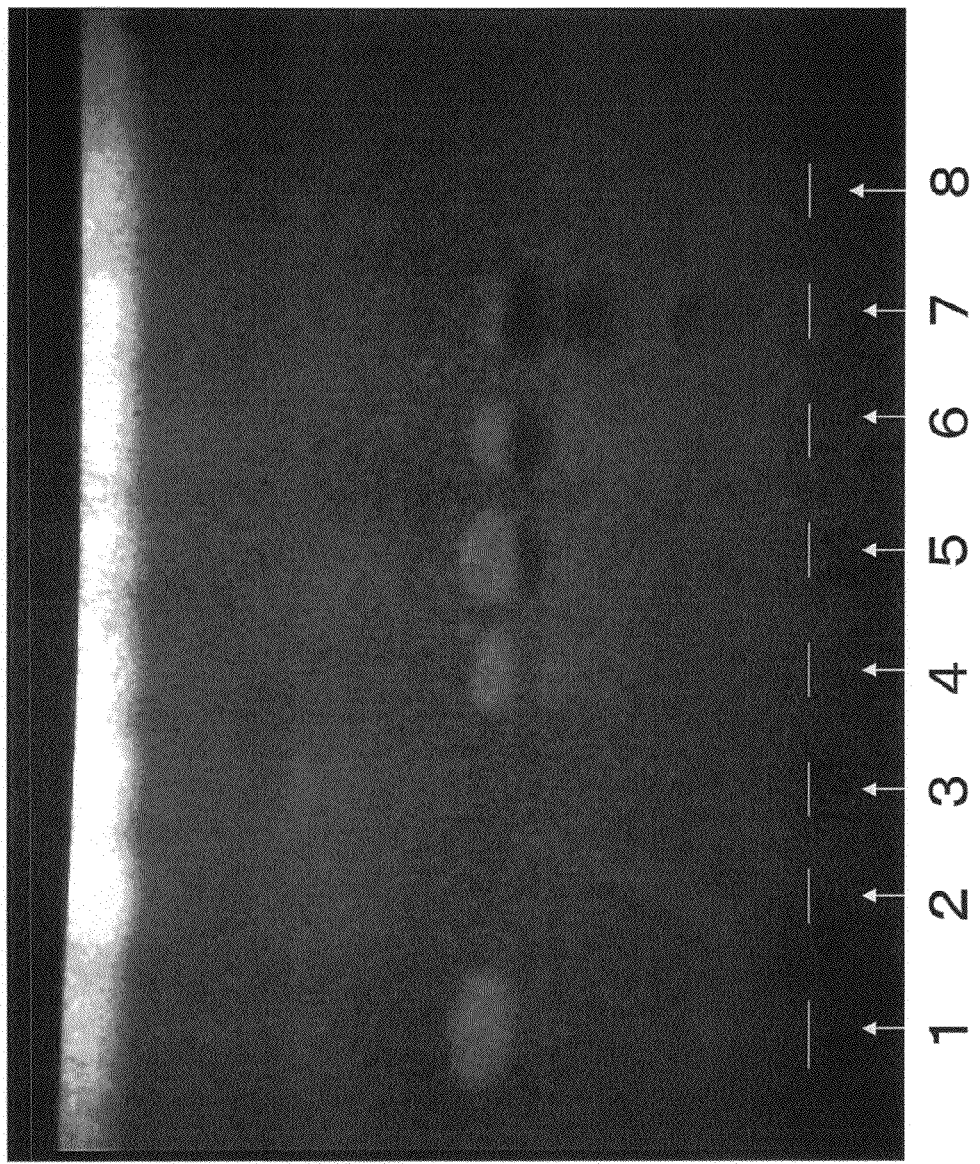
FIG. 8 shows TLC analysis results of solutions eluted by silica gel column chromatography in Example 2-1.

The invention claimed is:

1. A method for purifying an equol-containing substance derived from a soybean to obtain equol, comprising Steps 2-1 to 2-3:

Step 2-1 of subjecting the equol-containing substance to extraction using, as an extractant, an aqueous organic solvent containing 80-99 vol. % ethyl acetate, and concentrating the resulting liquid extract;

Step 2-2 of subjecting the equol concentrate obtained in Step 2-1 to silica gel column chromatography, and obtaining an equol-containing fraction, wherein a mobile phase of the silica gel column chromatography is a mixed solution of hexane and ethyl acetate; and Step 2-3 of removing the solvent from the equol-containing fraction obtained in Step 2-2, recrystallizing the resulting residue using a mixed solution of ethyl acetate and hexane, and collecting the deposited crystals.

2. The method according to claim 1, wherein Step 2-3 comprises a recrystallization using an aqueous alcohol solution after a recrystallization using a mixture of ethyl acetate and hexane.

3. The method according to claim 1, wherein the soybean is an equol-containing fermented soybean.

4. The method according to claim 3, wherein the equol-containing fermented soybean is an equol-containing fermented soybean hypocotyl obtained by fermenting a soybean hypocotyl with an equol-producing microorganism.

5. The method according to claim 1, which is used for preparing a food or drug.

* * * * *